(12) United States Patent
Badawi et al.

(10) Patent No.: US 11,857,460 B2
(45) Date of Patent: *Jan. 2, 2024

(54) OCULAR DELIVERY SYSTEMS AND METHODS

(71) Applicant: Sight Sciences, Inc., Menlo Park, CA (US)

(72) Inventors: David Y. Badawi, Glenview, IL (US); Daniel O'Keeffe, San Francisco, CA (US); Paul Badawi, Atherton, CA (US)

(73) Assignee: SIGHT SCIENCES, INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/990,589

(22) Filed: Nov. 18, 2022

(65) Prior Publication Data
US 2023/0181355 A1    Jun. 15, 2023

Related U.S. Application Data

(63) Continuation of application No. 17/033,408, filed on Sep. 25, 2020, now Pat. No. 11,504,270.
(Continued)

(51) Int. Cl.
*A61F 9/007* (2006.01)
*A61F 9/00* (2006.01)
(Continued)

(52) U.S. Cl.
CPC ........ *A61F 9/0008* (2013.01); *A61F 9/00781* (2013.01); *A61M 5/002* (2013.01);
(Continued)

(58) Field of Classification Search
CPC .... A61F 9/0008; A61F 9/00781; A61F 9/007; A61F 2009/00891; A61F 2230/0091;
(Continued)

(56) References Cited

U.S. PATENT DOCUMENTS 3,159,161 A    12/1964  Ness
4,068,664 A    1/1978   Sharp et al.
(Continued)

FOREIGN PATENT DOCUMENTS

CA    2244646 A1    2/1999
CA    2778452 A1    4/2011
(Continued)

OTHER PUBLICATIONS

Ahn, W. et al. (2002). "The "Gauge" System for the Medical Use," Anesth. Analg. 95:1125, with Table 1.
(Continued)

*Primary Examiner* — Nicholas J. Weiss
*Assistant Examiner* — Brandon W. Levy
(74) *Attorney, Agent, or Firm* — Cooley LLP

(57) ABSTRACT

Systems and methods for accessing Schlemm's canal, for delivering a fluid composition therein, and for tearing the trabecular meshwork. The fluid composition may be a viscoelastic fluid that is delivered into the canal to facilitate drainage of aqueous humor by disrupting the canal and surrounding trabeculocanalicular tissues. The systems described here may be configured to cut or tear the trabecular meshwork with the body of an elongate member located within Schlemm's canal.

24 Claims, 24 Drawing Sheets

Related U.S. Application Data

(60) Provisional application No. 62/907,474, filed on Sep. 27, 2019.

(51) Int. Cl.
*A61M 5/158* (2006.01)
*A61M 5/00* (2006.01)
*A61M 5/32* (2006.01)

(52) U.S. Cl.
CPC .......... *A61M 5/158* (2013.01); *A61M 5/3286* (2013.01); *A61M 5/3291* (2013.01); *A61M 2005/1585* (2013.01); *A61M 2210/0612* (2013.01)

(58) Field of Classification Search
CPC ................ A61F 9/0017; A61M 5/158; A61M 2210/0612; A61M 27/002; A61M 2202/04; A61M 2005/2073; A61M 37/0069; A61M 2005/3152; A61M 5/24; A61M 5/20; A61M 5/31511; A61M 5/3158; A61M 2205/581; A61M 2205/583; A61K 9/0051; Y10S 623/905; A61P 27/02; A61B 17/3421; A61B 17/3417; A61B 17/2833; A61B 2017/2837; A61B 2017/2912; A61B 2017/2913; A61B 2017/00367; A61B 2017/00371; A61B 2017/00376; A61B 2017/0038; A61B 2017/00384; A61B 2017/00389; A61B 2017/00393; A61B 2017/00115; A61B 2017/2923; A61B 17/1155; A61B 17/07207; A61B 2090/035; A61B 2017/00407
See application file for complete search history.

(56) References Cited

U.S. PATENT DOCUMENTS

| | | |
|---|---|---|
| 4,457,757 A | 7/1984 | Molteno |
| 4,501,274 A | 2/1985 | Skjaerpe |
| 4,553,545 A | 11/1985 | Maass et al. |
| 4,719,825 A | 1/1988 | LaHaye et al. |
| 4,863,457 A | 9/1989 | Lee |
| 4,936,825 A | 6/1990 | Ungerleider |
| 4,957,505 A | 9/1990 | McDonald |
| 5,092,837 A | 3/1992 | Ritch et al. |
| 5,180,362 A | 1/1993 | Worst |
| 5,284,476 A | 2/1994 | Koch |
| 5,358,473 A | 10/1994 | Mitchell |
| 5,360,399 A | 11/1994 | Stegmann |
| 5,368,572 A | 11/1994 | Shirota |
| 5,486,165 A | 1/1996 | Stegmann |
| 5,540,657 A | 7/1996 | Kurjan et al. |
| 5,558,634 A | 9/1996 | Mitchell |
| 5,569,197 A | 10/1996 | Helmus et al. |
| 5,626,558 A | 5/1997 | Suson |
| 5,639,278 A | 6/1997 | Dereume et al. |
| 5,792,099 A | 8/1998 | DeCamp et al. |
| 5,792,103 A | 8/1998 | Schwartz et al. |
| 5,868,697 A | 2/1999 | Richter et al. |
| 6,036,678 A | 3/2000 | Giungo |
| 6,050,970 A | 4/2000 | Baerveldt |
| 6,050,999 A | 4/2000 | Paraschac et al. |
| 6,299,603 B1 | 10/2001 | Hecker et al. |
| 6,309,375 B1 | 10/2001 | Glines et al. |
| 6,375,642 B1 | 4/2002 | Grieshaber et al. |
| 6,491,670 B1 | 12/2002 | Toth et al. |
| 6,494,857 B1 | 12/2002 | Neuhann |
| 6,508,779 B1 | 1/2003 | Suson |
| 6,524,275 B1 | 2/2003 | Lynch et al. |
| 6,533,768 B1 | 3/2003 | Hill |
| 6,616,996 B1 | 9/2003 | Keith et al. |
| 6,626,858 B2 | 9/2003 | Lynch et al. |
| 6,666,841 B2 | 12/2003 | Gharib et al. |
| 6,726,676 B2 | 4/2004 | Stegmann et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,840,952 B2 | 1/2005 | Saker et al. |
| 6,843,792 B2 * | 1/2005 | Nishtala ............ A61B 17/3478 606/205 |
| 6,893,415 B2 | 5/2005 | Madsen et al. |
| 6,955,656 B2 | 10/2005 | Bergheim et al. |
| 6,962,573 B1 | 11/2005 | Wilcox |
| 7,094,225 B2 | 8/2006 | Tu et al. |
| 7,135,009 B2 | 11/2006 | Tu et al. |
| 7,186,232 B1 | 3/2007 | Smedley et al. |
| 7,192,412 B1 | 3/2007 | Zhou et al. |
| 7,207,980 B2 | 4/2007 | Christian et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 | 2/2009 | Haffner et al. |
| 7,713,228 B2 | 5/2010 | Robin |
| 7,740,604 B2 | 6/2010 | Schieber et al. |
| 7,806,847 B2 | 10/2010 | Wilcox |
| 7,850,637 B2 | 12/2010 | Lynch et al. |
| 7,867,205 B2 | 1/2011 | Bergheim et al. |
| 7,909,789 B2 | 3/2011 | Badawi et al. |
| 7,951,155 B2 | 5/2011 | Smedley et al. |
| 7,967,772 B2 | 6/2011 | McKenzie et al. |
| 8,034,105 B2 | 10/2011 | Stegmann et al. |
| 8,075,511 B2 | 12/2011 | Tu et al. |
| 8,109,896 B2 | 2/2012 | Nissan et al. |
| 8,123,729 B2 | 2/2012 | Yamamoto et al. |
| 8,133,208 B2 | 3/2012 | Hetherington |
| 8,137,307 B2 | 3/2012 | Tennican et al. |
| 8,152,752 B2 | 4/2012 | Lynch et al. |
| 8,172,899 B2 | 5/2012 | Silvestrini et al. |
| 8,267,882 B2 | 9/2012 | Euteneuer et al. |
| 8,273,050 B2 | 9/2012 | Bergheim et al. |
| 8,282,592 B2 | 10/2012 | Schieber et al. |
| 8,287,482 B2 | 10/2012 | Badawi et al. |
| 8,333,742 B2 | 12/2012 | Bergheim et al. |
| 8,337,509 B2 | 12/2012 | Schieber et al. |
| 8,348,924 B2 | 1/2013 | Christian et al. |
| 8,366,653 B2 | 2/2013 | Shareef et al. |
| 8,372,026 B2 | 2/2013 | Schieber et al. |
| 8,388,568 B2 | 3/2013 | Lynch et al. |
| 8,403,920 B2 | 3/2013 | Lind et al. |
| 8,414,518 B2 | 4/2013 | Schieber et al. |
| 8,414,636 B2 | 4/2013 | Nabulsi et al. |
| 8,425,449 B2 | 4/2013 | Wardle et al. |
| 8,425,450 B2 | 4/2013 | Wilcox |
| 8,439,972 B2 | 5/2013 | Badawi et al. |
| 8,444,589 B2 | 5/2013 | Silvestrini |
| 8,491,549 B2 | 7/2013 | Conston et al. |
| 8,512,321 B2 | 8/2013 | Baerveldt et al. |
| 8,512,404 B2 | 8/2013 | Frion et al. |
| 8,529,622 B2 | 9/2013 | Badawi et al. |
| 8,540,659 B2 | 9/2013 | Berlin |
| 8,540,681 B2 | 9/2013 | Hetherington |
| 8,545,431 B2 | 10/2013 | Rickard |
| 8,568,391 B2 | 10/2013 | Kearns et al. |
| 8,617,094 B2 | 12/2013 | Smedley et al. |
| 8,657,776 B2 | 2/2014 | Wardle et al. |
| 8,663,150 B2 | 3/2014 | Wardle et al. |
| 8,715,266 B2 | 5/2014 | Bos |
| 8,734,377 B2 | 5/2014 | Schieber et al. |
| 8,747,299 B2 | 6/2014 | Grieshaber |
| 8,771,217 B2 | 7/2014 | Lynch et al. |
| 8,801,648 B2 | 8/2014 | Bergheim et al. |
| 8,808,222 B2 | 8/2014 | Schieber et al. |
| 8,827,990 B2 | 9/2014 | Van Valen et al. |
| 8,852,137 B2 | 10/2014 | Horvath et al. |
| 8,876,898 B2 | 11/2014 | Badawi et al. |
| 8,888,734 B2 | 11/2014 | Nissan et al. |
| 8,894,603 B2 | 11/2014 | Badawi et al. |
| 8,926,546 B2 | 1/2015 | Wilcox |
| 8,961,447 B2 | 2/2015 | Schieber et al. |

(56) References Cited

U.S. PATENT DOCUMENTS

| | | |
|---|---|---|
| 9,039,650 B2 | 5/2015 | Schieber et al. |
| 9,044,301 B1 | 6/2015 | Pinchuk et al. |
| 9,050,169 B2 | 6/2015 | Schieber et al. |
| 9,066,750 B2 | 6/2015 | Wardle et al. |
| 9,066,783 B2 | 6/2015 | Euteneuer et al. |
| 9,095,412 B2 | 8/2015 | Badawi et al. |
| 9,107,729 B2 | 8/2015 | Sorensen et al. |
| 9,125,723 B2 | 9/2015 | Horvath et al. |
| 9,155,655 B2 | 10/2015 | Schieber et al. |
| 9,192,516 B2 | 11/2015 | Horvath et al. |
| 9,211,213 B2 | 12/2015 | Wardle et al. |
| 9,216,109 B2 | 12/2015 | Badawi et al. |
| 9,220,632 B2 | 12/2015 | Smedley et al. |
| 9,226,850 B2 | 1/2016 | Baerveldt et al. |
| 9,226,852 B2 | 1/2016 | Schieber et al. |
| 9,301,875 B2 | 4/2016 | Tu et al. |
| 9,326,891 B2 | 5/2016 | Horvath et al. |
| 9,339,514 B2 | 5/2016 | Bos et al. |
| 9,351,874 B2 | 5/2016 | Schieber et al. |
| 9,358,155 B2 | 6/2016 | Sorensen et al. |
| 9,358,156 B2 | 6/2016 | Wardle et al. |
| 9,370,443 B2 | 6/2016 | Badawi et al. |
| 9,381,111 B2 | 7/2016 | Hickingbotham et al. |
| 9,402,767 B2 | 8/2016 | Schieber et al. |
| 9,486,361 B2 | 11/2016 | Badawi et al. |
| 9,492,319 B2 | 11/2016 | Grieshaber et al. |
| 9,492,320 B2 | 11/2016 | Lynch et al. |
| 9,510,973 B2 | 12/2016 | Wardle |
| 9,855,167 B2 | 1/2018 | Badawi et al. |
| 9,889,258 B2 | 2/2018 | Bengtsson et al. |
| 9,895,258 B2 | 2/2018 | Badawi et al. |
| 10,154,924 B2 | 12/2018 | Clauson et al. |
| 10,179,066 B2 | 1/2019 | Badawi et al. |
| 10,299,958 B2 | 5/2019 | Badawi et al. |
| 10,314,742 B2 | 6/2019 | Badawi et al. |
| 10,398,597 B2 | 9/2019 | Badawi et al. |
| 10,406,030 B2 | 9/2019 | Badawi et al. |
| 10,857,027 B2 | 12/2020 | Badawi et al. |
| 10,888,453 B2 | 1/2021 | Badawi et al. |
| 10,905,591 B1 | 2/2021 | Ianchulev |
| 11,090,188 B2 | 8/2021 | Badawi et al. |
| 11,116,660 B2 | 9/2021 | Badawi et al. |
| 11,166,847 B2 | 11/2021 | Badawi et al. |
| 11,259,961 B2 | 3/2022 | Ianchulev |
| 11,344,447 B2 | 5/2022 | Badawi et al. |
| 11,389,327 B2 | 7/2022 | Badawi et al. |
| 11,389,328 B2 | 7/2022 | Badawi et al. |
| 11,419,762 B2 | 8/2022 | Ianchulev |
| 11,419,886 B2 | 8/2022 | Badawi et al. |
| 11,471,324 B2 | 10/2022 | Badawi et al. |
| 11,504,270 B1 | 11/2022 | Badawi et al. |
| 11,554,134 B2 | 1/2023 | Badawi et al. |
| 11,617,679 B2 | 4/2023 | Badawi et al. |
| 2001/0014788 A1 | 8/2001 | Morris |
| 2002/0013546 A1 | 1/2002 | Grieshaber et al. |
| 2002/0013572 A1 | 1/2002 | Berlin |
| 2002/0055753 A1 | 5/2002 | Silvestrini |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2002/0165478 A1 | 11/2002 | Gharib et al. |
| 2003/0060447 A1 | 3/2003 | Karakelle et al. |
| 2003/0060752 A1 | 3/2003 | Bergheim et al. |
| 2003/0060873 A1 | 3/2003 | Gertner et al. |
| 2003/0120200 A1 | 6/2003 | Bergheim et al. |
| 2003/0181848 A1 | 9/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0044310 A1 | 3/2004 | Suzuki |
| 2004/0102719 A1 | 5/2004 | Keith et al. |
| 2004/0102729 A1 | 5/2004 | Haffner et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260228 A1 | 12/2004 | Lynch et al. |
| 2005/0038334 A1 | 2/2005 | Lynch et al. |
| 2005/0055082 A1 | 3/2005 | Ben Muvhar et al. |
| 2005/0090807 A1 | 4/2005 | Lynch et al. |
| 2005/0101967 A1 | 5/2005 | Weber et al. |
| 2005/0125003 A1 | 6/2005 | Pinchuk et al. |
| 2005/0165363 A1* | 7/2005 | Judson .............. A61M 5/31551 604/209 |
| 2005/0171507 A1 | 8/2005 | Christian |
| 2005/0192527 A1 | 9/2005 | Gharib et al. |
| 2005/0209549 A1 | 9/2005 | Bergheim et al. |
| 2005/0250788 A1 | 11/2005 | Tu et al. |
| 2005/0266047 A1 | 12/2005 | Tu et al. |
| 2005/0267555 A1 | 12/2005 | Marnfeldt et al. |
| 2005/0277864 A1 | 12/2005 | Haffner et al. |
| 2005/0288619 A1 | 12/2005 | Gharib et al. |
| 2006/0032507 A1 | 2/2006 | Tu |
| 2006/0034891 A1 | 2/2006 | Lawin et al. |
| 2006/0036207 A1 | 2/2006 | Koonmen et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0116626 A1 | 6/2006 | Smedley et al. |
| 2006/0149194 A1 | 7/2006 | Conston |
| 2006/0155300 A1 | 7/2006 | Stamper et al. |
| 2006/0173077 A1 | 8/2006 | Cagle |
| 2006/0173397 A1 | 8/2006 | Tu et al. |
| 2006/0173446 A1 | 8/2006 | Dacquay et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0217741 A1 | 9/2006 | Ghannoum |
| 2006/0241580 A1 | 10/2006 | Mittelstein et al. |
| 2007/0073275 A1 | 3/2007 | Conston et al. |
| 2007/0106236 A1 | 5/2007 | Coroneo |
| 2007/0191863 A1 | 8/2007 | De Juan, Jr. et al. |
| 2007/0260173 A1 | 11/2007 | Boukhny et al. |
| 2007/0276420 A1 | 11/2007 | Sorensen et al. |
| 2008/0004596 A1 | 1/2008 | Yun et al. |
| 2008/0058704 A1 | 3/2008 | Hee et al. |
| 2008/0058760 A1 | 3/2008 | Agerup |
| 2008/0058790 A1 | 3/2008 | Agerup |
| 2008/0082078 A1 | 4/2008 | Berlin |
| 2008/0300574 A1 | 12/2008 | Belson et al. |
| 2009/0036819 A1 | 2/2009 | Tu et al. |
| 2009/0036827 A1 | 2/2009 | Cazzini |
| 2009/0043321 A1 | 2/2009 | Conston et al. |
| 2009/0082862 A1 | 3/2009 | Schieber et al. |
| 2009/0132040 A1 | 5/2009 | Frion et al. |
| 2009/0227934 A1 | 9/2009 | Euteneuer et al. |
| 2009/0247955 A1 | 10/2009 | Yamamoto et al. |
| 2009/0287143 A1 | 11/2009 | Line |
| 2009/0287233 A1 | 11/2009 | Huculak |
| 2010/0019177 A1 | 1/2010 | Luckevich |
| 2010/0087774 A1 | 4/2010 | Haffner et al. |
| 2010/0121248 A1 | 5/2010 | Yu et al. |
| 2010/0173866 A1 | 7/2010 | Hee et al. |
| 2010/0179652 A1 | 7/2010 | Yamamoto et al. |
| 2010/0222802 A1 | 9/2010 | Gillespie |
| 2010/0241046 A1 | 9/2010 | Pinchuk et al. |
| 2010/0262174 A1 | 10/2010 | Sretavan et al. |
| 2011/0009874 A1* | 1/2011 | Wardle ................ A61F 9/0017 606/108 |
| 2011/0009958 A1 | 1/2011 | Wardle et al. |
| 2011/0098809 A1 | 4/2011 | Wardle et al. |
| 2011/0224597 A1 | 9/2011 | Stegmann et al. |
| 2011/0238009 A1 | 9/2011 | Meron et al. |
| 2011/0238075 A1 | 9/2011 | Clauson et al. |
| 2011/0306915 A1 | 12/2011 | De Juan, Jr et al. |
| 2012/0010702 A1 | 1/2012 | Stegmann et al. |
| 2012/0123315 A1 | 5/2012 | Horvath et al. |
| 2012/0123434 A1 | 5/2012 | Grabner et al. |
| 2012/0136306 A1 | 5/2012 | Bartha |
| 2012/0165720 A1 | 6/2012 | Horvath et al. |

(56) References Cited

U.S. PATENT DOCUMENTS

| | | |
|---|---|---|
| 2012/0191064 A1 | 7/2012 | Conston et al. |
| 2012/0197175 A1 | 8/2012 | Horvath et al. |
| 2012/0203160 A1 | 8/2012 | Kahook et al. |
| 2012/0220917 A1 | 8/2012 | Silvestrini et al. |
| 2012/0310072 A1 | 12/2012 | Grieshaber |
| 2012/0310137 A1 | 12/2012 | Silvestrini |
| 2012/0325704 A1 | 12/2012 | Kerns et al. |
| 2013/0041346 A1 | 2/2013 | Alon |
| 2013/0158462 A1 | 6/2013 | Wardle et al. |
| 2013/0245600 A1 | 9/2013 | Yamamoto et al. |
| 2013/0274655 A1 | 10/2013 | Jennings et al. |
| 2014/0018771 A1 | 1/2014 | Shekalim |
| 2014/0066833 A1 | 3/2014 | Yaron et al. |
| 2014/0081194 A1 | 3/2014 | Burns et al. |
| 2014/0121584 A1 | 5/2014 | Wardle et al. |
| 2014/0128847 A1 | 5/2014 | Lopez |
| 2014/0135916 A1 | 5/2014 | Clauson et al. |
| 2014/0163448 A1 | 6/2014 | Lind et al. |
| 2014/0171852 A1 | 6/2014 | Khor |
| 2014/0194916 A1 | 7/2014 | Ichikawa |
| 2014/0213958 A1 | 7/2014 | Clauson et al. |
| 2014/0236066 A1 | 8/2014 | Horvath et al. |
| 2014/0276332 A1 | 9/2014 | Crimaldi et al. |
| 2014/0288485 A1 | 9/2014 | Berlin |
| 2014/0309599 A1 | 10/2014 | Schaller |
| 2014/0364791 A1 | 12/2014 | Stegmann et al. |
| 2015/0005623 A1 | 1/2015 | Grover et al. |
| 2015/0011926 A1 | 1/2015 | Reitsamer et al. |
| 2015/0051699 A1 | 2/2015 | Badawi et al. |
| 2015/0065940 A1 | 3/2015 | Rangel-Friedman et al. |
| 2015/0080783 A1 | 3/2015 | Berlin |
| 2015/0112372 A1 | 4/2015 | Perez Grossmann |
| 2015/0119787 A1 | 4/2015 | Wardle et al. |
| 2015/0125328 A1 | 5/2015 | Bourne et al. |
| 2015/0133946 A1 | 5/2015 | Horvath et al. |
| 2015/0148615 A1 | 5/2015 | Brennan et al. |
| 2015/0216729 A1 | 8/2015 | Doci |
| 2015/0223981 A1 | 8/2015 | Smedley et al. |
| 2015/0223983 A1 | 8/2015 | Schieber et al. |
| 2015/0250649 A1 | 9/2015 | Euteneuer et al. |
| 2015/0257932 A1 | 9/2015 | Pinchuk et al. |
| 2015/0282982 A1 | 10/2015 | Schieber et al. |
| 2015/0313758 A1 | 11/2015 | Wilcox |
| 2015/0320596 A1 | 11/2015 | Gifford, III et al. |
| 2015/0374545 A1 | 12/2015 | Horvath et al. |
| 2016/0022486 A1 | 1/2016 | Clauson et al. |
| 2016/0051408 A1 | 2/2016 | Baerveldt et al. |
| 2016/0095985 A1 | 4/2016 | Novak |
| 2016/0100980 A1 | 4/2016 | Badawi et al. |
| 2016/0106589 A1 | 4/2016 | Mittelstein et al. |
| 2016/0135994 A1 | 5/2016 | Romoda et al. |
| 2016/0143778 A1 | 5/2016 | Aljuri et al. |
| 2016/0151204 A1 | 6/2016 | Haffner et al. |
| 2016/0158453 A1* | 6/2016 | Oakley ............ A61M 5/31558 |
| | | 604/211 |
| 2016/0220417 A1 | 8/2016 | Schieber et al. |
| 2016/0220418 A1 | 8/2016 | Sorensen et al. |
| 2016/0256317 A1 | 9/2016 | Horvath et al. |
| 2016/0256323 A1 | 9/2016 | Horvath et al. |
| 2016/0287438 A1* | 10/2016 | Badawi ................ A61K 31/728 |
| 2016/0302965 A1 | 10/2016 | Erickson et al. |
| 2016/0331588 A1 | 11/2016 | Ambati et al. |
| 2016/0346006 A1 | 12/2016 | Hickengbotham et al. |
| 2016/0354248 A1 | 12/2016 | Kahook |
| 2017/0202707 A1 | 7/2017 | Badawi et al. |
| 2017/0258507 A1 | 9/2017 | Hetherington |
| 2018/0243131 A1 | 8/2018 | Erickson et al. |
| 2018/0263817 A1 | 9/2018 | Roeber et al. |
| 2019/0314200 A1 | 10/2019 | Badawi et al. |
| 2020/0038243 A1 | 2/2020 | Badawi et al. |
| 2020/0121503 A1 | 4/2020 | Badawi et al. |
| 2021/0236333 A1 | 8/2021 | Badawi et al. |
| 2021/0386584 A1 | 12/2021 | Badawi et al. |
| 2022/0104967 A1 | 4/2022 | Badawi et al. |
| 2022/0160668 A1 | 5/2022 | Badawi et al. |
| 2022/0168146 A1 | 6/2022 | Badawi et al. |
| 2022/0280339 A1 | 9/2022 | Badawi et al. |
| 2022/0280340 A1 | 9/2022 | Badawi et al. |
| 2022/0354695 A1 | 11/2022 | Badawi et al. |
| 2022/0378612 A1 | 12/2022 | Badawi et al. |

FOREIGN PATENT DOCUMENTS

| | | |
|---|---|---|
| CN | 1678407 A | 10/2005 |
| CN | 101505830 A | 8/2009 |
| CN | 201824103 U | 5/2011 |
| CN | 102202706 A | 9/2011 |
| CN | 202400240 U | 8/2012 |
| EP | 2 830 553 B1 | 12/2017 |
| JP | 03-168154 A | 7/1991 |
| JP | 2002-541976 A | 12/2002 |
| JP | 2003-180730 A | 7/2003 |
| JP | 2005-510317 A | 4/2005 |
| JP | 2005-538809 A | 12/2005 |
| JP | 2007-527251 A | 9/2007 |
| JP | 2012-527318 A | 11/2012 |
| JP | 2013-512707 A | 4/2013 |
| JP | 2014-036867 A | 2/2014 |
| JP | 2014-533600 A | 12/2014 |
| WO | WO-00/64391 A1 | 11/2000 |
| WO | WO-00/64393 A1 | 11/2000 |
| WO | WO-01/97727 A1 | 12/2001 |
| WO | WO-02/36052 A1 | 5/2002 |
| WO | WO-03/045582 A1 | 6/2003 |
| WO | WO-2004/026361 A1 | 4/2004 |
| WO | WO-2004/069664 A2 | 8/2004 |
| WO | WO-2004/069664 A3 | 8/2004 |
| WO | WO-2005/016418 A1 | 2/2005 |
| WO | WO-2005/105197 A2 | 11/2005 |
| WO | WO-2005/105197 A3 | 11/2005 |
| WO | WO-2005/107664 A2 | 11/2005 |
| WO | WO-2005/107664 A3 | 11/2005 |
| WO | WO-2005/117752 A1 | 12/2005 |
| WO | WO-2006/066103 A2 | 6/2006 |
| WO | WO-2006/066103 A3 | 6/2006 |
| WO | WO-2008/002377 A1 | 1/2008 |
| WO | WO-2009/042596 A2 | 4/2009 |
| WO | WO-2009/042596 A3 | 4/2009 |
| WO | WO-2010/065970 A1 | 6/2010 |
| WO | WO-2011/006078 A1 | 1/2011 |
| WO | WO-2011/006113 A1 | 1/2011 |
| WO | WO-2011/050360 A1 | 4/2011 |
| WO | WO-2011/097408 A1 | 8/2011 |
| WO | WO-2011/106781 A1 | 9/2011 |
| WO | WO-2013/141898 A1 | 9/2013 |
| WO | WO-2016/042162 A1 | 3/2016 |
| WO | WO-2016/159999 A1 | 10/2016 |

OTHER PUBLICATIONS

Aragona, P. et al. (2002). "Long Term Treatment with Sodium Hyaluronate-Containing Artificial Tears Reduces Ocular Surface Damage in Patients with Dry Eye," Br. J. Ophthalmol. 86:181-184.

Bahler, C.K. et al. (2004). "Trabecular bypass stents decrease intraocular pressure in cultured human anterior segments," Am. J. Ophthalmol. 138:988-994.

Balazs, E.A. et al. (1972). "Hyaluronic Acid and Replacement of Vitreous and Aqueous Humor," Modern Problems in Ophthalmology 10:3-21.

Boyle, E.L. (Feb. 1, 2006). "New Glaucoma Devices Take Different Approaches to IOP Lowering," *Ocular Surgery News U.S. Edition*, located at <http://www.osnsupersite.com/view.aspx?rid=12436>, last visited on Apr. 23, 2012, 4 pages, revisited on Apr. 19, 2016, 5 pages.

Butany, J. et al. (2005). "Coronary artery stents; identification and evaluation," J. Clin. Pathol. 58:795-804.

ClinicalTrials.Gov (2006). A study of the trabecular micro-bypass stent in combination with cataract surgery in subjects with open angle glaucoma, NCT00323284, 6 total pages.

Colombo, A. et al. (2002). "Selection of coronary stents," J. Am. Coll. Cardiol. 40:1021-1033.

(56) References Cited

OTHER PUBLICATIONS

Corrected Notice of Allowability dated Nov. 23, 2018, for U.S. Appl. No. 14/816,822, filed Aug. 3, 2015, 2 pages.
Corrected Notice of Allowability dated Dec. 12, 2018, for U.S. Appl. No. 14/816,822, filed Aug. 3, 2015, 2 pages.
Corrected Notice of Allowability dated Feb. 21, 2019, for U.S. Appl. No. 14/675,580, filed Mar. 31, 2015, 6 pages.
Corrected Notice of Allowability dated Apr. 3, 2019, for U.S. Appl. No. 14/675,580, filed Mar. 31, 2015, 3 pages.
Corrected Notice of Allowability dated Oct. 12, 2021, for U.S. Appl. No. 16/532,260, filed Aug. 5, 2019, 2 pages.
Corrected Notice of Allowability dated Apr. 15, 2022, for U.S. Appl. No. 17/239,270, filed Apr. 23, 2021, 2 pages.
Corrected Notice of Allowability dated Oct. 14, 2022, for U.S. Appl. No. 17/033,408, filed Sep. 25, 2020, 2 pages.
Corrected Notice of Allowability dated Mar. 3, 2023, for U.S. Appl. No. 17/827,494, filed May 27, 2022, 5 pages.
Drusedau, M.U.H. et al. (2000). "Viscocanalostomy for primary open-angle glaucoma: The gross Pankow experience," J. Cataract Refract. Surg. 26:1367-1373.
Extended European Search Report dated Apr. 22, 2015, for EP Patent Application No. 11 740 372.5, filed Feb. 3, 2011, 6 pages.
Extended European Search Report dated Jun. 9, 2016, for European Patent Application No. 16 155 079.3, filed May 31, 2007, 7 pages.
Extended European Search Report dated May 17, 2011, for European Patent Application No. 11 162 487.0, filed May 31, 2007, 6 pages.
Extended European Search Report dated Mar. 24, 2016, for European Patent Application No. 12 871 982.0, filed Oct. 4, 2012, 7 pages.
Extended European Search Report dated Nov. 20, 2018, for European Patent Application No. 15 888 007.0, filed Mar. 31, 2015, 9 pages.
Extended European Search Report dated Feb. 4, 2022, for European Patent Application No. 21 179 625.5, filed Mar. 31, 2015, 8 pages.
Final Office Action dated Nov. 1, 2010, for U.S. Appl. No. 11/475,523, filed Jun. 26, 2006, 12 pages.
Final Office Action dated Jul. 19, 2012, for U.S. Appl. No. 13/245,811, filed Sep. 26, 2011, 6 pages.
Final Office Action dated Feb. 1, 2013, for U.S. Appl. No. 13/020,706, filed Feb. 3, 2011, 6 pages.
Final Office Action dated Sep. 15, 2014, for U.S. Appl. No. 13/025,112, filed Feb. 10, 2011, 13 pages.
Final Office Action dated Sep. 20, 2013, for U.S. Appl. No. 13/644,780, filed Oct. 4, 2012, 16 pages.
Final Office Action dated Nov. 12, 2013, for U.S. Appl. No. 13/644,748, filed Oct. 4, 2012, 8 pages.
Final Office Action dated Jan. 8, 2014, for U.S. Appl. No. 13/644,758, filed Oct. 4, 2012, 8 pages.
Final Office Action dated Sep. 3, 2014, for U.S. Appl. No. 13/644,758, filed Oct. 4, 2012, 8 pages.
Final Office Action dated Apr. 23, 2015, for U.S. Appl. No. 14/527,292, filed Oct. 29, 2014, 8 pages.
Final Office Action dated Aug. 19, 2015, for U.S. Appl. No. 13/445,816, filed Apr. 12, 2012, 6 pages.
Final Office Action dated Mar. 9, 2016, for U.S. Appl. No. 14/539,648, filed Nov. 12, 2014, 11 pages.
Final Office Action dated Oct. 3, 2016, for U.S. Appl. No. 13/644,769, filed Oct. 4, 2012, 27 pages.
Final Office Action dated May 18, 2017, for U.S. Appl. No. 14/539,648, filed Nov. 12, 2014, 14 pages.
Final Office Action dated Jan. 29, 2018, for U.S. Appl. No. 14/973,620, filed Dec. 17, 2015, 19 pages.
Final Office Action dated Apr. 6, 2018, for U.S. Appl. No. 15/683,652, filed Aug. 22, 2017, 11 pages.
Final Office Action dated Jun. 1, 2018, for U.S. Appl. No. 14/816,822, filed Aug. 3, 2015, 6 pages.
Final Office Action dated Oct. 19, 2018, for U.S. Appl. No. 15/683,652, filed Aug. 22, 2017, 8 pages.
Final Office Action dated Apr. 19, 2019, for U.S. Appl. No. 14/973,620, filed Dec. 17, 2015, 12 pages.
Final Office Action dated Jun. 9, 2020, for U.S. Appl. No. 15/854,126, filed Dec. 26, 2017, 9 pages.
Final Office Action dated Jun. 9, 2020, for U.S. Appl. No. 16/189,882, filed Nov. 13, 2018, 12 pages.
Final Office Action dated Apr. 1, 2021, for U.S. Appl. No. 16/532,260, filed Aug. 5, 2019, 8 pages.
Final Office Action dated Dec. 21, 2021, for U.S. Appl. No. 17/239,270, filed Apr. 23, 2021, 14 pages.
Final Office Action dated Dec. 27, 2022, for U.S. Appl. No. 17/827,485, filed May 27, 2022, 30 pages.
Glaukos iStent (2022). iStent inject® W, 9 total pages.
Guerrero, A.H. et al. (2000). "Complications of glaucoma drainage implant surgery," Int. Ophthalmol. Clin. 40:149-163.
International Search Report dated Nov. 30, 2007, for PCT Application No. PCT/US2007/013038, filed May 31, 2007, 4 pages.
International Search Report dated Apr. 5, 2011, for PCT Application No. PCT/US2011/023643, filed Feb. 3, 2011, 2 pages.
International Search Report dated Feb. 1, 2013, for PCT Application No. PCT/US2012/058751, filed Oct. 4, 2012, 4 pages.
International Search Report dated Sep. 14, 2015, for PCT Application No. PCT/US2015/023720, filed Mar. 31, 2015, 5 pages.
International Search Report dated Nov. 2, 2022, for PCT Application No. PCT/US2022/031457, filed May 27, 2022, 4 pages.
Jacob, J.S. (1985). "Corneal thickness changes following cataract surgery: effect of lens implantation and sodium hyaluronate," British Journal of Ophthalmology 69:567-571.
Johnson, D.H. et al. (2001). "How does nonpenetrating glaucoma surgery work? Aqueous outflow resistance and glaucoma surgery." J. Glaucoma 10:55-67.
Minckler, D. et al. (2006). "Aqueous shunts for glaucoma review," Cochrane Library, 47 total pages.
Myers, T.D. et al. (1999). "Comparison of the Effects of Viscoelastic Agents on Clinical Properties of the Unfolder Lens Injection System," Journal of Cataract and Refractive Surgery 25:953-958.
Nesterov, A.P. (1970). "Role of Blockage of Schlemm's Canal in Pathogenesis of Primary Open-Angle Glaucoma," Am. J. Ophthalmol. 70:691-696.
Non-Final Office Action dated May 17, 2010, for U.S. Appl. No. 11/475,523, filed Jun. 26, 2006, 10 pages.
Non-Final Office Action dated Jan. 26, 2012, for U.S. Appl. No. 12/695,053, filed Jan. 27, 2010, 10 pages.
Non-Final Office Action dated Mar. 15, 2012, for U.S. Appl. No. 13/245,811, filed Sep. 26, 2011, 4 pages.
Non-Final Office Action dated May 11, 2012, for U.S. Appl. No. 13/020,706, filed Feb. 3, 2011, 5 pages.
Non-Final Office Action dated Nov. 9, 2012, for U.S. Appl. No. 13/245,811, filed Sep. 26, 2011, 5 pages.
Non-Final Office Action dated Apr. 24, 2013, for U.S. Appl. No. 13/644,780, filed Oct. 4, 2012, 13 pages.
Non-Final Office Action dated Jun. 12, 2013, for U.S. Appl. No. 13/644,748, filed Oct. 4, 2012, 8 pages.
Non-Final Office Action dated Sep. 9, 2013, for U.S. Appl. No. 13/644,758, filed Oct. 4, 2012, 7 pages.
Non-Final Office Action dated Feb. 7, 2014, for U.S. Appl. No. 13/644,780, filed Oct. 4, 2012, 12 pages.
Non-Final Office Action dated Feb. 24, 2014, for U.S. Appl. No. 13/025,112, filed Feb. 10, 2011, 12 pages.
Non-Final Office Action dated May 15, 2014, for U.S. Appl. No. 13/644,758, filed Oct. 4, 2012, 7 pages.
Non-Final Office Action dated Nov. 28, 2014, for U.S. Appl. No. 13/644,748, filed Oct. 4, 2012, 7 pages.
Non-Final Office Action dated Jan. 14, 2015, for U.S. Appl. No. 13/644,758, filed Oct. 4, 2012, 10 pages.
Non-Final Office Action dated Feb. 4, 2015, for U.S. Appl. No. 13/445,816, filed Apr. 12, 2012, 6 pages.
Non-Final Office Action dated Feb. 23, 2015, for U.S. Appl. No. 13/025,112, filed Feb. 10, 2011, 17 pages.
Non-Final Office Action dated Jul. 10, 2015, for U.S. Appl. No. 13/025,112, filed Feb. 10, 2011, 16 pages.
Non-Final Office Action dated Oct. 7, 2015, U.S. for U.S. Appl. No. 14/527,292, filed Oct. 29, 2014, 5 pages.

(56) References Cited

OTHER PUBLICATIONS

Non-Final Office Action dated Nov. 3, 2015, for U.S. Appl. No. 14/539,648, filed Nov. 12, 2014, 7 pages.
Non-Final Office Action dated Dec. 14, 2015, for U.S. Appl. No. 13/445,816, filed Apr. 12, 2012, 7 pages.
Non-Final Office Action dated Jun. 7, 2016, for U.S. Appl. No. 14/527,292, filed Oct. 29, 2014, 5 pages.
Non-Final Office Action dated Feb. 25, 2016, for U.S. Appl. No. 13/644,769, filed Oct. 4, 2012, 19 pages.
Non-Final Office Action dated Jan. 18, 2017, for U.S. Appl. No. 14/539,648, filed Nov. 12, 2014, 13 pages.
Non-Final Office Action dated Mar. 22, 2017, for U.S. Appl. No. 13/644,769, filed Oct. 4, 2012, 31 pages.
Non-Final Office Action dated Aug. 28, 2017, for U.S. Appl. No. 14/973,620, filed Dec. 17, 2015, 6 pages.
Non-Final Office Action dated Nov. 7, 2017, for U.S. Appl. No. 14/816,822, filed Aug. 3, 2015, 14 pages.
Non-Final Office Action dated Dec. 15, 2017, for U.S. Appl. No. 15/343,147, filed Nov. 3, 2016, 12 pages.
Non-Final Office Action dated Apr. 4, 2018, for U.S. Appl. No. 14/675,580, filed Mar. 31, 2015, 10 pages.
Non-Final Office Action dated Aug. 9, 2018, for U.S. Appl. No. 15/182,165, filed Jun. 14, 2016, 9 pages.
Non-Final Office Action dated Aug. 29, 2018, for U.S. Appl. No. 14/973,620, filed Dec. 17, 2015, 11 pages.
Non-Final Office Action dated Sep. 20, 2018, for U.S. Appl. No. 15/340,911, filed Nov. 1, 2016, 7 pages.
Non-Final Office Action dated Oct. 7, 2019, for U.S. Appl. No. 15/854,126, filed Dec. 26, 2017, 13 pages.
Non-Final Office Action dated Nov. 25, 2019, for U.S. Appl. No. 16/189,882, filed Nov. 13, 2018, 12 pages.
Non-Final Office Action dated Aug. 10, 2020, for U.S. Appl. No. 14/973,620, filed Dec. 17, 2015, 8 pages.
Non-Final Office Action dated Oct. 1, 2020, for U.S. Appl. No. 16/397,733, filed Apr. 29, 2019, 7 pages.
Non-Final Office Action dated Jul. 15, 2021, for U.S. Appl. No. 17/239,263, filed Apr. 23, 2021, 9 pages.
Non-Final Office Action dated Aug. 26, 2021, for U.S. Appl. No. 17/239,270, filed Apr. 23, 2021, 21 pages.
Non-Final Office Action dated Mar. 4, 2022, for U.S. Appl. No. 17/553,671, filed Dec. 16, 2021, 9 pages.
Non-Final Office Action dated Mar. 10, 2022, for U.S. Appl. No. 17/553,408, filed Dec. 16, 2021, 18 pages.
Non-Final Office Action dated Apr. 26, 2022, for U.S. Appl. No. 16/413,466, filed May 15, 2019, 8 pages.
Non-Final Office Action dated Jul. 27, 2022, for U.S. Appl. No. 16/526,832, filed Jul. 30, 2019, 8 pages.
Non-Final Office Action dated Aug. 4, 2022, for U.S. Appl. No. 17/827,494, filed May 27, 2022, 20 pages.
Non-Final Office Action dated Aug. 24, 2022, for U.S. Appl. No. 17/827,485, filed May 27, 2022, 25 pages.
Non-Final Office Action dated Mar. 16, 2023, for U.S. Appl. No. 17/397,817, filed Aug. 9, 2021, 8 pages.
Non-Final Office Action dated Jun. 23, 2023, for U.S. Appl. No. 18/130,353, filed Apr. 3, 2023, 15 pages.
Non-Final Office Action dated Jun. 26, 2023, for U.S. Appl. No. 18/130,354, filed Apr. 3, 2023, 16 pages.
Notice of Allowance dated Feb. 2, 2011, for U.S. Appl. No. 11/475,523, filed Jun. 26, 2006, 6 pages.
Notice of Allowance dated Jun. 11, 2012, for U.S. Appl. No. 12/695,053, filed Jan. 27, 2010, 7 pages.
Notice of Allowance dated Apr. 2, 2013, for U.S. Appl. No. 13/245,811, filed Sep. 26, 2011, 6 pages.
Notice of Allowance dated May 10, 2013, for U.S. Appl. No. 13/020,706, filed Feb. 3, 2011, 8 pages.
Notice of Allowance dated Jul. 7, 2014, for U.S. Appl. No. 14/012,963, filed Aug. 28, 2013, 6 pages.
Notice of Allowance dated Jul. 23, 2014, for U.S. Appl. No. 13/644,780, filed Oct. 4, 2012, 8 pages.
Notice of Allowance dated Mar. 30, 2015, for U.S. Appl. No. 13/644,748, filed Oct. 4, 2012, 5 pages.
Notice of Allowance dated Aug. 10, 2015, for U.S. Appl. No. 13/644,758, filed Oct. 4, 2012, 7 pages.
Notice of Allowance dated Mar. 1, 2016, for U.S. Appl. No. 13/025,112, filed Feb. 10, 2011, 7 pages.
Corrected Notice of Allowability dated Apr. 25, 2016, U.S. Appl. No. 13/025,112, filed Feb. 10, 2011, 2 pages.
Notice of Allowance dated Jul. 13, 2016, for U.S. Appl. No. 13/445,816, filed Apr. 12, 2012, 7 pages.
Corrected Notice of Allowability dated Sep. 1, 2016, for U.S. Appl. No. 13/445,816, filed Apr. 12, 2012, 2 pages.
Notice of Allowance dated Oct. 25, 2017, for U.S. Appl. No. 13/644,769, filed Oct. 4, 2012, 8 pages.
Notice of Allowance dated Nov. 21, 2017, for U.S. Appl. No. 14/539,648, filed Nov. 12, 2014, 10 pages.
Notice of Allowance dated Aug. 31, 2018, for U.S. Appl. No. 14/816,822, filed Aug. 3, 2015, 7 pages.
Notice of Allowance dated Jan. 9, 2019, for U.S. Appl. No. 14/675,580, filed Mar. 31, 2015, 9 pages.
Notice of Allowance dated Feb. 6, 2019, for U.S. Appl. No. 15/182,165, filed Jun. 14, 2016, 8 pages.
Notice of Allowance dated Apr. 15, 2019, for U.S. Appl. No. 15/683,652, filed Aug. 22, 2017, 5 pages.
Notice of Allowance dated Apr. 23, 2019, for U.S. Appl. No. 15/340,911, filed Nov. 1, 2016, 5 pages.
Notice of Allowance dated Aug. 20, 2020, for U.S. Appl. No. 16/189,882, filed Nov. 13, 2018, 8 pages.
Notice of Allowance dated Sep. 16, 2020, for U.S. Appl. No. 15/854,126, filed Dec. 26, 2017, 9 pages.
Notice of Allowance dated Aug. 2, 2021, for U.S. Appl. No. 17/239,263, filed Apr. 23, 2021, 5 pages.
Notice of Allowance dated Sep. 17, 2021, for U.S. Appl. No. 16/532,260, filed Aug. 5, 2019, 9 pages.
Notice of Allowance dated Mar. 15, 2022, for U.S. Appl. No. 17/239,270, filed Apr. 23, 2021, 8 pages.
Notice of Allowance dated May 31, 2022, for U.S. Appl. No. 17/553,671, filed Dec. 16, 2021, 7 pages.
Notice of Allowance dated Jun. 8, 2022, for U.S. Appl. No. 16/413,466, filed May 15, 2019, 5 pages.
Notice of Allowance dated Jun. 28, 2022, for U.S. Appl. No. 17/553,408, filed Dec. 16, 2021, 9 pages.
Notice of Allowance dated Jul. 8, 2022, for U.S. Appl. No. 17/033,408, filed Sep. 25, 2020, 12 pages.
Notice of Allowance dated Nov. 23, 2022, for U.S. Appl. No. 17/827,494, filed May 27, 2022, 8 pages.
Notice of Allowance dated Nov. 29, 2022, for U.S. Appl. No. 16/526,832, filed Jul. 30, 2019, 5 pages.
Notice of Allowance dated May 4, 2023, for U.S. Appl. No. 17/827,485, filed May 27, 2022, 12 pages.
Notice of Allowance dated May 11, 2023, for U.S. Appl. No. 16/526,832, filed Jul. 30, 2019, 5 pages.
Razeghinejad, M.R. et al. (2011). "A History of the Surgical Management of Glaucoma," Optom. Vis. Sci. 88:E39-E47.
Samuelson, T.W. (2011). "Randomized evaluation of the trabecular micro-bypass stent with phacoemulsification in patients with glaucoma and cataract," Ophthalmol. 118:459-467.
Schwartz, K.S. et al. (2006). "Glaucoma drainage implants: A critical comparison of types," Curr. Opin. Ophthalmol. 17:181-189.
Sidoti, P.A. et al. (1994). "Glaucoma drainage implants," Curr. Opin. Ophthalmol. 11:85-98.
Stefansson, J. (1925). "American journal of ophthalmology," vol. 8, pp. 681-693.
Summary of Safety and Effectiveness Data, STAARVISC™ (sodium hyaluronate) Premarket Approval Application (PMA) No. P000046, Apr. 18, 2001, 11 total pages.
Stegmann, R. et al. (1999). "Viscocanalostomy for Open-Angle Glaucoma in Black African Patients," Journal of Cataract & Refractive Surgery 25:316-322.
Stegmann, R. (2002). Robert Stegmann, MD: taking on the challenges of ocular trauma and disease, Ocular Surgery News, located

(56) References Cited

OTHER PUBLICATIONS at https://www.healio.com/news/ophthalmology/20120331/robert-stegmann-md-taking-on-the-challenges-of-ocular-trauma-and-disease, 4 total pages.
Wild, G.J. et al. (2001). "Dilation of Schlemm's Canal in Viscocanalostomy: Comparison of 2 Viscoelastic Substances," Journal of Cataract and Refractive Surgery 27:1294-1297.
Written Opinion dated Nov. 30, 2007, for PCT Application No. PCT/US2007/013038, filed May 31, 2007, 6 pages.
Written Opinion dated Apr. 5, 2011, for PCT Application No. PCT/US2011/023643, filed Feb. 3, 2011, 5 pages.
Written Opinion dated Feb. 1, 2013, for PCT Application No. PCT/US2012/058751, filed Oct. 4, 2012, 6 pages.
Written Opinion dated Sep. 14, 2015, for PCT Application No. PCT/US15/23720, filed Mar. 31, 2015, 8 pages.
Written Opinion of the International Searching Authority dated Nov. 2, 2022, for PCT Application No. PCT/US2022/031457, filed May 27, 2022, 11 pages.
Yablonski, M.E. (2005). "Trabeculectomy with internal tube shunt—A novel glaucoma surgery," J. Glaucoma 14:91-97.
Zhou, J. et al. (2006). "Trabecular bypass—Effect of Schlemm canal and collector channel dilation," J. Glaucoma 15:446-455.
Final Office Action dated Oct. 10, 2023, for U.S. Appl. No. 18/130,353, filed Apr. 3, 2023, 15 pages.
Final Office Action dated Oct. 10, 2023, for U.S. Appl. No. 18/130,354, filed Apr. 3, 2023, 16 pages.
Non-Final Office Action dated Oct. 18, 2023, for U.S. Appl. No. 18/197,679, filed May 15, 2023, 23 pages.

\* cited by examiner

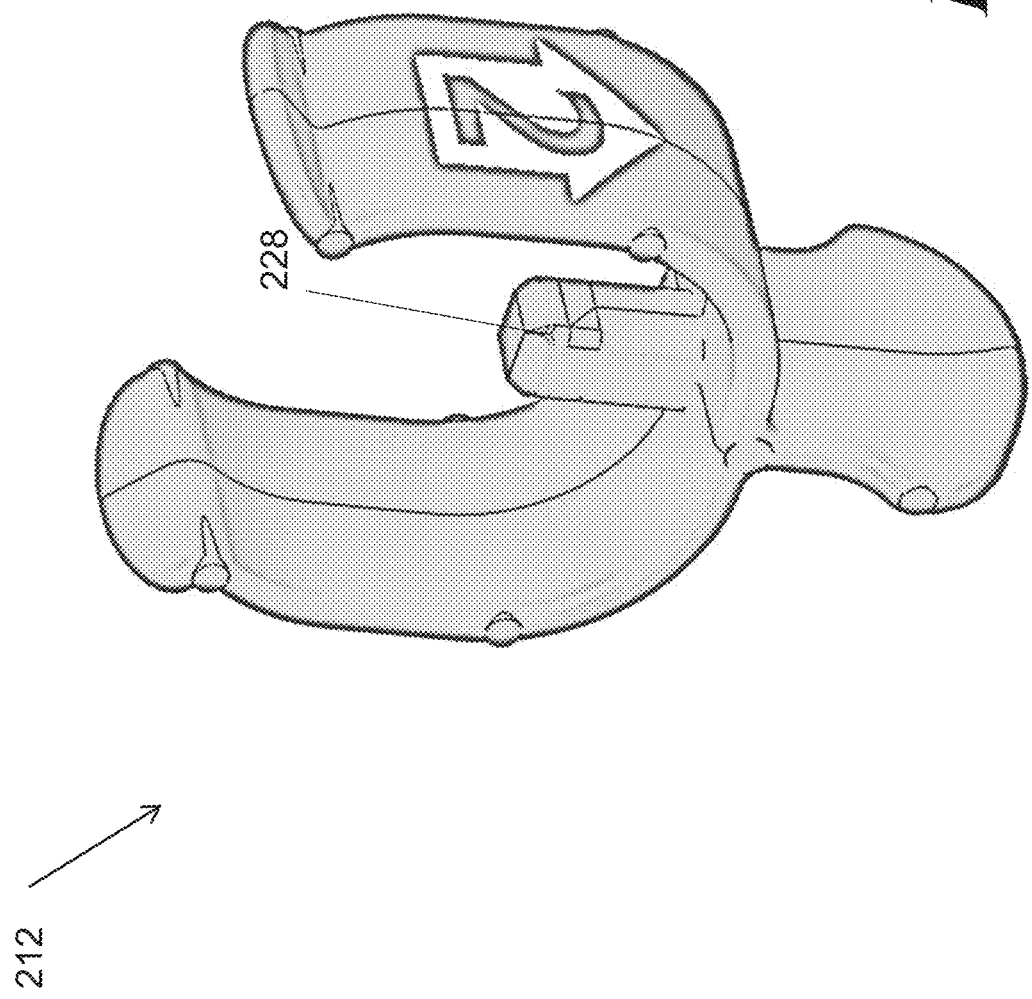

OCULAR DELIVERY SYSTEMS AND METHODS

CROSS-REFERENCE TO RELATED APPLICATIONS

This application is a continuation of U.S. patent application Ser. No. 17/033,408, filed on Sep. 25, 2020, now issued as U.S. Pat. No. 11,504,270, which claims priority to U.S. Provisional Application No. 62/907,474, filed on Sep. 27, 2019, each of which is hereby incorporated by reference in its entirety.

FIELD

Described here are systems and methods for accessing Schlemm's canal in an eye, delivering a fluid composition therein, and performing a trabeculotomy. The fluid composition may be a viscoelastic fluid that is delivered into the canal or aqueous collector channels to facilitate drainage of aqueous humor by dilating the canal, disrupting juxtacanalicular meshwork and the adjacent wall of Schlemm's canal, and/or increasing aqueous permeability through the trabeculocanalicular, or transmural, outflow pathway. The trabeculotomy may be performed by tearing the trabecular meshwork with an elongate member.

BACKGROUND

Glaucoma is a potentially blinding disease that affects over 60 million people worldwide, or about 1-2% of the population. Typically, glaucoma is characterized by elevated intraocular pressure. Increased pressure in the eye can cause irreversible damage to the optic nerve which can lead to loss of vision and even progress to blindness if left untreated. Consistent reduction of intraocular pressure can slow down or stop progressive loss of vision associated with glaucoma.

Increased intraocular pressure is generally caused by sub-optimal efflux or drainage of fluid (aqueous humor) from the eye. Aqueous humor or fluid is a clear, colorless fluid that is continuously replenished in the eye. Aqueous humor is produced by the ciliary body, and then ultimately exits the eye primarily through the trabecular meshwork. The trabecular meshwork extends circumferentially around the eye at the anterior chamber angle, or drainage angle, which is formed at the intersection between the peripheral iris or iris root, the anterior sclera or scleral spur and the peripheral cornea. The trabecular meshwork feeds outwardly into Schlemm's canal, a narrow circumferential passageway generally surrounding the exterior border of the trabecular meshwork. Positioned around and radially extending from Schlemm's canal are aqueous veins or collector channels that receive drained fluid. The net drainage or efflux of aqueous humor can be reduced as a result of decreased facility of outflow, decreased outflow through the trabecular meshwork and canal of Schlemm drainage apparatus, increased episcleral venous pressure, or possibly, increased production of aqueous humor. Flow out of the eye can also be restricted by blockages or constriction in the trabecular meshwork and/or Schlemm's canal and its collector channels.

Glaucoma, pre-glaucoma, and ocular hypertension currently can be treated by reducing intraocular pressure using one or more modalities, including medication, incisional surgery, laser surgery, cryosurgery, and other forms of surgery. In general, medications or medical therapy are the first lines of therapy. If medical therapy is not sufficiently effective, more invasive surgical treatments may be used. For example, a standard incisional surgical procedure to reduce intraocular pressure is trabeculectomy, or filtration surgery. This procedure involves creating a new drainage site for aqueous humor. Instead of naturally draining through the trabecular meshwork, a new drainage pathway is created by removing a portion of sclera and trabecular meshwork at the drainage angle. This creates an opening or passage between the anterior chamber and the subconjunctival space that is drained by conjunctival blood vessels and lymphatics. The new opening may be covered with sclera and/or conjunctiva to create a new reservoir called a bleb into which aqueous humor can drain. However, traditional trabeculectomy procedures carry both short and long term risks. These risks include blockage of the surgically-created opening through scarring or other mechanisms, hypotony or abnormally low intraocular pressure, expulsive hemorrhage, hyphema, intraocular infection or endophthalmitis, shallow anterior chamber angle, macular hypotony, choroidal exudation, suprachoroidal hemorrhage, and others.

One alternative is to implant a device in Schlemm's canal that maintains the patency of the canal or aids flow of aqueous humor from the anterior chamber into the canal. Various stents, shunts, catheters, and procedures have been devised for this purpose and employ an ab-externo (from the outside of the eye) approach to deliver the implant or catheter into Schlemm's canal. This method of placement is invasive and typically prolonged, requiring the creation of tissue flaps and deep dissections to access the canal. Additionally, it is very difficult for many surgeons to find and access Schlemm's canal from this external incisional approach because Schlemm's canal has a small diameter, e.g., approximately 50 to 250 microns in cross-sectional diameter, and it may be even smaller when collapsed. One such procedure, ab-externo canaloplasty, involves making a deep scleral incision and flap, finding and unroofing Schlemm's canal, circumnavigating all 360 degrees of the canal with a catheter from the outside of the eye, and either employing viscoelastic, a circumferential tensioning suture, or both to help maintain patency of the canal. The procedure is quite challenging and can take anywhere from forty-five minutes to two hours. The long-term safety and efficacy of canaloplasty is very promising, but the procedure remains surgically challenging and invasive.

Another alternative is viscocanalostomy, which involves the injection of a viscoelastic solution into Schlemm's canal to dilate the canal and associated collector channels. Dilation of the canal and collector channels in this manner generally facilitates drainage of aqueous humor from the anterior chamber through the trabecular meshwork and Schlemm's canal, and out through the natural trabeculocanalicular outflow pathway. Viscocanalostomy is similar to canaloplasty (both are invasive and ab-externo), except that viscocanalostomy does not involve a suture and does not restore all 360 degrees of outflow facility. Some advantages of viscocanalostomy are that sudden drops in intraocular pressure, hyphema, hypotony, and flat anterior chambers may be avoided. The risk of cataract formation and infection may also be minimized because of reduced intraocular manipulation and the absence of full eye wall penetration, anterior chamber opening and shallowing, and iridectomy. A further advantage of viscocanalostomy is that the procedure restores the physiologic outflow pathway, thus avoiding the need for external filtration, and its associated short and long term risks, in the majority of eyes. This makes the success of the procedure partly independent of conjunctival or episcleral scarring, which is a leading cause of failure in traditional trabeculectomy procedures. Moreover, the absence of an elevated filtering bleb avoids related ocular discomfort and potentially devastating ocular infections, and the procedure can be carried out in any quadrant of the outflow pathway.

However, current viscocanalostomy and canaloplasty techniques are still very invasive because access to Schlemm's canal must be created by making a deep incision into the sclera, creating a scleral flap, and un-roofing Schlemm's canal. In their current forms, these procedures are both "ab-externo" procedures. "Ab-externo" generally means "from the outside" and it is inherently more invasive given the location of Schlemm's canal and the amount of tissue disruption required to access it from the outside. On the other hand, "ab-interno" means "from the inside" and is a less invasive approach because of the reduced amount of tissue disruption required to access it from the inside. Consequently, an ab-interno approach to Schlemm's canal offers the surgeon easier access to the canal, but also reduces risk to the patient's eye and reduces patient morbidity. All of these lead to improved patient recovery and rehabilitation. The ab-externo viscocanalostomy and canaloplasty procedures also remain challenging to surgeons, because as previously stated, it is difficult to find and access Schlemm's canal from the outside using a deep incisional approach due to the small diameter of Schlemm's canal. A further drawback still is that at most, viscocanalostomy typically dilates up to 60 degrees of Schlemm's canal, which is a 360 degree ring-shaped outflow vessel-like structure. The more of the canal that can be dilated, the more total aqueous outflow can be restored.

Accordingly, it would be beneficial to have systems that easily and atraumatically provide access to Schlemm's canal using an ab-interno approach for the delivery of tools and compositions. It would also be useful to have systems that deliver tools and compositions into Schlemm's canal expeditiously to decrease procedure time and the risk of infection without compromising safety and precision of the delivery procedure. It would also be useful to have systems that deliver tools and fluid compositions into Schlemm's canal using an ab-interno approach so that cataract surgery and glaucoma surgery can both be accomplished during the same surgical sitting using the very same corneal or scleral incision. Such incisions are smaller and allow for less invasive surgery and more rapid patient recovery. This approach allows for accessing Schlemm's canal through the trabecular meshwork from the inside of the eye, and thus it is called "ab-interno." Methods of delivering tools and compositions that effectively disrupt the juxtacanalicular meshwork and adjacent wall of Schlemm's canal, also known as the inner wall of Schlemm's canal, maintain the patency of Schlemm's canal, increase outflow, decrease resistance to outflow, or effectively dilate the canal and/or its collector channels using the systems in a minimally invasive, ab-interno manner would also be desirable.

BRIEF SUMMARY

Described here are systems and methods for ab interno fluid delivery to Schlemm's canal and for trabeculotomy. In one variation, the system for use in the eye may comprise an elongate member comprising a lumen, wherein the elongate member is slidable between a retracted position and an extended position, a reservoir comprising a fluid composition, wherein the reservoir is fluidly connected to the lumen of the elongate member, a linear gear, and a linkage coupling the reservoir and the linear gear. The linear gear may comprise a first set of teeth configured to engage the linkage when the system is in a first configuration, and a second set of teeth configured to engage the linkage when the system is in a second configuration. The first set of teeth may allow movement of the linear gear relative to the linkage in a first direction and prevent movement of the linear gear relative to the linkage in a second direction opposite the first direction. The second set of teeth may allow movement of the linear gear relative to the linkage in the first and second directions.

In some variations, the first set of teeth may be located in a proximal portion of the linear gear, and the second set of teeth may be located in a distal portion of the linear gear. In some variations, the teeth in the first set of teeth are larger than the teeth in the second set of teeth. In some instances, the linkage may be fixedly coupled to the reservoir. In some instances, the first and second sets of teeth may be configured to provide haptic feedback when the linear gear and linkage are moved relative to each other. In some variations, the second set of teeth may be configured to resist distal movement of the linear gear relative to the linkage in response to fluid pressure in the reservoir.

In some variations, in the first configuration, the linear gear may be movable proximally but not distally relative to the linkage, and in the second configuration, the linear gear may be movable proximally and distally relative to the linkage. In some instances, in the first configuration, the linear gear may be movable toward but not away from the reservoir, and in the second configuration, the linear gear may be movable toward and away from the reservoir.

In some variations, the linkage may comprise a flexible portion. In some of these variations, the flexible portion may be configured to flex in a first plane around the second set of teeth when the linear gear moves distally relative to the linkage, and the flexible portion may be configured to flex in a second plane around the second set of teeth when the linear gear moves proximally relative to the linkage. In some of these variations, the first and second planes may be perpendicular. In some of these variations, the flexible portion may comprise a u-shaped bend.

In another variation, a system for use in the eye may comprise an elongate member comprising a lumen, wherein the elongate member is slidable between a retracted position and an extended position, a reservoir comprising a fluid composition, wherein the reservoir is fluidly connected to the lumen of the elongate member, a linear gear, and a linkage coupling the reservoir and the linear gear, wherein the linkage comprises a flexible portion configured to flex in two perpendicular planes.

In some variations, the flexible portion of the linkage may comprise a u-shaped bend. In some instances, the flexible portion may comprise a notch configured to engage the linear gear. In some variations, the linear gear may comprise a first set of teeth and a second set of teeth. In some of these variations, the first set of teeth may be proximal to the second set of teeth. In some of these variations, the first set of teeth may be configured to allow the notch to translate in one direction relative to the linear gear, and the second set of teeth may be configured to allow the notch to translate in two directions relative to the linear gear. In some of these variations, the first set of teeth may allow the notch to translate distally but not proximally relative to the linear gear, and the second set of teeth may allow the notch to translate distally and proximally relative to the linear gear. In some variations, the notch may be configured to generate a proximal force on the second set of teeth that opposes a distal force on the linear gear generated by the fluid composition.

In another variation, the system for use in the eye comprises an elongate member comprising a lumen, wherein the elongate member is slidable between a retracted position and an extended position, a reservoir comprising a fluid composition, wherein the reservoir is fluidly connected to the lumen of the elongate member, and a drive assembly having a first configuration and a second configuration, wherein in the first configuration the drive assembly is configured to simultaneously move the elongate member from the extended position to the retracted position and deliver the fluid composition from the reservoir through the lumen of the flexible elongate member, and wherein in the second configuration the drive assembly is configured to move the elongate member from the extended position to the retracted position without delivering fluid composition from the reservoir.

In some variations, the drive assembly switches from the first configuration to the second configuration automatically. For example, the drive assembly switches from the first configuration to the second configuration after a predetermined cumulative retraction of the elongate member.

The system may further comprise a linkage coupling the drive assembly and the reservoir. The drive assembly may comprise a linear gear, and the linkage may be slidably coupled to the linear gear and fixedly coupled to the reservoir. In some variations, the drive assembly is in the first configuration when the linear gear is coupled to a proximal portion of the linear gear, and the drive assembly is in the second configuration when the linear gear is coupled to a distal portion of the linear gear. In the first configuration, the linkage may be slidable distally but not proximally relative to the linear gear, and in the second configuration, the linkage may be slidable distally and proximally relative to the linear gear. In the first configuration, the drive assembly may be movable toward but not away from the reservoir, and in the second configuration, the drive assembly may be movable toward and away from the reservoir.

The proximal portion of the linear gear may comprise a proximal set of teeth. The proximal set of teeth may be configured to allow the linkage to slide distally but not proximally relative to the linear gear. The distal portion of the linkage may comprise a distal set of teeth that allow the linkage to slide distally and proximally relative to the linear gear. The distal set of teeth may resist distal movement of the linkage relative to the linear gear in response to fluid pressure in the reservoir. The linkage may comprise a flexible portion that can interface with the proximal set of teeth or distal set of teeth (depending on the relative position of the linkage and linear gear). The flexible portion may flex in one plane around the distal set of teeth when the linkage is moving distally relative to the linear gear, and in a second, different plane around the distal set of teeth when the linkage is moving proximally relative to the linear gear. The distal set of teeth may be smaller than the proximal set of teeth.

In some variations, the methods comprise delivering a fluid composition to Schlemm's canal and performing a trabeculotomy via an ab interno approach using a single device that automatically switches from a fluid-delivery configuration to a trabeculotomy configuration. The methods may comprise treating one or more conditions of the eye by accessing Schlemm's canal with a cannula via an ab interno approach, advancing an elongate member out of the cannula and along Schlemm's canal, and retracting the elongate member, wherein retracting the elongate member causes a fluid composition to be simultaneously and automatically delivered out of the elongate member. The methods may further comprise advancing the elongate member along Schlemm's canal and retracting the elongate member, wherein retracting the elongate member does not cause a fluid composition to be delivered out of the elongate member. The methods may use only a single access point in Schlemm's canal.

BRIEF DESCRIPTION OF THE DRAWINGS

FIGS. 2A-2I depict an exemplary delivery device. FIG. 2A is a perspective view of the exemplary delivery device. FIG. 2B shows a cutaway view of the delivery device. FIGS. 2C-2E show perspective views of the delivery device with one side of the housing removed. In FIG. 2D, the linkage is also removed in order to show the plunger. FIG. 2F shows a close-up cutaway view of the distal end of the delivery device. FIG. 2G is a perspective view of the distal end of the delivery device and the elongate member in an extended position. FIG. 2H shows the linear gear of the delivery device. FIG. 2I shows the lock of the delivery device.

DETAILED DESCRIPTION

Described here are systems and methods for accessing Schlemm's canal and for delivering a fluid composition therein and for tearing the trabecular meshwork to reduce intraocular pressure and thereby treat conditions of the eye. The fluids and certain components of the system, e.g., the slidable elongate member, may be used to provide a force for disrupting trabeculocanalicular tissues, which include the trabecular meshwork, juxtacanalicular tissue, Schlemm's canal, and the collector channels. As used herein, the term "disrupting" refers to the delivery of a volume of fluid or a system component that alters the tissue in a manner that improves flow through the trabeculocanalicular outflow pathway. Examples of tissue disruption include, but are not limited to, dilation of Schlemm's canal, dilation of collector channels, increasing the porosity of the trabecular meshwork, stretching the trabecular meshwork, forming microtears or perforations in juxtacanalicular tissue, removing septae from Schlemm's canal, cutting, tearing, or removal of trabeculocanalicular tissues, or a combination thereof.

Figure 1:
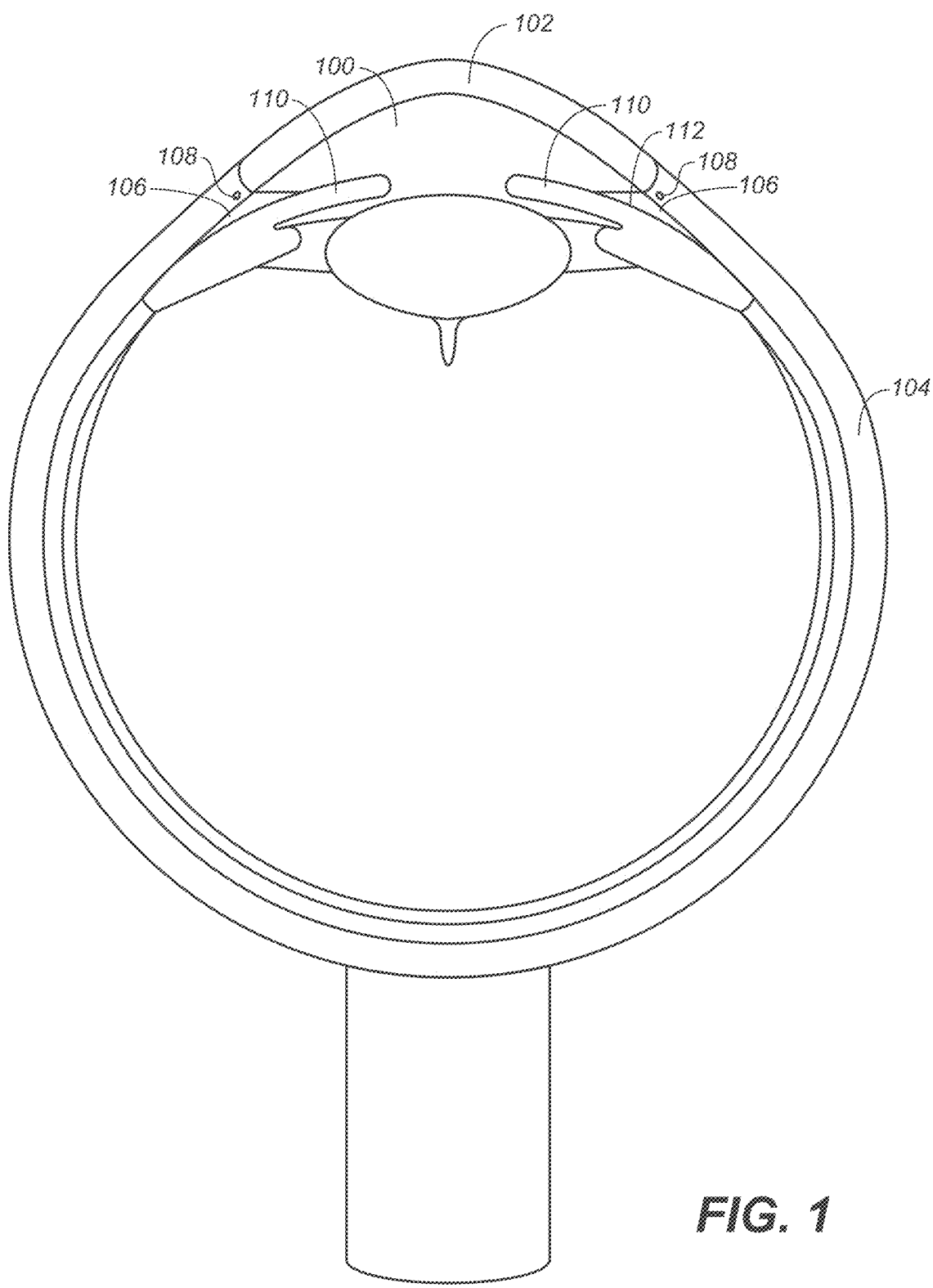
FIG. 1 shows a stylized, cross-sectional view of the eye and some of the structures involved in the flow of aqueous humor out of the eye.

To better understand the systems and methods described here, it may be useful to explain some of the basic eye anatomy. FIG. 1 is a stylized depiction of a normal human eye. The anterior chamber (100) is shown as bounded on its anterior surface by the cornea (102). The cornea (102) is connected on its periphery to the sclera (104), which is a tough fibrous tissue forming the protective white shell of the eye. Trabecular meshwork (106) is located on the outer periphery of the anterior chamber (100). The trabecular meshwork (106) extends 360 degrees circumferentially around the anterior chamber (100). Located on the outer peripheral surface of the trabecular meshwork (106) is Schlemm's canal (108). Schlemm's canal (108) extends 360 degrees circumferentially around the meshwork (106). At the apex formed between the iris (110), meshwork (106), and sclera (104), is the anterior chamber angle (112).

The systems are generally configured for single-handed manipulation and for control by a single operator, and include one or more features useful for easily accessing Schlemm's canal with minimal trauma. Once access to the canal has been obtained, the system may deliver a fluid composition and tear the trabecular meshwork. The lumen of the elongate member may be configured to deliver a fluid composition to the canal, and the body of the elongate member may be configured to cut or tear through the trabecular meshwork if the system is removed from the eye while the elongate member is within Schlemm's canal.

It should be appreciated that in some instances the delivery systems described herein may be used only to deliver a fluid composition to Schlemm's canal (and not to tear the trabecular meshwork), or may be used only to tear the trabecular meshwork (and not to deliver a fluid composition).

In some variations the methods described herein may comprise implanting a device completely or partially into Schlemm's canal in conjunction with delivering a fluid composition into the canal and/or tearing the trabecular meshwork. When a device is implanted into the canal, it will generally be configured to maintain the patency of Schlemm's canal without substantially interfering with transmural fluid flow across the canal. This may restore, enable, or enhance normal physiologic efflux of aqueous humor through the trabeculocanalicular tissues. Ocular implants such as those disclosed in U.S. Pat. No. 7,909,789, and such as those disclosed in U.S. Pat. No. 8,529,622, each of which is hereby incorporated by reference in its entirety, may be delivered. In some variations, the implants in U.S. Pat. No. 7,909,789 and U.S. Pat. No. 8,529,622 include a support having a least one fenestration that completely traverses a central core of Schlemm's canal without substantially interfering with transmural fluid flow or longitudinal fluid flow across or along the canal. The ocular device may also disrupt the juxtacanalicular trabecular meshwork or adjacent inner wall of Schlemm's canal. The ocular devices may also be coated with a drug useful for treating ocular hypertension, glaucoma, or pre-glaucoma, infection, or scarring, neovascularization, fibrosis, or inflammation postoperatively. The ocular device may also be formed to be solid, semi-solid, or bioabsorbable.

I. SYSTEMS/DEVICES

The systems described herein may be single-handed, single-operator controlled devices that generally include a universal handle having a grip portion and a housing that has an interior and a distal end. A cannula is typically coupled to and extends from the housing distal end. The cannula may include a proximal end and a distal curved portion, where the distal curved portion has a proximal end and a distal end, and a radius of curvature defined between the ends. In other variations, the cannula may be straight and may not comprise a distal curved portion. The cannula may also be configured to include a body; a distal tip having a bevel; and a lumen extending from the proximal end through the distal tip. The bevel may directly engage the distal end of the curved portion of the cannula (i.e., the bevel may directly engage the radius of curvature).

The systems may also generally include a drive assembly partially contained within the housing comprising gears that translate rotational movement to linear movement. The system may also be configured to include a slidable elongate member comprising a lumen that is coaxially disposed within the cannula lumen. The system may also be configured to include a fluid assembly in the handle. Fluid compositions such as saline, viscoelastic fluids, including viscoelastic solutions, air, and gas may be delivered using the system. Suitable markings, colorings, or indicators may be included on any portion of the system to help identify the location or position of the distal end of the cannula and/or the slidable elongate member.

In some instances, the systems described herein may be used to perform ab-interno trabeculotomy, ab-interno transluminal trabeculotomy, clear corneal trabeculotomy, clear corneal transluminal trabeculotomy, ab-interno canaloplasty, and/or clear corneal canaloplasty, and may be used to deliver a fluid composition into the anterior or posterior segment of the eye.

Figure 2A:
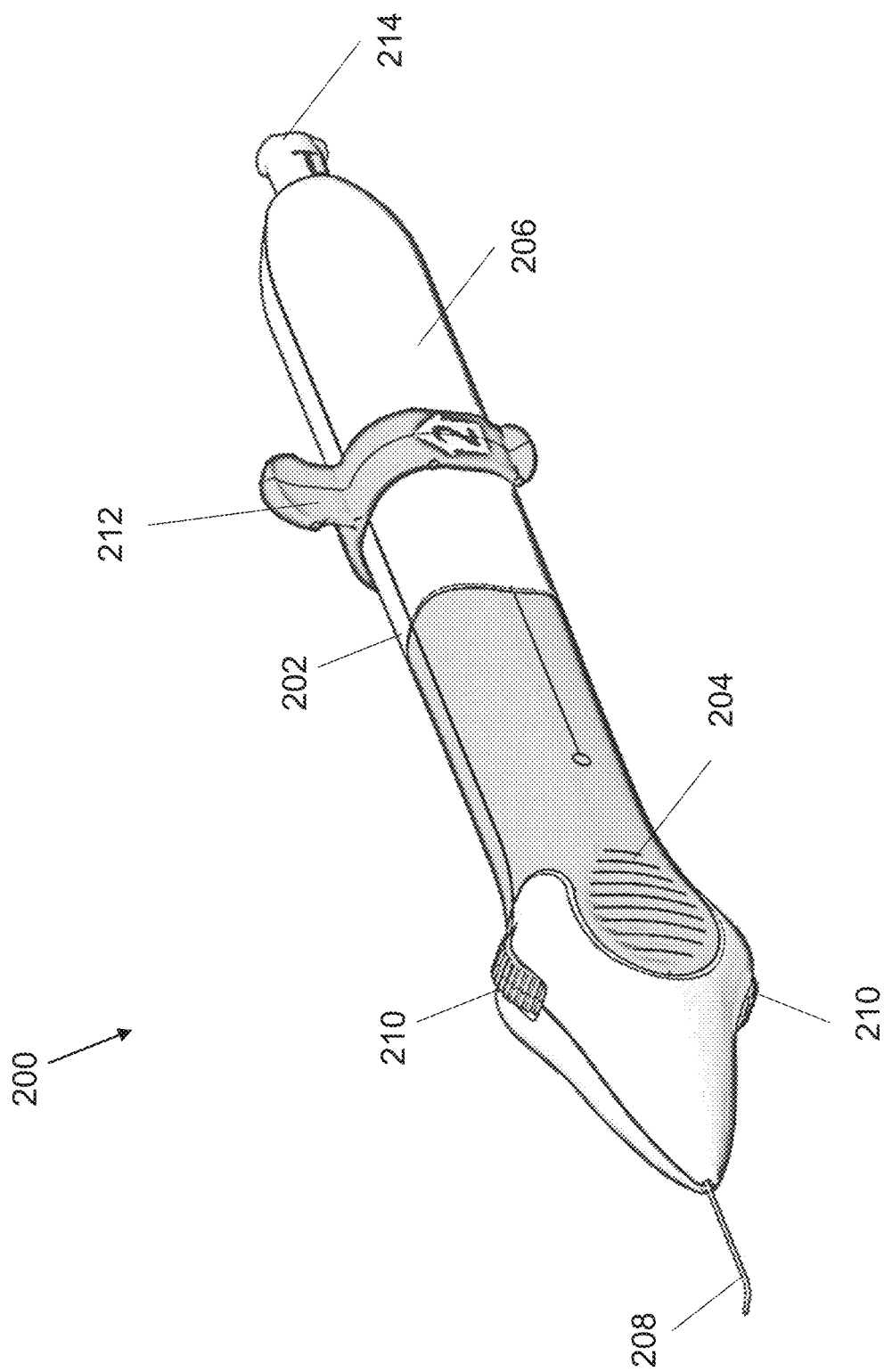

An exemplary delivery system is depicted in FIG. 2A. Delivery system (200) includes a universal handle (202) having a grip portion (204) and a housing (206). The housing (206) has a proximal end and a distal end. A cannula (208) is coupled to and extends from the housing's distal end. A drive assembly is substantially contained within the housing (206), which actuates movement of an elongate member (not shown) through rotation of one wheel (210) (two of which extend out of the housing (206) on opposite sides). The delivery system (200) may further comprise a lock (212) and a reservoir comprising a proximal opening (214). The delivery system (200) is described in more detail herein.

The delivery systems described herein may in some variations be fully disposable. In other variations, a portion of the delivery system may be reusable (e.g., non-patient contact materials, such as the handle), while a portion of the delivery system may be disposable (e.g., patient-contact materials, such as the cannula and elongate member). In yet other variations, the delivery systems described herein may be fully reusable.

Universal Handle

The delivery systems described herein may include a universal handle capable of single-handed use. For example, the handle may be configured to be capable for use with the left or right hand, for use on the left or right eye, or in the clockwise or counterclockwise direction. That is, the handle may be configured such that the ability to use the delivery system is independent of which hand is used, which eye a procedure is performed on, or which direction around the canal a tool or fluid composition is delivered. For example, the delivery system may be used to deliver a fluid composition in a clockwise direction in an eye, and then with a simple flip of the handle (or by rotating the cannula itself 180 degrees in another variation) to a second orientation, may be used to deliver a fluid composition in the counterclockwise direction. However, it should be appreciated that in other variations, the delivery systems described herein may be configured to be used in a particular configuration (e.g., with a single side up, only in a clockwise direction, only in a counterclockwise direction, etc.).

The handle generally includes a grip portion and a housing. The grip portion may be raised, depressed, or grooved in certain areas, or textured to improve hold of the handle by the user or to improve comfort of the user. The housing may include an interior portion and a distal end. The interior portion of the housing may contain a drive assembly and a positioning element (both further described below). In some variations, the distal end of the housing may include a fluid port that can provide fluids for irrigation of the operative field or to purge air from the system.

The universal handle may be made from any suitable material, including without limitation, fluoropolymers; thermoplastics such as polyetheretherketone, polyethylene, polyethylene terephthalate, polyurethane, nylon, and the like; and silicone. In some variations, the housing or portions thereof may be made from transparent materials. Materials with suitable transparency are typically polymers such as acrylic copolymers, acrylonitrile butadiene styrene (ABS), polycarbonate, polystyrene, polyvinyl chloride (PVC), polyethylene terephthalate glycol (PETG), and styrene acrylonitrile (SAN). Acrylic copolymers that may be particular useful include, but are not limited to, polymethyl methacrylate (PMMA) copolymer and styrene methyl methacrylate (SMMA) copolymer (e.g., Zylar 631® acrylic copolymer). In variations in which the universal handle is reusable, the handle may be made from a material that can be sterilized (e.g., via autoclaving), such as a heat-resistant metal (e.g., stainless steel, aluminum, titanium).

The length of the universal handle may generally be between about 1 inch (2.5 cm) to about 20 inches (50.8 cm). In some variations, the length of the universal handle may be between about 4 inches (10.2 cm) and 10 inches (25.4 cm). In some variations, the length of the universal handle is about 7 inches (17.8 cm).

Cannula

The cannula of the delivery system is typically coupled to and extends from the housing distal end, and is generally configured to provide easy and minimally traumatic access to Schlemm's canal using a minimally invasive ab-interno approach. The cannula may be fixedly attached to the distal end of the housing, or in other variations it may be rotatably attached to the distal end of the housing. In variations of the delivery systems where the handle is reusable and the cannula is disposable, the cannula may be removably attached to the distal end of the housing. Some variations of the cannula may include a proximal end and a distal curved portion, where the distal curved portion has a proximal end and a distal end, and a radius of curvature defined between the ends. However, it should be appreciated that in other variations the cannula may be straight and may not comprise a distal curved portion. The cannula may also be configured to include a body; a distal tip having a bevel and a sharpened piercing tip; and a lumen extending from the proximal end through the distal tip. When the cannula comprises a distal curved portion, the bevel may directly engage the distal end of the curved portion of the cannula (i.e., the bevel may directly engage the radius of curvature). In some variations, the sharpened piercing tip may comprise one or more angled surfaces, as is described in more detail below.

The cannula may be made from any suitable material with sufficient stiffness to allow it to be advanced through the anterior chamber and into Schlemm's canal. For example, the cannula may be formed of a metal such as stainless steel, nickel, titanium, aluminum, or alloys thereof (e.g., Nitinol metal alloy), a polymer, or a composite. Exemplary polymers include without limitation, polycarbonate, polyetheretherketone (PEEK), polyethylene, polypropylene, polyimide, polyamide, polysulfone, polyether block amide (PEBAX), and fluoropolymers. In some instances, it may be advantageous to coat the cannula with a lubricious polymer to reduce friction between the ocular tissue and the cannula during the procedure. Lubricious polymers include, without limitation, polyvinyl alcohol, polyethylene glycol, polyvinyl pyrrolidone, fluorinated polymers (including polytetrafluoroethylene (PTFE or Teflon®)), and polyethylene oxide. In variations in which the cannula is reusable, the cannula may be made from a material that can be sterilized (e.g., via autoclaving), such as a heat-resistant metal (e.g., stainless steel, aluminum, titanium).

The cannula generally has an outer diameter sized to gain access to the lumen of Schlemm's canal while minimally obstructing the surgeon's view. Accordingly, the outer diameter may range from about 50 microns to about 1000 microns. In some variations, the outer diameter may range from about 150 microns to about 800 microns. The cannula also has an inner diameter, which may range from about 50 microns to about 400 microns. The cannula may also be formed to have any suitable cross-sectional profile, e.g., circular, elliptical, triangular, square, rectangular, etc.

The cannula may be configured to include multiple portions or parts. A cannula having a body, a distal curved portion having a proximal end and a distal end, a radius of curvature defined between the ends, and a bevel at the distal tip of the cannula that directly engages the distal end of the curved portion of the cannula may be particularly useful for accessing the lumen of Schlemm's canal. Here the body (straight portion of the cannula) may have a length ranging from about 5 mm to about 50 mm, about 10 mm to about 30 mm, or from about 14 mm to about 20 mm. In some variations, the body may have a length of about 18 mm. The distal curved portion of the cannula may be uniform in cross-sectional shape or it may taper closer to the distal end to facilitate entry into Schlemm's canal. The radius of curvature of the distal curved portion may be adapted to facilitate tangential entry, as well as precise and minimally traumatic entry into Schlemm's canal, and may range from about 1 mm to about 10 mm or from about 2 mm to about 5 mm. In one variation, the radius of curvature is about 2.5 mm. The cannula may also have an angular span suitable for facilitating entry into Schlemm's canal, and may range from about 70 degrees to about 170 degrees, or about 100 degrees to about 150 degrees. In one variation, the angular span is about 120 degrees.

The size, shape, geometry, and the like, of the bevel at the distal end of the curved portion of the cannula may be beneficial in allowing easy and minimally traumatic access to Schlemm's canal. In this respect, and as described in further detail below, having a bevel that directly engages the radius of curvature of the distal end of the cannula may be particularly useful.

In other variations, the cannula may include a short straight segment coupled to the distal end of the distal curved portion of the cannula (e.g., at the end of the radius of curvature). Here the bevel engages the straight segment and not the radius of curvature. The length of the straight segment may range from about 0.5 mm to about 5 mm. In some variations, the length of the straight segment ranges from about 0.5 mm to about 3 mm, or from about 0.5 mm to about 1 mm. The length of the straight segment may also be less than about 0.5 mm, e.g., it may be about 0.1 mm, about 0.2 mm, about 0.3 mm, or about 0.4 mm. In variations where the bevel directly engages the distal end of the curved portion of the cannula (i.e., the bevel directly engages the radius of curvature), the cannula lacks a straight segment (length of the straight segment is zero).

It may also be useful to have a bevel that is sharp and short. Exemplary bevel angles may range from about 10 degrees to about 90 degrees. In some instances, the bevel angle may range from about 10 degrees to about 50 degrees. In one variation, the bevel angle is about 35 degrees, while in another variation the bevel is about 25 degrees. The bevel may also be oriented in any suitable direction. For example, the bevel may be oriented so that it opens up towards the surgeon, or it may be reversed to open away from the surgeon or in any plane in between.

As is described in more detail below, in yet some variations, the cannula is configured to include one section that is sharp, and another section that is blunt (e.g., deburred). The dual surface configuration of such a cannula may be advantageous, since it may provide easier canal access by piercing the meshwork while also providing a gentle, dispersed force on the elongate member during elongate member retraction into the cannula to avoid cutting or breaking the elongate member due to retraction force.

Figure 4:
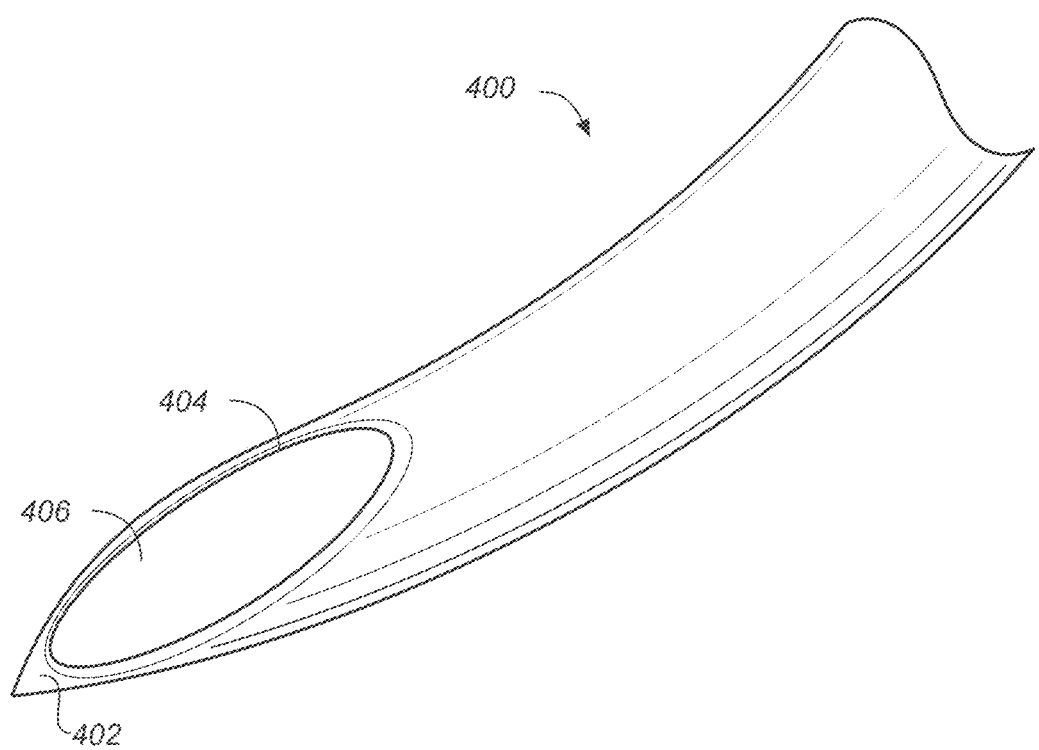
FIG. 4 depicts an exemplary cannula according to another variation.

For example, as shown in FIG. 4, the distal end of cannula (400) may have a sharpened piercing tip (402) and a smooth edge (404) that define portions of opening (406), through which a slidable elongate member (not shown) may be advanced and retracted. As is described in more detail with respect to FIGS. 5, 6A-6B, and 7, the sharp tip (402) may be formed by compounding multiple bevels, and the smooth edge (404) may be created by smoothing or deburring inner and/or outer circumferential edges of the distal tip. Additionally, in some embodiments, the internal and/or external surfaces of the elongate member adjacent to the opening (406) may also be smoothed. Methods of making the cannula are described in more detail below.

Figure 3:
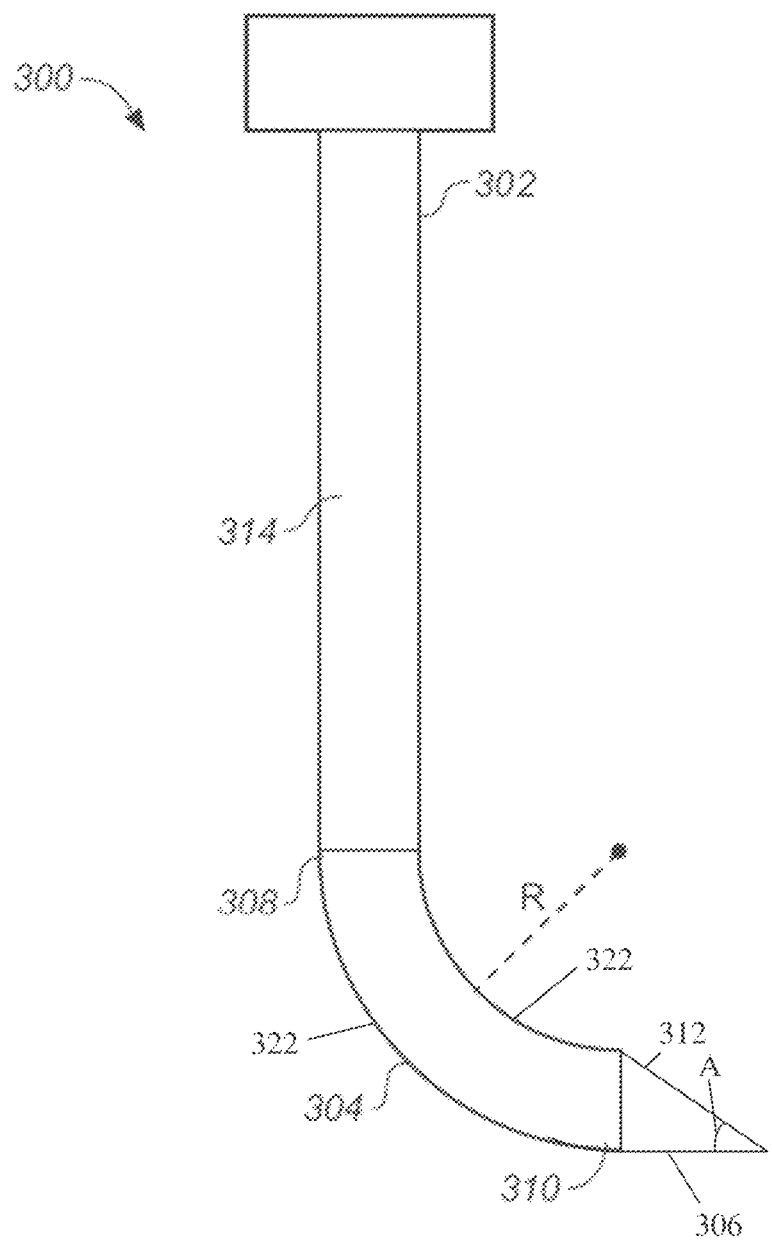
FIG. 3 depicts a side view of an exemplary cannula of the delivery system.

The cannula of an exemplary delivery system is shown in more detail in FIG. 3. Here the cannula (300) comprises a proximal end (302) a distal curved portion (304), a body (314), and a distal tip (306). The distal curved portion (304) has a proximal end (308) and a distal end (310), and a radius of curvature (R) that is defined between the ends (308, 310). The distal curved portion (304) also has an inner radius (320) defined by the surface of the cannula closest to the center of the radius of curvature (R), and an outer radius (322) defined by the surface of cannula further away from the center. A bevel (312) at the distal tip (306) directly engages the distal end of the curved portion of the cannula (310). In other words, the bevel (312) may be contiguous with the distal end of the curved portion of the cannula (310). As previously stated, this configuration of the distal curved portion (304) and bevel (312) may be beneficial or advantageous for allowing easy, atraumatic, and controlled access into Schlemm's canal. The angle of the bevel may also be important. In general, a short bevel may be beneficial. The bevel (312) may comprise an angle (A) between about 5 degrees and about 85 degrees. In some variations, the angle (A) may be about 5, 10, 15, 20, 25, 30, 35, 40, 45, 50, 55, 60, 65, 70, 75, 80, or 85 degrees. In some variations, the angle (A) may be between about 23 degrees and about 27 degrees. In the variation shown in FIG. 3, the bevel angle (A) is about 25 degrees.

Figure 5:
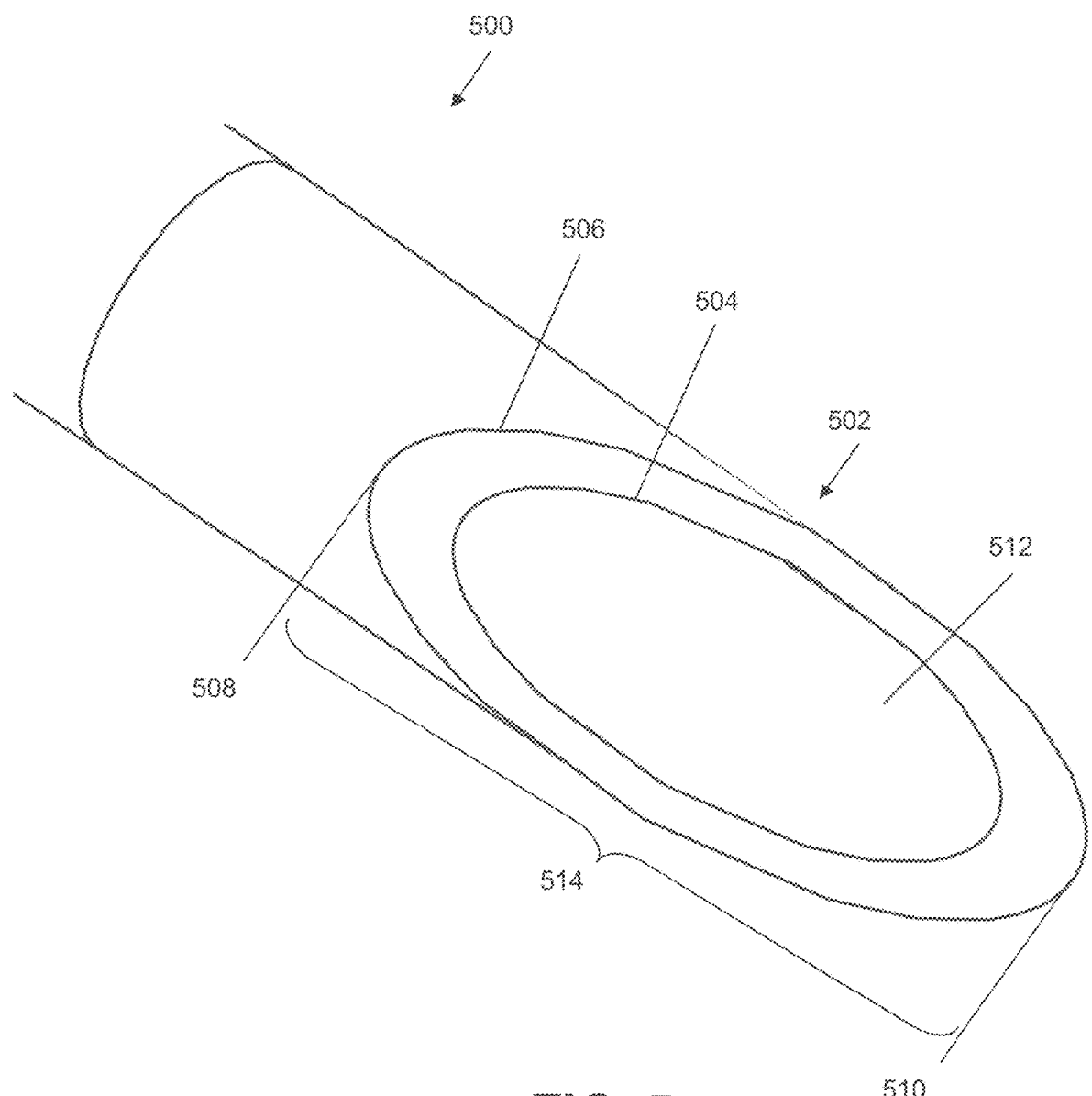
FIG. 5 is a perspective view of a variation of a distal tip of a cannula.

FIG. 5 depicts a perspective view of a distal tip (502) of a cannula (500) comprising a bevel (514). The distal tip (502) may be cut or ground at an angle to create the bevel (514). As shown, the beveled distal tip (502) comprises a proximal end (508), a distal end (510), and an elongated opening (512) having an elliptical, rather than a circular, shape. The distal tip (502) may comprise an elliptical shaped lumen opening that is angled such that the top of the elliptical opening is closer to the proximal portion of the cannula than the bottom of the elliptical opening. Also shown in FIG. 5 are inner and outer circumferential edges (504, 506).

Figure 6A:
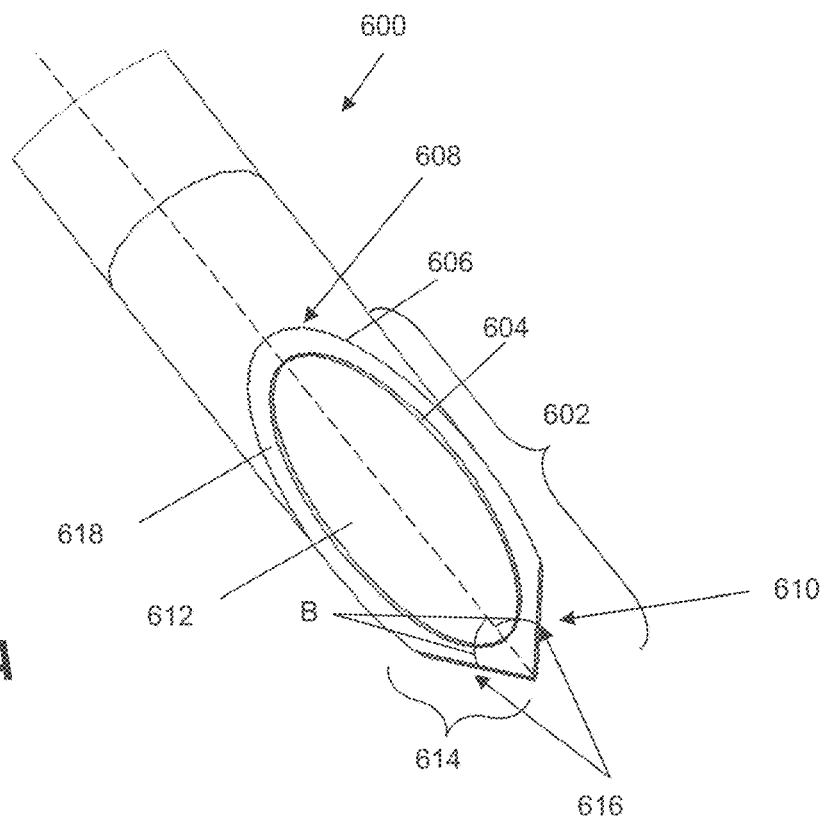
FIGS. 6A and 6B are perspective and front views, respectively, of a variation of a distal tip of a cannula.
Figure 6B:
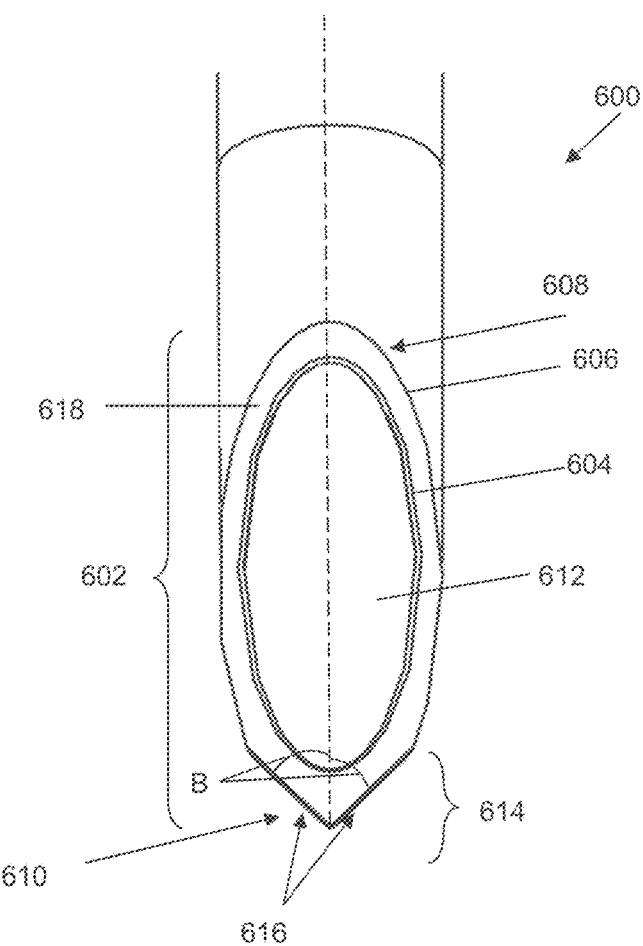

FIGS. 6A and 6B depict perspective and front views, respectively, of a variation of a distal tip (600) of a cannula comprising a bevel (602) and a sharpened piercing tip (614). As shown there, the distal tip (600) also comprises a proximal end (608), a distal end (610), inner and outer circumferential edges (604, 606), and a lumen opening (612). The sharpened piercing tip (614) may comprise two angled surfaces (616) that converge to form a sharp point. The angled surfaces (616) may have any suitable angle that results in a sharpened piercing tip (614). For example, in some instances, the angle surfaces (616) may have an angle (B) relative to the longitudinal axis of the distal tip (600) of about 20, 25, 30, 35, 40, 45, or 50 degrees, between about 25 and about 50 degrees, or between about 37.5 and about 42.5 degrees. In some instances, the angle (B) may be about 40 degrees. Accordingly, in some variations, the angle between the two angled surfaces (616) may be between about 50 and about 100 degrees, and in some instances, the angle between the two angled surfaces (616) may be about 80 degrees. It should be appreciated that although the distal tip (600) is depicted with two angled surfaces, a distal tip with a single angled surface may also be used.

Elongate Member

The delivery systems described herein may comprise a slidable elongate member coaxially disposed within the cannula lumen. The elongate member may comprise a lumen and be configured to deliver a fluid composition. However, it should be appreciated that in other variations, the elongate member may not comprise a lumen and/or may not be configured to deliver a fluid composition.

The elongate member may be coaxially disposed and slidable within the cannula lumen of the delivery systems described here. When the elongate member is in a retracted position relative to the cannula, the distal end of the elongate member may be located within (i.e., proximal to) the distal tip of the cannula. When the elongate member is in an extended position relative to the cannula, the distal end of the elongate member may be located outside of (i.e., distal to) the distal tip of the cannula. The length of extension of the elongate member beyond the distal tip of the cannula may correspond to the distance around Schlemm's canal that may be traversed by the elongate member (e.g., in order to disrupt Schlemm's canal and/or surrounding trabeculocanalicular tissues, and/or to deliver a fluid composition). When a variation of the delivery systems described herein is used to deliver a fluid composition, the length traversed by the elongate member may correspond to the length around Schlemm's canal to which the fluid composition is delivered. When a variation of the delivery systems described herein is used to tear or cut the trabecular meshwork, the length traversed by the elongate member may correspond to the length of trabecular meshwork that is cut or torn. In some variations, this length may be between about 1 mm and about 50 mm. In some of these variations, the length may be between about 10 mm and about 40 mm, between about 15 mm and about 25 mm, between about 16 mm and about 20 mm, between about 18 mm and about 20 mm, between about 19 mm and about 20 mm, between about 18 mm and about 22 mm, about 20 mm, between about 30 mm and about 50 mm, between about 35 mm and about 45 mm, between about 38 mm and about 40 mm, between about 39 mm and about 40 mm, or about 40 mm. The elongate member may be moved between extended and retracted positions using a drive assembly of the delivery system, described in more detail below.

The elongate member may be sized so that it can be advanced through the cannula and into a portion of Schlemm's canal (e.g., 0 to 360 degrees of the canal). This size may in some instances allow it to disrupt trabeculocanalicular tissues, stent, and/or apply tension to the canal, and/or to deliver a fluid composition. The elongate member may be made from any suitable material that imparts the desired flexibility and pushability for introduction through the eye wall, accessing Schlemm's canal, and/or navigation through other ocular tissue structures. For example, the elongate member may comprise a polymer (e.g., nylon, polypropylene); a polymer reinforced with metal wire, braid or coil; composites of polymers and metal; or metals such as stainless steel, titanium, shape-memory alloy (e.g., Nitinol), or alloys thereof. In variations in which the elongate member is reusable, the elongate member may be made from a material that can be sterilized (e.g., via autoclaving), such as a heat resistant metal (e.g., stainless steel, aluminum, titanium). The elongate member may be straight with enough flexibility and pushability to navigate the ring-shaped Schlemm's canal or may be pre-shaped to about a 2-10 mm radius of curvature or about a 6 mm radius of curvature (i.e., the approximate radius of curvature of Schlemm's canal in an adult human) to more easily circumnavigate Schlemm's canal, partially or in its entirety. In some variations, the elongate member may be configured to be advanced over or along a guidewire.

It may in some variations be desirable for the elongate member to have one or more features to improve visualization of the elongate member. For example, the elongate member may be colored (e.g., red, orange, yellow, green, blue, purple, etc.). Additionally or alternatively, visualization may be improved using an illuminated beacon, a fiber optic, side illuminating fiber optic, luminescence, fluorescence, or the like. For example, a fiber optic may travel along the body of the elongate member to deliver light to the distal tip of the elongate member, which may improve visualization of the distal tip of the elongate member as it is advanced or retracted about Schlemm's canal.

In some variations the elongate member may be sized to be advanced atraumatically through Schlemm's canal. In other variations, the elongate member may be sized to have an outer diameter sufficient to disrupt Schlemm's canal and surrounding trabeculocanalicular tissues. The outer diameter may range from about 25 microns to about 1000 microns, from about 25 microns to about 500 microns, from about 50 microns to about 500 microns, from about 150 microns to about 500 microns, from about 200 microns to about 500 microns, from about 300 microns to about 500 microns, from about 200 microns to about 250 microns, from about 150 microns to about 200 microns, or from about 180 microns to about 300 microns. In some instances it may be beneficial for the elongate member to have an outer diameter of about 240 microns.

In some variations, the distal end of the elongate member may be configured as a blunt bevel, an atraumatic tip, an enlarged atraumatic tip, or the like, to help the elongate member be advanced through Schlemm's canal. In some of these variations, the distal end may comprise a blunt parasol-shaped atraumatic tip. In other variations, a distal portion of the elongate member may optionally include a disruptive component, e.g., a notch, hook, barb, a rough surface, or combination thereof, to disrupt the juxtatrabecular portion of Schlemm's canal or juxtatrabecular meshwork. One or more projections emanating from the elongate member may further disrupt the juxtatrabecular portion of Schlemm's canal or juxtatrabecular meshwork and thus increase permeability of aqueous humor through the trabecular meshwork into Schlemm's canal. In some instances, the elongate member may also deliver energy to the trabeculocanalicular tissues (e.g., ultrasonic energy, radiofrequency energy (e.g., for electrocautery, electroablation), electromagnetic radiation, light energy (e.g., via a fiber optic)).

Figure 2B:
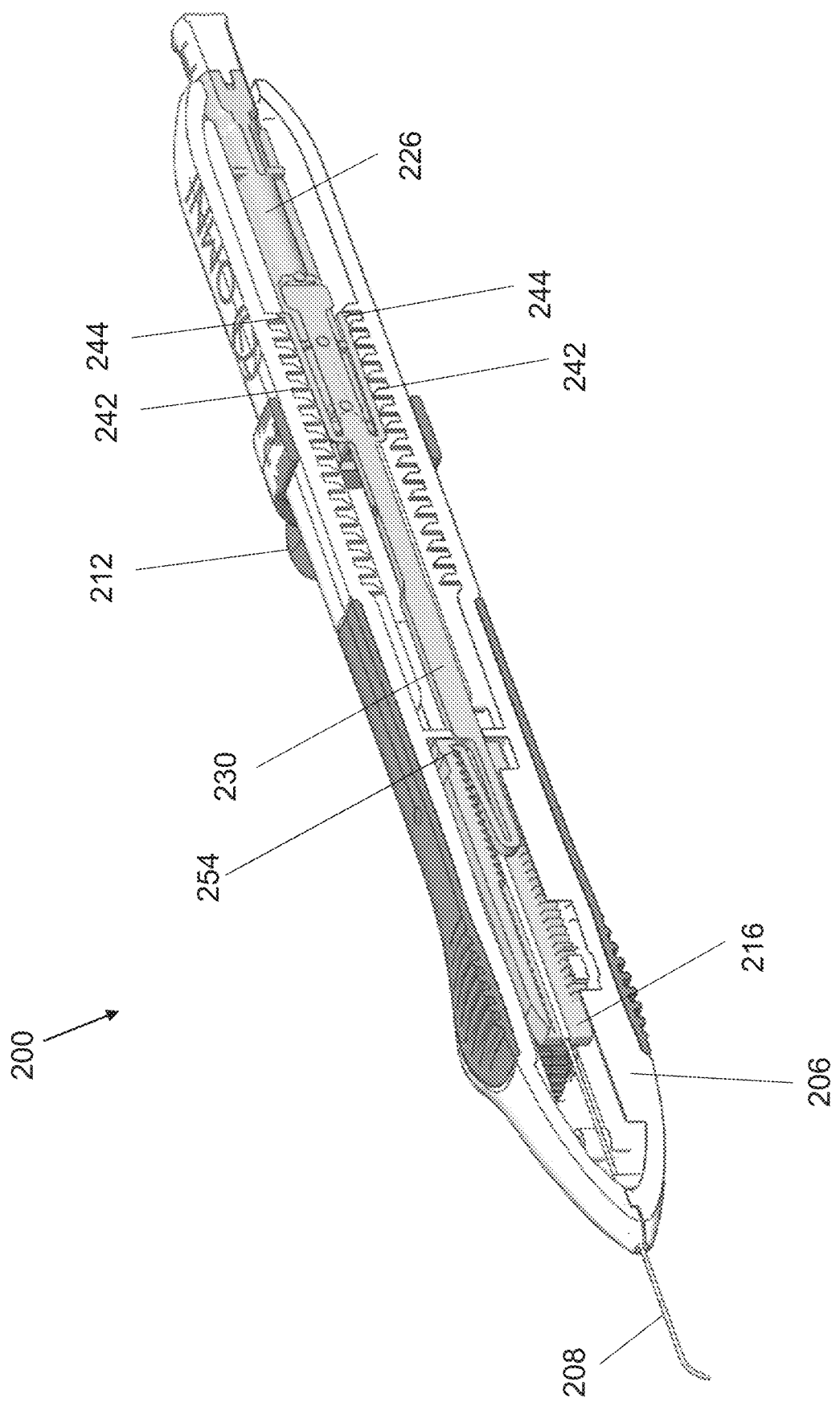
Figure 2C:
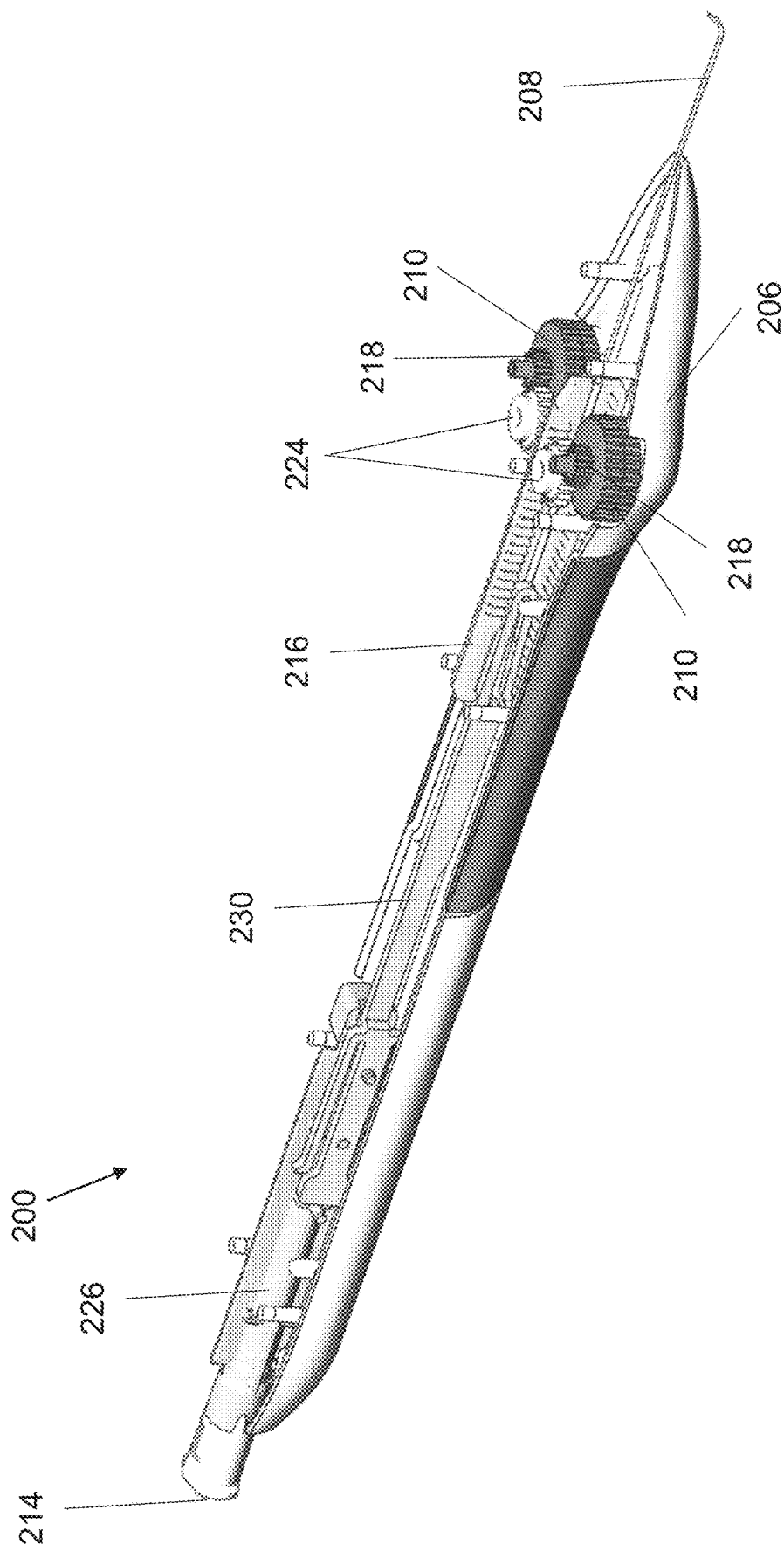
Figure 2D:
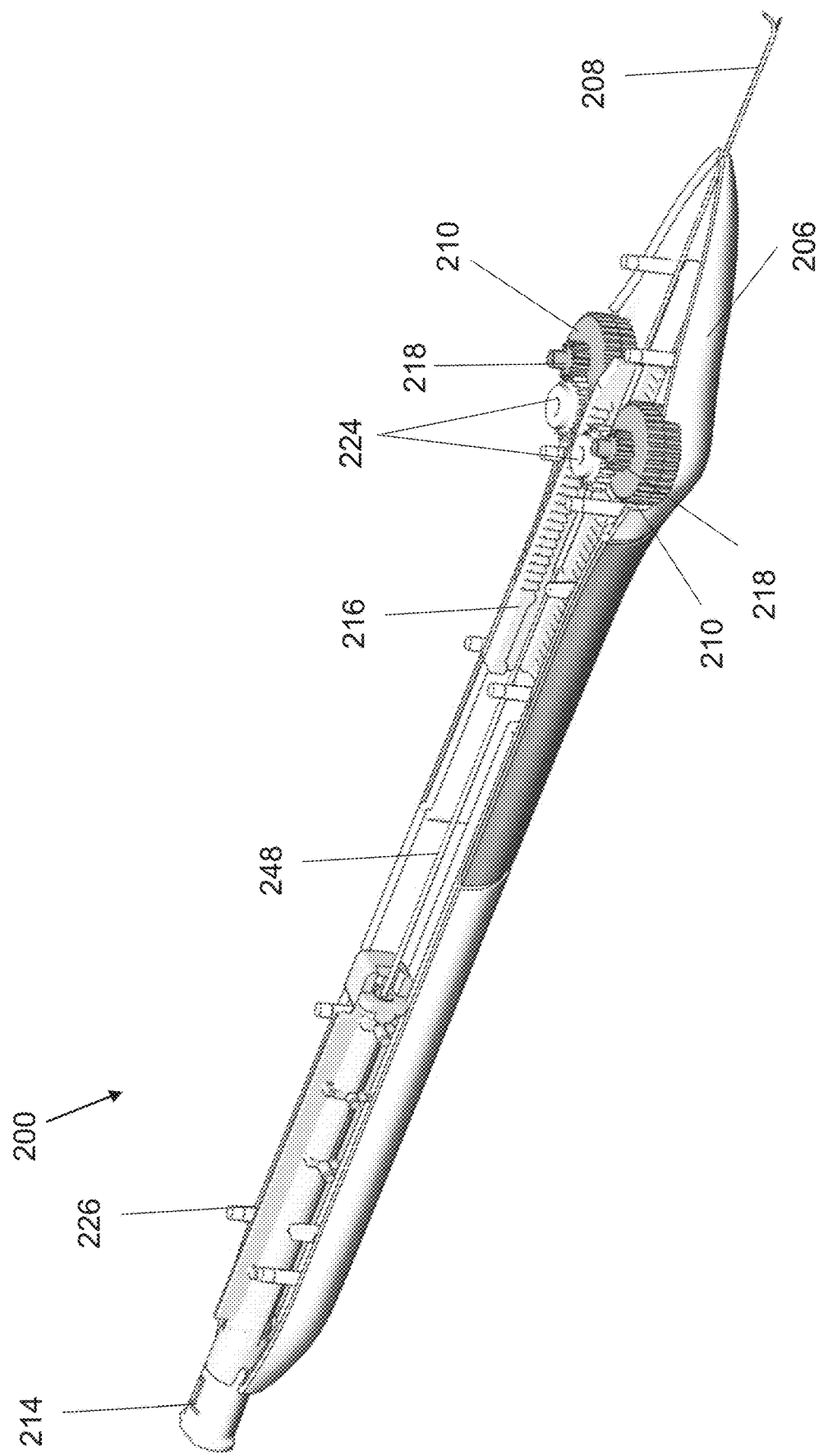
Figure 2E:
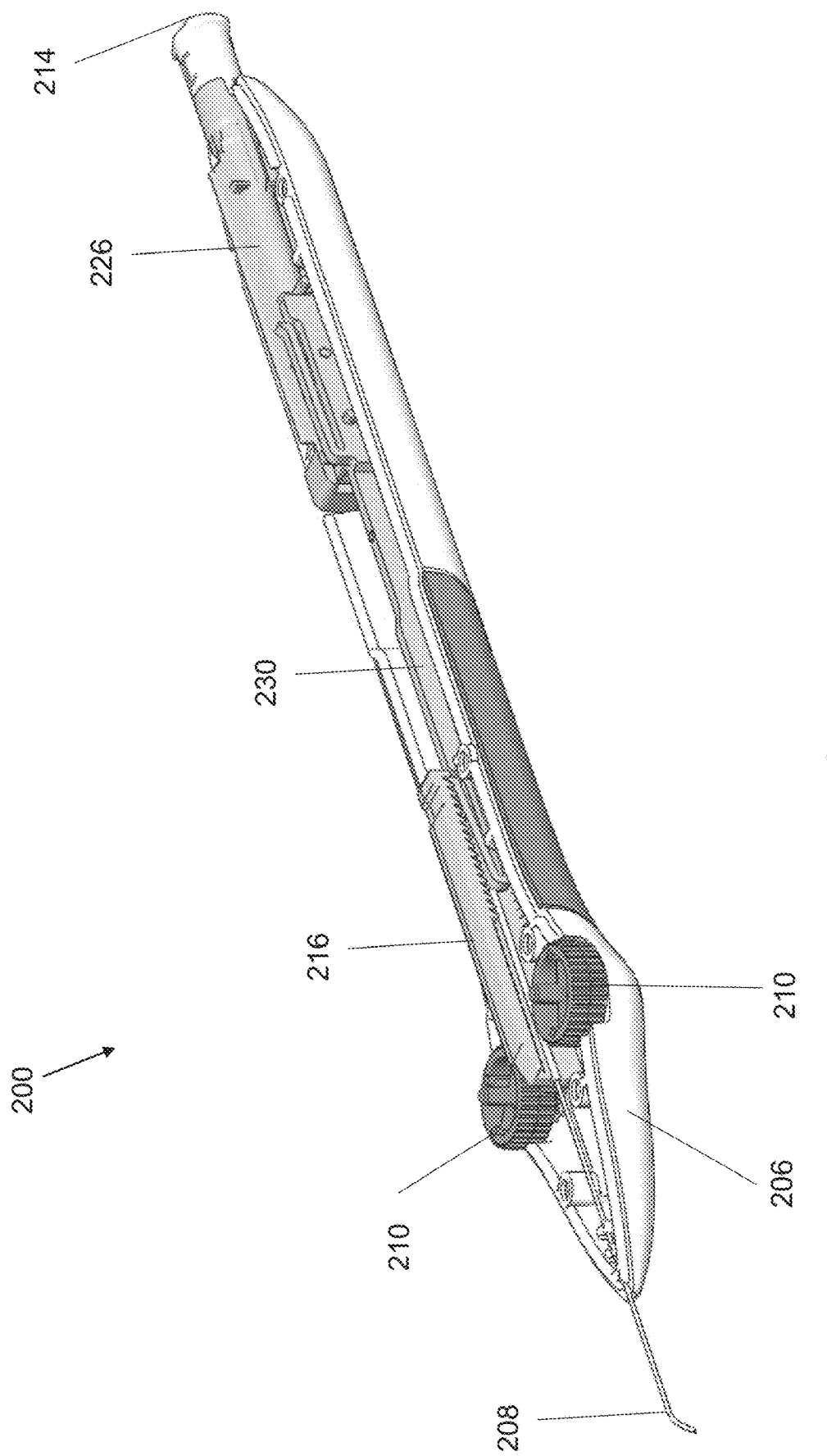
Figure 2F:
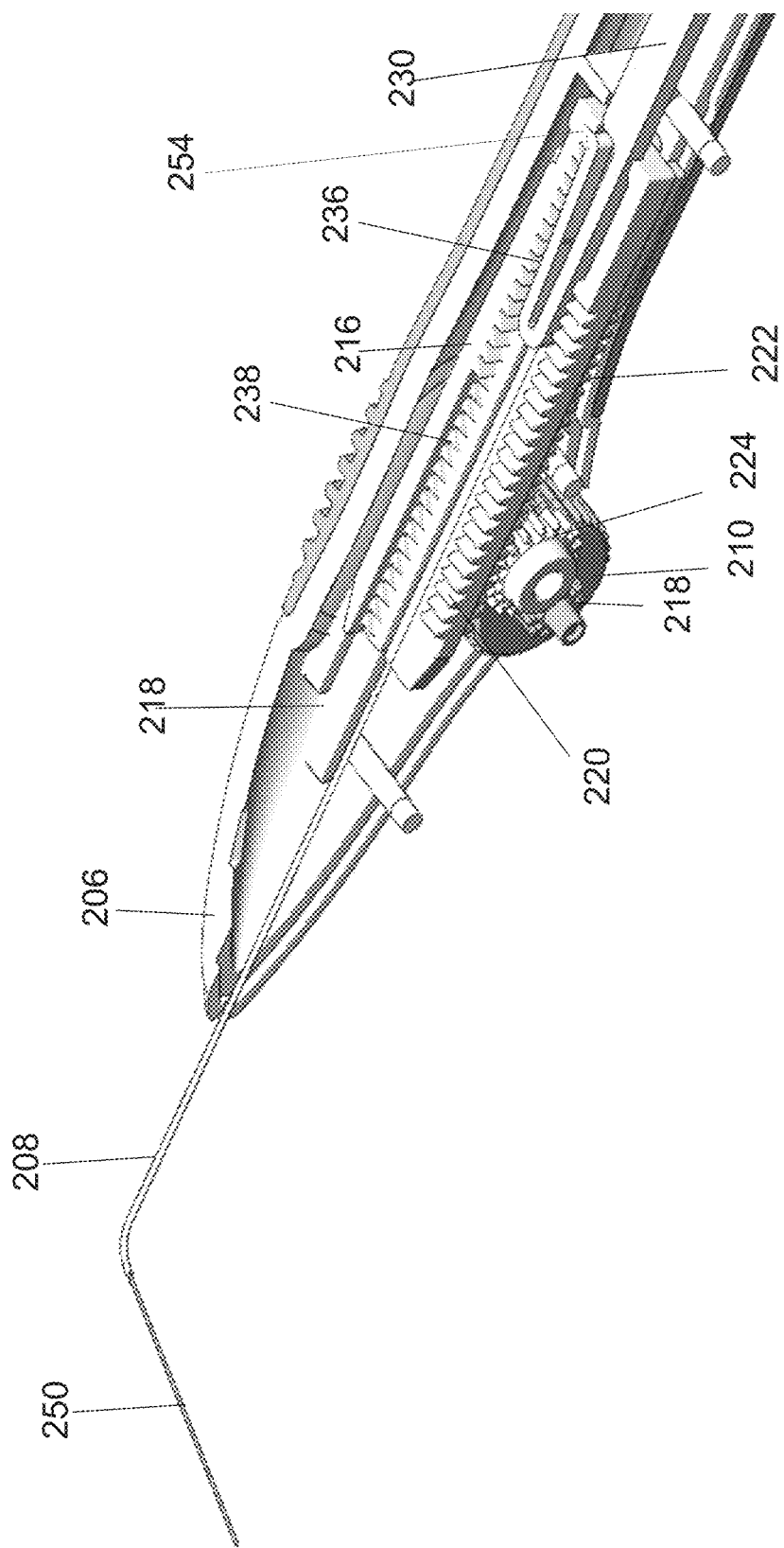
Figure 2G:
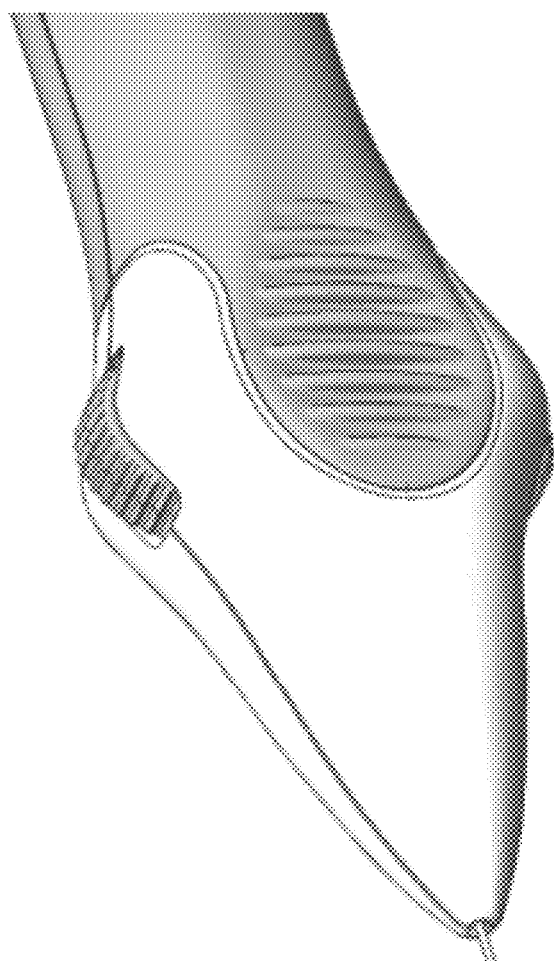
Figure 2H:
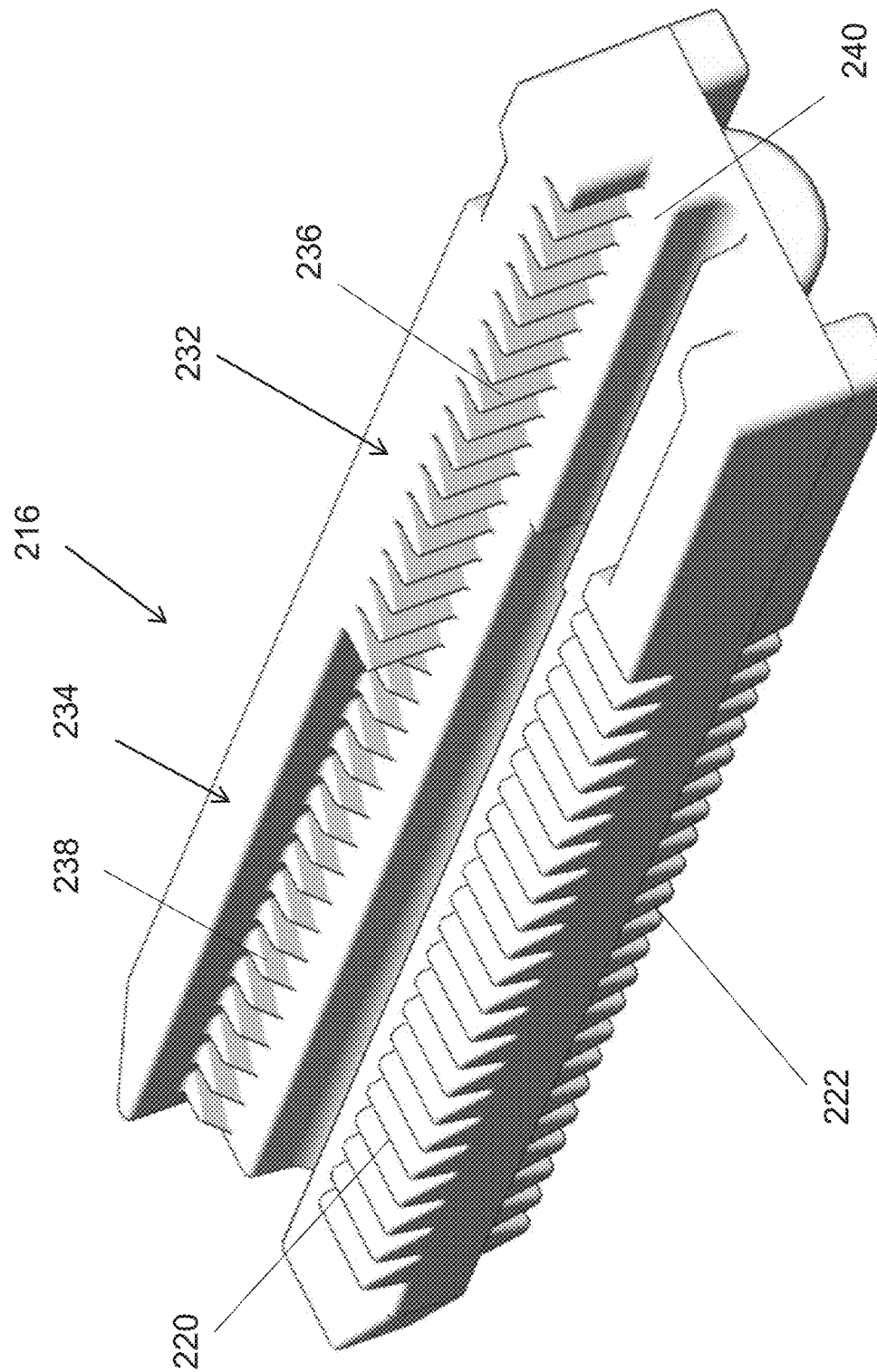

The elongate member may comprise a lumen. For example, in one variation the elongate member may comprise a microcatheter (e.g., a nylon microcatheter). The elongate member may be configured to deliver a fluid composition. The fluid composition may travel through a lumen of the elongate member and may be delivered through an opening of the lumen. For example, as shown in FIG. 2G, the elongate member (250) may be a flexible tube having a lumen in fluid communication with an opening at the distal tip (252).

Figure 8A:
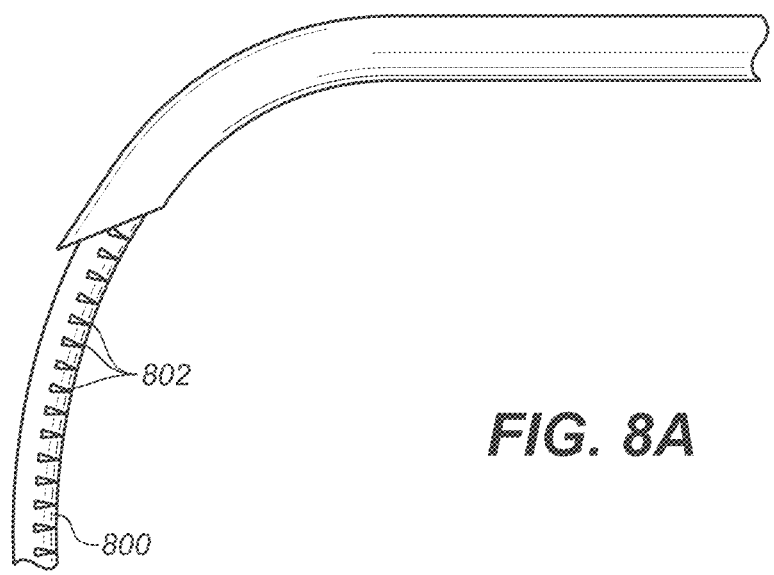
FIGS. 8A-8C show side or perspective views of slidable elongate members according to other variations.
Figure 8B:
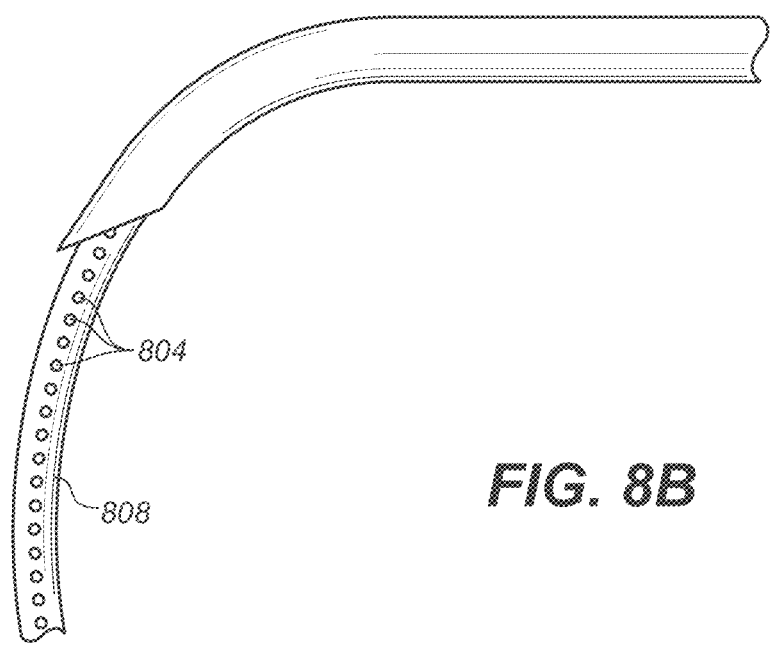
Figure 8C:
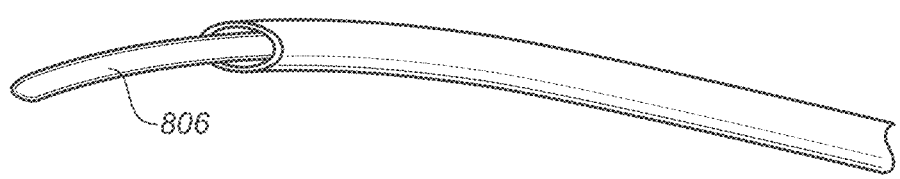

In some variations, the distal end of the elongate member may be configured or modified to aid delivery of the fluid composition into Schlemm's canal. For example, the distal end of the elongate member may comprise a cut out configured as a half tube. Additionally or alternatively to an opening at the distal tip, the elongate member may optionally comprise a plurality of openings through its wall that are spaced along the axial length of the elongate member. In this variation, the fluid composition may be delivered from the reservoir through the openings in the elongate member and into Schlemm's canal. This lateral ejection of fluid (e.g., a viscoelastic fluid) may in some instances enhance disruption of outflow tissues and enhance permeability to aqueous humor. It is understood that the openings can be of any suitable number, size and shape, and spaced along the axial length of the elongate member (including the distal tip) in any suitable manner. For example, the openings may be slots (802) (FIG. 8A) or circles (804) (FIG. 8B). Fluid compositions delivered using the elongate members (800, 808) depicted in FIGS. 8A-8B may partially flow out of the elongate member through the openings and partially out through the distal end of the elongate member. The distal end of the elongate member may also be configured as a half tube (806) (FIG. 8C).

Drive Assembly

The delivery systems generally include a drive assembly. The drive assembly of the delivery system is generally configured to move an elongate member and/or deliver fluid composition into Schlemm's canal. The drive assembly may be at least partially contained within the housing and may include any suitable component or combination of components capable of providing the handle with universal functionality.

The drive assembly may convert an external input (e.g., motion of a user's thumb or finger) into motion of one or more components of the delivery system. More specifically, the drive assembly may cause a slidable elongate member to be extended distally out of a cannula, and/or it may cause a slidable elongate member to be retracted proximally into a cannula. The drive assembly may also optionally cause a fluid composition to be delivered from a reservoir through the elongate member and/or cannula.

Two or more of these effects (i.e., extension of the slidable elongate member, retraction of the slidable elongate member, and/or delivery of a fluid composition) may be actuated using the same actuation mechanism. This may allow for single-handed use of the delivery system. For example, if the actuation mechanism comprises a rotatable element (such as one or more wheels, as in variations described herein), rotating the rotatable element in a first direction may cause extension of the slidable elongate member, and rotating the rotatable element in a second direction may cause retraction of the slidable elongate member. When the delivery system is configured to deliver a fluid composition, rotating the rotatable element (e.g., in the second direction) may also cause delivery of a fluid composition. The delivery of the fluid composition may be simultaneous with movement (e.g., retraction) of the slidable elongate member. In some of these instances, the fluid composition may be delivered to the portion of Schlemm's canal in which the slidable elongate member is advanced; that is, the fluid composition may be delivered to the same angle and length of Schlemm's canal as the extension of the elongate member. When the fluid composition is simultaneous with retraction of the elongate member, fluid composition may take the place of the slidable elongate member as it is retracted and may dilate Schlemm's canal and/or the collector channels at that location in Schlemm's canal. Furthermore, the quantity of fluid delivered may be tied to the amount of movement of the elongate member; that is, a certain predetermined, fixed volume of fluid composition may be delivered via the elongate member (e.g., delivered out of the distal end of the elongate member) for a fixed amount of movement of the elongate member (e.g., a retraction distance) and for a fixed amount of rotation of the rotatable element.

In some variations, the drive mechanism may be configured to allow the delivery system to be used only once—that is, the drive mechanism may prevent, for example, re-extension of the slidable elongate member after a predetermined amount of extension and/or retraction. In other variations the drive mechanism may be configured to allow the elongate member to be extended, retracted, re-extended, and re-retracted an unlimited amount. Exemplary mechanisms by which external input may be converted into motion of one or more components of the delivery system are described in more detail herein.

In some variations, the drive assembly includes components that translate rotational motion into linear motion. For example, the drive assembly may include a linear gear and a pair of pinion gears. Each of the pinion gears may also be coupled to a rotatable component (e.g., a wheel). In some variations, such coupling may be accomplished with a pin that can be threaded through a central opening in the rotatable component and pinion gear, and a nut that secures the rotatable component and pinion gear in a manner so that rotation of the rotatable component also rotates the pinion gear and vice versa. In some variations, the wheels may be attached to the pinion gear by one of the following methods: 1) the wheels and pinion gears are molded as one part using plastic injection molding technology; 2) the wheels slide onto the pinion gear and are secured with adhesive; or 3) the wheels slide on the pinion gear and are mechanically fixed with a fastener or a "press fit," where the wheels are forced onto the pinion gear and friction holds them secure. The wheels and pinion gears may rotate coaxially, in the same direction, and at the same angular rate. In some variations, the wheel may have markings or colorings to indicate degree of advancement or direction of advancement.

One variation of the drive assembly comprises a linear gear, a pair of pinion gears, and at least one rotatable component coupled to each pinion gear. In other variations, the drive assembly includes a linear gear, a single pinion gear, and a single rotatable component coupled to the pinion gear. In variations with a pair of pinion gears, the pinion gears and associated wheel(s) may be disposed on either side of the linear gear. In some variations, the pinion gear(s) and linear gear may contact each other, i.e., the teeth of the pinion gears may directly engage corresponding teeth on the linear gear, and the wheels on one side of the linear gear may contact the wheels on the opposite side of the linear gear. In other variations, the pinion gear(s) and linear gear may be indirectly coupled, for example, via one or more idler gears.

At least a portion of the wheel on a side of the linear gear may extend outside of the housing for a user to manipulate. The drive assembly may be manipulated with one hand when in a first configuration, and then manipulated with the same or the other hand when flipped over to a second configuration. A drive assembly having such flexible capability can be easily used by a surgeon who is right hand dominant or left hand dominant, and may also be used in a procedure in which the handle is flipped during a procedure such that the cannula is facing a first direction in a first portion of the procedure, and facing a second direction in a second portion of the procedure. In a further variation, the drive assembly may include one rotatable component on one side of the handle and the "universal" feature of the handle provided by a cannula that itself can rotate instead of flipping the handle. When the wheel(s) and pinion gear(s) rotate coaxially in the same direction, and when there is no idler gear or an even number of idler gears (e.g., two) between the pinion gear(s) and the linear gear, distal rotation of the portion of the wheel(s) extending out of the housing may result in proximal translation of the linear gear within the housing, and conversely, proximal rotation of the portion of the wheel(s) extending out of the housing may result in distal translation of the linear gear within the housing. When the wheel(s) and pinion gear(s) rotate coaxially in the same direction, and when there is an odd number of idler gears (e.g., one) between the pinion gear(s) and the linear gear within the housing, distal rotation of the portion of the wheel(s) extending out of the housing may result in distal movement of the linear gear within the housing, and conversely, proximal rotation of the portion of the wheel(s) extending out of the housing may result in proximal movement of the linear gear within the housing.

A variation of a drive assembly is reflected in the delivery system (200) of FIGS. 2A-2I. The drive assembly may comprise a linear gear (e.g., a rack) (216), a pair of pinion gears (218) attached to the wheels (210), and a pair of idler gears (224). The pinion gears (218), idler gears (224), and linear gear (216) have teeth that engage each other to translate rotational motion (of the idler gears, pinion gears, and wheels) to linear motion (of the linear gear). More specifically, the linear gear (216) may comprise teeth on both a first side (220) and a second side (222), where the teeth on the first side engage the first idler gear (224), and the teeth on the second side engage the second idler gear (224). The rotation of each of the pinion gears (218), and in turn rotation of each idler gear (224) and the translation of the linear gear (216), is controlled by a rotatable component that can be manipulated by a user from outside the housing (206), shown in the figures as wheels (210).

As shown, the wheels (210) may be integral with the pinion gears (218), such that they rotate coaxially and in the same direction. The pinion gears (218) are then coupled via teeth to idler gears (224) such that the wheels and pinion gears rotate together in the same direction, and the idler gears rotate in the opposite direction. Thus, distal rotation of the portion of the wheel (210) extending out of the housing (206) moves the linear gear (216) distally (and, as described in more detail herein, moves the elongate member toward an extended position), and proximal rotation of the portion of the wheel extending out of the housing moves the linear gear proximally (and, as described in more detail herein, moves the elongate member toward a retracted position). It should be appreciated that in other variations, the wheels (210) and linear gear (216) may be coupled such that distal rotation of the portion of the wheel extending out of the housing moves the linear gear (216) proximally, and proximal rotation of the portion of the wheel extending out of the housing moves the linear gear distally.

That is, the wheels (210) may extend out of the housing (206) of the delivery system, such that the wheels may be rotated by a user to correspondingly rotate the pinion gears (218) and idler gears (224) and thus advance or retract the linear gear (216). The linear gear (216) may be slidable over the cannula (208), such that the cannula and wheels are fixed relative to each other and relative to the housing, while the linear gear translates relative to the housing. Because linear motion of the linear gear (216) may be generated by rotational motion of either of the two pinion gears (218) and idler gears (224), which may in turn be generated by rotating either of the wheels (210) extending from the housing (206), the delivery system (200) may be easily operated using a single hand with either the first side or the second side facing upwards, and thus the cannula (208) facing a first direction or a second direction. Put another way, although the variation shown has two wheels (210), rotation of only a single wheel (210) is required to translate the linear gear (216) (and in turn to extend or retract the elongate member). Rotation of a single wheel (210) will result in coordinated rotation of the second wheel. In other variations, the delivery system may comprise only a single wheel.

The drive assembly may also comprise one or more features to stabilize the pinion gears or otherwise keep them in place. For example, in some variations the drive assembly may comprise wheel spacers configured to sit between axles of the pinion gears.

In other variations, the rotational gears (i.e., pinion gears or idler gears) interfacing with the linear gear may be able to be disengaged from the linear gear by biasing their position off axis from the linear gear. This action de-couples the rotational gear teeth from the linear gear teeth to prevent linear gear movement with wheel rotation. The drive assembly may also be able to be locked to prevent rotation by engaging an intersecting pin or feature that prevents wheel rotation.

Further variations of the drive assembly may not employ translation of rotational motion to linear motion. For example, a slide (e.g., a finger slide) on the handle may be fixed or detachably coupled to a gear within the housing of the handle (e.g., a linear gear as previously described). Here the drive assembly may be configured so that advancement or retraction of the slide causes advancement or retraction of an elongate member and/or delivery of a fluid composition into Schlemm's canal. In yet further variations, a button that can be pressed or squeezed may be employed instead of a slide, or a foot pedal may be employed to deliver a fluid composition and/or advance/retract an elongate member.

Extending and Retracting the Elongate Member

In some variations, a proximal end of the elongate member may be fixed relative to a portion of a drive assembly (e.g., the linear gear (216)), while the distal end may be slidably and coaxially disposed within the cannula lumen. The elongate member may in some instances be bonded to the drive assembly (e.g., via an adhesive) in order to leave the lumen of the elongate member unobstructed. The cannula, in turn, may be fixedly attached to the housing. In variations of the delivery systems in which the handle is reusable and the cannula and elongate member are disposable, a disposable assembly comprising the elongate member pre-loaded within the cannula may be attached to the reusable handle via any suitable mechanism, such as a threaded fastener or snap-in feature.

When the portion of the drive assembly is moved proximally or distally within the housing, this may cause corresponding movement of the elongate member relative to the cannula. That is, movement of the portion of the drive assembly toward the cannula (i.e., toward the distal end of the housing) may cause the elongate member to move from a retracted position to an extended position, and movement of the portion of the drive assembly away from the cannula (e.g., toward the proximal end of the housing) may cause the elongate member to move from an extended position to a retracted position. An example of an elongate member (250) in an extended position is shown in FIGS. 2F and 2G. As shown in FIG. 2F, the linear gear (216) may be in a distal position when the elongate member (250) is extended from cannula (208).

Reservoir

The systems may generally include a reservoir. The reservoir may contain various fluid compositions for delivery. Exemplary fluid compositions include saline and viscoelastic fluids. The viscoelastic fluids may comprise hyaluronic acid, chondroitin sulfate, cellulose, derivatives or mixtures thereof, or solutions thereof. In one variation, the viscoelastic fluid comprises sodium hyaluronate. In another variation, the viscoelastic composition may further include a drug. For example, the viscoelastic composition may include a drug suitable for treating glaucoma, reducing or lowering intraocular pressure, reducing inflammation, and/or preventing infection, fibrosis, scarring, clotting, thrombosis, bleeding, or neovascularization. Drugs such as antimetabolites, vasoconstrictors, anti-VEGF agents, steroids, heparin, anti-inflammatories, nonsteroidal anti-inflammatories (NSAIDs), other anticoagulants, fibrinolytic compounds, biologic agents, Rho kinase (ROCK) inhibitors, and agents for gene therapy, DNA, RNA, or stem cell-based approaches, may also be delivered in combination with the viscoelastic composition. Examples of glaucoma drugs include prostaglandins, beta blockers, miotics, alpha adrenergic agonists, or carbonic anhydrase inhibitors. Anti-inflammatory drugs such as NSAIDs, corticosteroids or other steroids may be used. For example, steroids such as prednisolone, prednisone, cortisone, cortisol, triamcinolone, or shorter acting steroids may be employed. Examples of antimetabolites include 5-fluoruracil or mitomycin C.

Examples of drugs or antibodies that prevent neovascularization include bevacizumab, ranibizumab, and others. In still another variation, the system delivers the drug alone, without the viscoelastic composition. Saline solution may also be the fluid employed. In yet other variations, the system may be configured to deliver a gas, such as but not limited to air, an expansile gas (e.g., SF6, C3F8).

In some variations, the reservoir may be at least partially defined by a fluid assembly and the housing, and the linear gear within the handle. The fluid assembly may be made from any suitable material previously mentioned for the cannula and the housing. The volume of fluid (in microliters) contained within the reservoir may range from about 2 µl to about 1000 µl, or from about 2 µl to about 500 µl. In some variations, the reservoir volume may range from about 50 µl to about 100 µl.

The fluid composition may be preloaded in the reservoir or loaded into the reservoir prior to use of the system, e.g., at the start of an ocular procedure, so that the fluid can be delivered by a single device and by a single user. Again, this is in contrast to other systems that use forceps or other advancement tools to advance a fluid delivery catheter into Schlemm's canal and/or devices containing viscoelastic fluid that are separate or independent from a delivery catheter or catheter advancement tool, and which require connection to the delivery catheter or catheter advancement tool during a procedure by, e.g., an assistant, or by the hand of the surgeon while the delivery catheter or catheter advancement tool is held by another hand of the surgeon. For example, a loading component may be provided on the fluid assembly for transfer of a fluid composition into the reservoir. The loading component may have any suitable configuration that provides reversible securement of a fluid container, e.g., a syringe, cartridge, etc., to the system, and loading of a fluid composition into the reservoir. The loading component may be a luer fitting or include a one-way valve.

Figure 9:
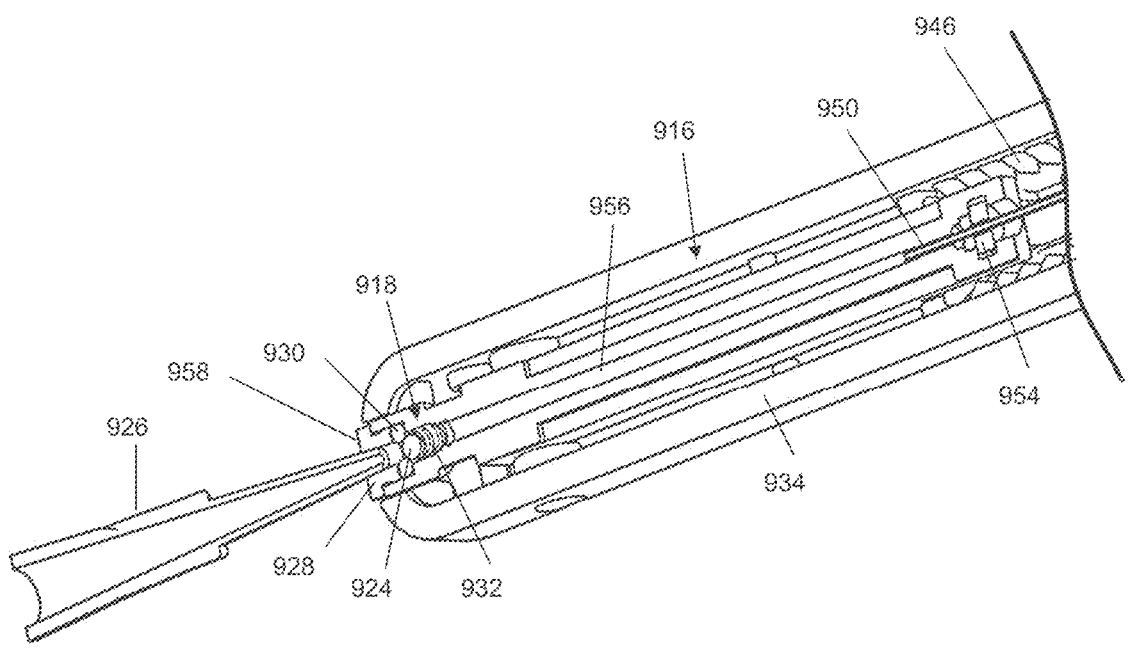
FIG. 9 shows a close-up cutaway view of the proximal end of an exemplary delivery system.

For example, the exemplary delivery system (200) in FIGS. 2A-2I comprises a fluid assembly comprising a reservoir (226). In an exemplary method, a fluid composition may be loaded into the reservoir (226) though a proximal opening (214) via a proximal seal. The distal end of the reservoir may be formed by a plunger and a distal seal. The proximal opening (214) may comprise a mechanical seal. An example of a proximal seal is shown in FIG. 9. The proximal seal (918) may be a mechanical seal located at the proximal end of the reservoir (956) and comprising a ball bearing (924) spring-biased against an o-ring or gasket (930) to seal closed the reservoir. A loading tool (926) (e.g., a nozzle) may be used to open the seal by pressing against the ball bearing (924) to move it proximally toward an open position. In other variations, the delivery system may comprise a luer fitting that allows a viscoelastic cartridge to be directly connected to the delivery system. While the proximal seal (918) is open, the fluid composition may be loaded into the reservoir. After loading of the fluid composition, the loading tool (926) may be removed, allowing the ball bearing (924) to return to its closed position. An o-ring or gasket (930) may sit between the ball bearing (924) and a spring (932), such that force from the spring presses the ball bearing into the gasket to form a seal between the ball bearing and gasket in the closed position. The loading tool (926) may be configured to fit into the proximal opening (958) to press against the ball bearing (924). The distally oriented force against the ball bearing (924) may move it distally into the open position, compressing the spring (932), and creating an opening between the ball bearing (924) and the gasket (930), through which the fluid composition may flow. When the loading tool (926) is removed from the proximal opening (958), the spring (932) pushes the ball bearing (924) proximally back into the closed position.

It should be appreciated that in other variations, the reservoir may comprise other types of seals allowing a fluid composition to be loaded into the reservoir. For example, the seal may comprise a membrane (e.g., a silicone membrane). A fluid composition may be loaded into the reservoir by puncturing the membrane with a needle (e.g., a 25 gauge needle). In yet other variations, the delivery systems described herein may be configured to receive a prefilled cartridge comprising a fluid composition. For example, the handle and fluid assembly may be configured such that a prefilled cartridge can be inserted into the fluid assembly.

In order to load the reservoir, it may be desirable to at least temporarily secure the fluid assembly in place in order to allow application of distal force to the seal. In some variations, the delivery system may comprise a lock configured to hold the fluid assembly in place while a fluid composition is injected into the reservoir. However, it should be appreciated that in other variations the delivery system may not comprise a lock. In variations having a lock, it may be desirable for the lock to be removable from the delivery system (or to otherwise release the fluid assembly) in order to allow the fluid assembly to translate relative to the housing after the reservoir is loaded. Translation of the fluid assembly may allow for extension of the slidable elongate member and/or injection of the fluid composition during the procedure, as is described in more detail herein.

In variations of the delivery systems having a lock, the lock may optionally additionally act as a cap to protect a distal opening to the reservoir. In these variations, the lock may comprise a first configuration in which it both holds the reservoir in place and covers the proximal opening to the reservoir, and a second configuration in which it holds the reservoir in place but allows the proximal opening to the reservoir to be accessed, such that the reservoir can be loaded with a fluid composition. In some instances, the lock may rotate from the first position to the second position.

An exemplary lock (212) is shown in the delivery system (200). As shown in FIGS. 2A-2B and 2I, the lock (212) may comprise a pin (228) configured to fit into an opening in the handle of the delivery system. The lock (212) may have a shape configured to removably clip around the handle of the delivery system when the pin (228) is within the opening in the handle, allow the lock (212) to be securely fastened to the handle, while also allowing a user to remove it when desired. When the pin (228) is inserted into the opening in the handle, it may restrict movement of the reservoir (226) relative to the housing. This may, for example, allow a loading tool to apply force through the proximal opening to open the proximal seal of the reservoir (226), without the reservoir (226) sliding distally within the handle. Restricting movement of the reservoir (226) relative to the handle may prevent motion of the reservoir or other internal components of the delivery system before use (e.g., during transit). That is, when the pin (228) is inserted into the opening in the handle, it may also prevent rotation of the wheels, pinion gears, and idler gears, as well as translation of the linear gear. Once loading of the reservoir is complete, the lock (212) may be removed from the handle, thus removing the pin (228) from the opening in the handle, at which point the reservoir (226) may no longer be restricted by the lock from moving relative to the housing.

Delivering a Fluid Composition

The delivery systems described herein may be configured to deliver fluid to Schlemm's canal. The fluid may be delivered in a volume that provides sufficient force to disrupt Schlemm's canal and surrounding trabeculocanalicular tissues. Exemplary disruptive volumes may be about 1 µl, about 2 µl, about 3 µl, about 4 µl, about 5 µl, about 6 µl, about 7 µl, about 8 µl, about 9 µl, about 10 µl, about 11 µl, about 12 µl, about 13 µl, about 14 µl, about 15 µl, about 16 µl, about 17 µl, about 18 µl, about 19 µl, or about 20 µl. In some variations, the disruptive volume fluid may range from about 1 µl to about 50 µl, or from about 20 µl to about 50 µl.

As mentioned above, an elongate member may be coaxially disposed within the cannula lumen. The elongate member may comprise a lumen. The lumen of the elongate member may be operatively connected to a reservoir for delivery of a fluid composition into Schlemm's canal. The elongate member generally has a proximal end, a distal end, and a wall that defines the lumen extending therethrough. However, in some instances, the delivery system lacks an elongate member conduit, and the fluid composition is delivered solely through the cannula. In other instances, two elongate members may be employed that each simultaneously advance through the canal in both clockwise and counterclockwise directions to more rapidly cannulate Schlemm's canal and deliver therapy.

When the delivery systems are employed to deliver a fluid composition, the fluid composition may be preloaded in a reservoir of the system or loaded into the reservoir prior to use of the system. Some variations of the fluid assembly include a locking mechanism for preventing movement of the assembly within the handle, e.g., when the linear gear is being advanced or retracted. The locking mechanism may comprise a ratchet pawl, a combination of ratchet pawls or any other suitable mechanism that can be locked to prevent movement of the fluid assembly, and unlocked to allow movement of the fluid assembly.

Referring back to FIGS. 2A-2I, an exemplary delivery system (200) for delivering a fluid composition shown there may comprise a housing (206) and a cannula (208) extending from the distal end of the housing. A drive assembly (described in more detail above) may be located within the housing (206), as may be a fluid assembly (also described in more detail above). As described above, the drive assembly may comprise a linear gear (216) and a pair of pinion gears (218) each coupled to a wheel (210). The delivery system (200) may comprise a slidable elongate member (250). A proximal end of the elongate member (250) may be fixed relative to the linear gear (216), while the distal end of the elongate member (250) may be slidably and coaxially disposed within the lumen of the cannula (208). A reservoir (226) of the fluid assembly may be fluidly connected to a lumen of the elongate member (250). For example, a plunger (248), comprising a lumen may fluidly connect the reservoir (226) to the lumen of the elongate member (250). The proximal end of the plunger (248) may be located slidably within the reservoir (226), and the distal end of the plunger may be fixedly attached to the linear gear (216) of the drive assembly.

The fluid assembly and the drive assembly may be connected via linkage (230). The linkage (230) may be configured to allow the fluid assembly and drive assembly to be moved as a unit, and may allow limited movement of the fluid assembly and drive assembly relative to each other. In some variations, the linkage (230) may allow different amounts of movement depending on the location of coupling with the drive assembly. The proximal end of the linkage (230) may be fixedly attached to the fluid assembly. The distal end of the linkage (230) may be coupled to the linear gear (216) of the drive assembly.

The linear gear (216) may comprise a proximal portion (232) and a distal portion (234). In some variations, the proximal portion (232) may comprise teeth (236), and the distal portion (234) may comprise teeth (238). When the linkage (230) is coupled to the proximal portion (232) of the linear gear (216), the distal end of the linkage may be coupled via a one-way ratchet to the proximal portion of the linear gear of the drive assembly. The one-way ratchet connection may allow the distal end of the linkage (230) to move distally relative to the linear gear (216) but not proximally. More specifically, when the linkage (230) is coupled to the proximal portion (232) of the linear gear (216), the distal end of the linkage (230) may be able to be moved distally relative to and along a proximal portion of a track (240) in the proximal portion of the linear gear (216), but teeth (236) in the proximal portion of the track may resist proximal movement of the distal end of the linkage along the proximal portion of the track. The teeth (236) may be located on a surface perpendicular to the sides having teeth (220, 222) configured to interface with the pinion gears (218). The surface having teeth (236) may also face inward toward track (240).

In contrast, when the linkage (230) is coupled to the distal portion (234) of the linear gear (216) (i.e., when the linkage has been moved distally relative to the linear gear to reach the distal portion of the track (240)), the distal end of the linkage may be able to be moved both distally and proximally relative to the linear gear (216) along the distal portion of the track (240). The distal portion of the track may comprise teeth (238) that do not restrict the movement of the linkage (230) to a single direction along the distal portion of the track (240) (i.e., the linkage (230) may move proximally and distally within the track). The teeth (238) may allow for controlled movement of the linkage (230) relative to the linear gear (216) as the distal end of the linkage engages with each tooth, while still allowing the linkage to move both distally and proximally relative to the linear gear. The engagement of the distal end of the linkage (230) with the teeth (238) may provide haptic feedback to the user as the linkage is moved along the teeth. The engagement of the distal end of the linkage with the teeth (238) may also provide resistance to prevent fluid pressure from fluid within the reservoir from moving the plunger distally out of the reservoir (and in turn causing the linear gear and elongate member to move distally) when a user is not controlling or preventing the rotation of the wheel, after proximal movement of the linear gear and plunger. That is, after a user has rotated wheel (210) to generate proximal movement of the linear gear (216) and proximal movement of the plunger (248) within the reservoir (226), thereby causing fluid to be displaced from the reservoir for delivery through the plunger and elongate member (250), the user may release control of the wheel. When the user is not controlling or preventing rotation of the wheel (210), fluid pressure from fluid within the reservoir (226) may generate a force that could, without an opposing force, move the plunger (248) distally out of the reservoir, and in turn cause the linear gear (216) to move distally and the elongate member (250) to extend. The engagement between the teeth (238) and the distal end of the linkage (230) may provide an opposing force to resist this force generated by fluid within the reservoir (226). The opposing force on teeth (238) may stop the linear gear (216) from moving distally in response to the force generated by fluid within the reservoir (226), which in turn may prevent the plunger (248) from moving distally out of the reservoir and prevent the elongate member (250) from extending.

The teeth (238) in the distal portion (234) of the linear gear (216) may each have a triangular shape having a sloped slide, such that as the linkage (230) translates in one direction relative to the teeth (238), the distal portion of the linkage (230) flexes in one dimension away from the teeth (238), and as the linkage translates in a second direction relative to the teeth (238), the distal portion of the linkage flexes in a second dimension away from the teeth. The teeth (238) may be smaller than teeth (236) to allow for proximal and distal motion of the linkage (230) relative to the linear gear (230) while still providing haptic feedback and resistance. The teeth (238) may have two different sloped surfaces to cause flexing of the distal portion of the linkage (230) in perpendicular directions depending on the direction of translation of the linkage relative to the linear gear (230). For example, when wheel (210) is rotated to cause proximal movement of the linear gear (216) relative to the linkage (230), the distal portion of the linkage may flex in a first direction in response to force from the teeth (238); when the wheel (210) is rotated in an opposite direction to cause distal movement of the linear gear (216) relative to the linkage (230), the distal portion of the linkage may flex in a second direction in response to force from the teeth (238); and the first and second directions of flexion may be perpendicular to each other.

The engagement of the linkage (230) with one side of the teeth (238) may provide haptic feedback and stepwise load holding capabilities during distal movement of the linkage relative to the linear gear (216), while the engagement of the linkage (230) with the second side of the teeth (238) may provide haptic feedback and stepwise load holding capabilities and/or prevent distal spring-back of the linear gear (216) and spring-back extension of the elongate member (250) in response to fluid pressure generated by proximal movement of the linkage (in turn resulting in proximal movement of the plunger within the reservoir creating the fluid pressure), after a user is no longer controlling the movement of the drive assembly (e.g., releases contact on the wheel (210)). That is, when the wheel (210) is rotated to cause distal movement of the linear gear (216) relative to the linkage (230), and in turn extension of the elongate member (250), engagement between the distal portion of the linkage and one side of the teeth (238) (e.g., a distal side of the teeth) may provide haptic feedback. When the wheel (210) is rotated in an opposite direction to cause proximal movement of the linear gear (216) relative to the linkage (230), and in turn retraction of the elongate member (250), engagement between the distal portion of the linkage and another side of the teeth (238) (e.g., a proximal side of the teeth) may provide haptic feedback. Additionally, when a user releases contact on the wheel (210) or otherwise no longer controls the position or movement of the wheel after proximal movement of the linear gear (216) relative to the linkage (230), engagement between the distal portion of the linkage and the first side of the teeth (e.g., a distal side of the teeth) may prevent distal spring-back of the linear gear, and in turn spring-back extension of the elongate member, in response to force on the plunger from fluid within the fluid reservoir.

In the variation shown, the distal portion of the linkage (230) has a u-shaped bend with a notch (254) configured to engage teeth (236) and teeth (238) when the distal portion of the linkage is coupled to the proximal (232) and distal (234) portions of the linear gear (216), respectively. When the distal portion of the linkage (230) is coupled to the proximal portion (232) of the linear gear (216), if the linear gear moves proximally relative to the linkage (230), the u-shaped bend allows connection point of the linkage (i.e., the notch (254)) to move away from the teeth (236) and into the space of the track (240) to allow proximal motion of the linear gear relative to the linkage. When the distal portion of the linkage (230) is coupled to the proximal portion (232) of the linear gear (216), the coupling between the connection point of the linkage (i.e., the notch (254)) and the teeth (236) prevents the linear gear (216) from moving distally relative to the linkage (230). That is, the coupling maintains the distance separating the proximal end of the linear gear (216) and the distal end of the reservoir (226). When the distal portion of the linkage (230) is coupled to the distal portion (234) of the linear gear (216), if the linear gear (216) moves proximally relative to the linkage (230), the u-shaped bend allows the connection point of the linkage (i.e., the notch (254)) to move away from the teeth (238) and into the space of the track (240) to allow proximal motion of the linear gear relative to the linkage. When the distal portion of the linkage (230) is coupled to the distal portion (234) of the linear gear (216), if the linear gear (216) moves distally relative to the linkage (230), the u-shaped bend allows the connection point of the linkage (i.e., the notch (254)) and a portion of the distal end of the linkage to deflect out of plane as it travels over a sloped surface of the teeth (238). In other variations, the distal portion of the track may not comprise teeth (e.g., may be smooth).

When the distal end of the linkage (230) is within the proximal portion (232) of the linear gear, the fluid assembly and linear gear may be able to be brought closer together (via shortening of the portion of the linkage between the fluid assembly and the linear gear) when the linear gear is moved proximally and the elongate member is retracted, and the fluid assembly remains fixed relative to the housing; however, the distance between the linear gear and fluid assembly may be fixed when the linear gear is moved distally and the elongate member is extended. As such, when the linear gear is moved distally and the elongate member is extended, the fluid assembly may move distally. In contrast, as a result of the differences between the proximal and distal portions of the linear gear (216), when the distal end of the linkage (230) is within the distal portion (234) of the linear gear, the linear gear (216) may be able to be moved proximally and distally without the linkage (230) or fluid assembly moving; that is, the fluid assembly and linear gear may be able to be moved both closer and farther from each other. However, as described in more detail herein, the linear gear (216) may still provide resistance to relative movement of the linkage (230) when the distal end of the linkage is within the distal portion of the linear gear, but that resistance may be overcome by the user (e.g., by rotating the wheel (210)).

Put another way, the relative movement of the linear gear (216) and linkage (230) (and, in turn, the relative movement of the linear gear and the fluid assembly fixedly attached to the linkage) may be more or less restricted depending on the relative locations of the linear gear and linkage. In a first configuration, the linkage's movement relative to the linear gear may be restricted, such that the linkage can move in one direction (e.g., distally) relative to the linear gear but not in the other direction (e.g., proximally). Thus, in the first configuration, the linear gear may be able to move toward the fluid assembly but not away from the fluid assembly. In the second configuration, the linkage's movement relative to the linear gear may not be restricted to one direction, i.e., the linkage may be able to move proximally and distally relative to the linear gear. Thus, the linear gear may be able to move toward and away from the fluid assembly. In the variation of delivery system (200), the transition between the first configuration and second configuration may be based on the amount of translation of the linkage relative to the linear gear. The linkage may initially be in the first configuration, before it has translated distally relative to the linear gear. Once the linkage has translated distally relative to the linear gear by a portion of the linear gear's length (e.g., half the length of the linear gear), the delivery system may change from the first configuration to the second configuration. It should be appreciated that in other variations, the linkage may be fixedly coupled to the linear gear and slidably coupled to the fluid assembly. In yet other variations, the linear gear and the fluid assembly may be connected via other mechanisms providing two configurations, wherein in a first configuration the linear gear is movable toward but not away from the fluid assembly, and in a second configuration the linear gear is movable toward and away from the fluid assembly. In these variations, the delivery system may switch from the first to the second configuration automatically or manually.

Thus, the linear gear (216) and the fluid assembly may be movable relative to each other and may be movable within the housing (206). Movement of the linear gear (216) and fluid assembly relative to each other, as well as relative to the housing (206), may cause one or more effects, including extension and retraction of the slidable elongate member and/or delivery of a fluid composition. More specifically, because the proximal end of the plunger (248) may be located slidably within the reservoir (226), and the distal end of the plunger may be fixedly attached to the linear gear (216), movement of the linear gear toward the reservoir may cause proximal movement of the plunger within the reservoir. This may cause the length of the plunger (248) located within the reservoir (226) to increase. The portion of the plunger (248) within the reservoir (226) may displace fluid with the reservoir. The displaced fluid may move distally through the lumen of the plunger (248), through the lumen of the elongate member, and may be delivered out through a distal opening of the lumen of the elongate member.

Additionally, as mentioned above, movement of the linear gear (216) relative to the housing (206) may cause the slidable elongate member (250) to extend or retract. The linear gear (216) may be moveable between proximal and distal positions via rotation of a wheel (210). Because the proximal end of the elongate member (250) may be fixed relative to the linear gear (216) and the distal end of the elongate member may be slidable within the lumen of the cannula (208), when the drive assembly is in a proximal position, the elongate member may correspondingly be in a retracted position relative to the cannula (208) (e.g., proximal to the distal tip of the cannula). When the drive assembly is in a distal position, the elongate member may correspondingly be in an extended position relative to the cannula (208). When the elongate member (250) is in the extended position, the distal end of the elongate member may extend out of the cannula (e.g., distal to the distal tip of the cannula).

In one configuration, relative motion of the drive assembly (and its linear gear (216)), fluid assembly (and its reservoir (226)), and housing (206) may thus be used to extend the slidable elongate member (250) out of the cannula (208), and to retract the elongate member while simultaneously delivering fluid. In another configuration, relative motion of the drive assembly, fluid assembly, and housing (206) may be used to extend and retract the slidable elongate member (250) out of and into the cannula (206) without delivering fluid.

For example, the delivery system (200) may start in a configuration where the reservoir (226) and linear gear (216) are separated by the full distance of the linkage (230), the reservoir (226) is located at the proximal end of the housing (206), and the slidable elongate member is in a retracted position within the cannula (208). This configuration is show in FIGS. 2B-2E. One or both of the wheels (210) may be rotated in a first direction to advance the linear gear (216) distally within the housing (206). The linkage (230) may cause the reservoir (226) to move an equal distance distally within the housing (206), maintaining the spacing between the reservoir and the linear gear (216). The spacing may be maintained because in this configuration, the linear gear (216) can move proximally relative to the linkage (230) but not distally relative to it due to the teeth (236) in the track (240) on the proximal portion (232) of the linear gear, which couple with the distal end of the linkage (230). Thus, when the linear gear moves distally, the coupling between the linkage (230) and the linear gear (216) pulls the linkage and reservoir (226) distally within the housing (206). As the linear gear (216) advances, the elongate member (250) may move from the retracted position distally toward the extended position. This may cause the elongate member (250) to exit the distal opening of the cannula (208). The delivery device (200) may be configured such that moving the linear gear (216) to its distal-most position within the housing (206) results in the elongate member (250) moving to its fully extended, distal-most position relative to the cannula.

When the linkage (230) and linear gear (216) are in the first configuration in which the linkage can move proximally but not distally relative to the linear gear, one or both wheels (210) may then be rotated in a second direction to retract the linear gear proximally within the housing (206). This may cause the slidable elongate member (250) to move from an extended position toward a retracted position. However, the fluid assembly and its reservoir (226) may not correspondingly move proximally within the housing (206). The housing (206) may comprise interior teeth (242) near the reservoir (226) configured to engage protrusions (244) fixed relative to the reservoir. For example, the protrusions (244) may be part of the proximal portion of the linkage (230) that is fixedly attached to the reservoir (226). The teeth (242) and protrusions (244) may allow the reservoir (226) to move distally within the housing (206) but not proximally within the housing. As such, when the linear gear (216) is retracted within the housing (206), the reservoir (226) may remain fixed relative to the housing. The linear gear (216) and reservoir (226) may therefore move closer together, with the linkage (230) moving distally along the track (240) in the linear gear to accommodate this movement. As the linear gear (216) and reservoir (226) move closer together, the plunger may displace fluid within the reservoir (226), as described in more detail above. The fluid may then travel through the lumen of the plunger and be delivered out through the lumen of the elongate member (250).

When the linkage (230) and linear gear (216) are in the second configuration in which the linkage can move both proximally and distally relative to the linear gear, when one or both wheels (210) are rotated in a first direction to advance the linear gear (216) distally within the housing (206), the elongate member (250) may move distally toward the extended position. However, the linkage (230) and reservoir (226) may not move within the housing (206). Instead, the distal end of the linkage (230) may slide distally within the track (240) of the linear gear (216). This may cause the plunger to move distally out of the reservoir (226).

In the second configuration, when one or both wheels (210) are rotated in the second direction to retract the linear gear (216) proximally within the housing (206), this may cause the slidable elongate member to move from an extended position toward a retracted position. The distal end of the linkage (230) may slide proximally within the track (240) of the linear gear (216). Although the proximal movement of the linkage (230) relative to the linear gear (216) may cause the plunger to move proximally into the reservoir (226), the plunger may not displace fluid within the reservoir (226), since it is returning to its position immediately prior to moving distally out of the reservoir.

Thus, in both the first and second configurations, rotating one or more wheels (210) in a first direction, and correspondingly moving the linear gear (216) distally within the housing (206), may cause the slidable elongate member (250) to move toward an extended position. In both the first and second configurations, rotating one or more wheels (210) in an opposite, second direction, and correspondingly moving the linear gear (216) proximally within the housing (206), may cause the slidable elongate member (250) to move toward a retracted position. But rotating one or more wheels (210) in the second direction, and correspondingly moving the linear gear (216) proximally within the housing (206), may have different effects in the first and second configurations with respect to fluid delivery. In particular, in the first configuration, moving the linear gear (216) proximally within the housing (206) may cause fluid to be delivered out through the lumen of the elongate member during retraction of the elongate member. In contrast, in the second configuration, moving the linear gear (216) proximally within the housing (206) may cause the slidable elongate member to move toward a retracted position without any fluid being delivered.

In the first configuration, as the elongate member is retracted, fluid may be delivered simultaneously out of the elongate member. The fluid may take the place of the elongate member as it is retracted, and as such, the fluid may be delivered to a trajectory that is the same as the trajectory along which the elongate member was advanced. A fixed, predetermined volume of fluid may be delivered for a given amount of retraction of the elongate member, due to displacement of the fluid in the reservoir by the plunger, and both the retraction of the elongate member and the delivery of a fluid composition may be effectuated by a single user motion (e.g., rotation of a wheel (210)). In some instances, full retraction of the elongate member may result in the delivery of between about 2 µl and about 9 µl of fluid. In some instances, full retraction of the elongate member may result in the delivery of between about 2 µl and 30 µl of fluid. In some of these instances, full retraction of the elongate member may result in the delivery of about 4.5 µl of fluid. In some of these instances, full retraction of the elongate member may result in the delivery of about 10 µl of fluid. As the elongate member is retracted, the delivery system (200) may produce audible and/or tactile clicks at increments. These clicks may, for example, be due to the ratcheting of the distal end of the linkage (230) distally relative to the linear gear (216). Each click may correspond to a fixed, predetermined volume of fluid, in some cases, between about 0.1 and about 1 µl.

In some variations, the delivery system (200) may be configured to allow for a fixed cumulative amount of extension and/or retraction of the slidable elongate member while the system is in the first configuration. The fixed cumulative amount of extension/retraction may correspond, for example, to the full circumference of Schlemm's canal, two full circumferences of Schlemm's canal, or any desired distance. Exemplary fixed cumulative amounts may be, but are not limited to, about 39 mm to about 41 mm, about 38 mm to about 40 mm, about 35 mm to about 45 mm, about 78 mm to about 82 mm, about 76 mm to about 80 mm, or about 70 mm to about 90 mm. The delivery systems may additionally or alternatively be configured to allow for a fixed cumulative delivery of fluid (e.g., in some variations about 20 µl of fluid).

For example, in one variation, the delivery system (200) may initially have the linear gear (216), elongate member, linkage (230), and reservoir (226) in their proximal-most locations within the housing (206). Rotation of a wheel (210) in a first direction may cause the linear gear (216) to move distally relative to the housing (206). This may cause the elongate member (250) to move distally out of the distal opening of the cannula (208) toward an extended position. In the first configuration the linkage (230) may be coupled via its distal end to the proximal portion (232) of the linear gear (216) having teeth (236) interfacing with the linkage (230), and thus, when the linear gear moves distally within the housing, the linkage may also move distally within the housing. Because the linkage (230) may be fixedly attached to the reservoir (226), the reservoir may also move distally within the housing. Rotation of a wheel (210) in a second, opposite direction may then cause the linear gear (216) to move proximally within the housing (206), but the linkage (230) and reservoir (226) may stay fixed relative to the housing, causing the distal end of the linkage to slide distally within the track (240) of the linear gear, and causing fluid to be delivered from the reservoir and out of the lumen of the elongate member (250). Repeated rotation of a wheel in the first and second directions (and thus repeated extension and retraction of the elongate member) may thus result in the distal end of the linkage (230) moving distally within the linear gear (216) with each cycle.

After a particular cumulative amount of advancement and retraction of the elongate member (250), the distal end of the linkage (230) may reach the distal end of the proximal portion (232) of the linear gear (i.e., the distal end of teeth (236)). It should be appreciated that in some variations of the delivery system, this cumulative amount of advancement and retraction may be achieved in a single cycle of advancement and retraction. In other variations of the delivery system, this cumulative amount of advancement and retraction may only be achieved through at least two cycles of advancement and retraction (since the total translation of the linkage relative to the linear gear in a single cycle may be limited to the maximum advancement distance of the elongate member). In these variations, the total length of the proximal portion (232) of the linear gear (216) may be the same distance that the linear gear travels between its distal-most and proximal-most positions, and is the same distance that the elongate member extends from its retracted to extended position. For example, the total length of the proximal portion (232) of the linear gear (216) may be approximately 20 mm. As such, the delivery system (200) may be configured such that the elongate member may be advanced a first time approximately halfway around Schlemm's canal (i.e., 180 degrees, or approximately 19 mm to about 20 mm) in a first direction, which may be the maximum amount that the elongate member may be advanced without retraction. The elongate member may then be fully retracted (during which fluid may be delivered). After this first extension, the reservoir (226) of the fluid assembly may have moved half of its maximum distance toward its distal position, its distance to the linear gear (216)

may have decreased by approximately half of its total possible decrease, and the distal end of the linkage (230) may be located at the halfway point of the linear gear (216)—that is, at the distal-most tooth (236) of the proximal portion (232) of the linear gear (216). The delivery system (200) may then be rotated about the handle, and the elongate member may be advanced a second time approximately halfway around Schlemm's canal in a second direction. The elongate member may then be retracted (during which fluid may be delivered). At the conclusion of the second extension, the reservoir (226) may be located at its distal-most position, its distance to the linear gear (216) may be at its minimum, and the distal end of the linkage (230) may be located at the distal-most position within the track (240) of the distal portion (234) of the linear gear (216). With the distal end of the linkage (230) in the distal portion (234) of the linear gear (216), the movement of the linear gear and elongate member may no longer be coupled to movement of the linkage or reservoir, and the elongate member may be repeatedly extended and retracted (without a cumulative limit) by repeated extension and retraction of the linear gear (216).

The delivery systems may be further configured such that the elongate member disrupts the trabecular meshwork. In some variations, the elongate member may be configured such that advancement and/or retraction of the elongate member may disrupt the trabecular meshwork, and the elongate member may comprise one or more features to promote disruption of the trabecular meshwork upon advancement or retraction, such as disruptive components on the distal end of the elongate member, such as barbs, hooks, balloons, or the like. In other variations, the elongate member may be configured such that the body of the elongate member is configured to cut or tear the trabecular meshwork.

For example, the delivery system may be configured such that the elongate member may be advanced out of the cannula and around Schlemm's canal; if the cannula is then removed from the eye without retracting the elongate member, the body of the elongate member may cut or tear the trabecular meshwork as the cannula is removed. The body of the elongate member may be configured to "unzip" the meshwork, cutting or tearing from a first location of the trabecular meshwork close to the cannula tip (i.e., at the proximal end of the elongate member) and continuing around the trabecular meshwork toward the distal end of the elongate member. The elongate member may be configured to apply a disruptive force to cut or tear the meshwork at one location of the meshwork at a time, sequentially around Schlemm's canal, rather than a disruptive force that simultaneously cuts or tears the meshwork throughout all of the trabecular meshwork being cut or torn.

II. KITS

The delivery systems described herein may be placed in specialized packaging. The packaging may be designed to protect the systems, and in particular, to protect the cannula. It may be desirable for the packaging to prevent contact between the distal tip of the cannula and any other object or surface. In order to do so, the packaging may comprise one or more elements configured to secure a delivery system to the packaging at one or more locations proximal to the distal tip of the cannula. Securing the delivery system at at least two locations proximal to the distal tip of the cannula may be desirable to limit the ability of the delivery system to pivot relative to the packaging.

Figure 10A:
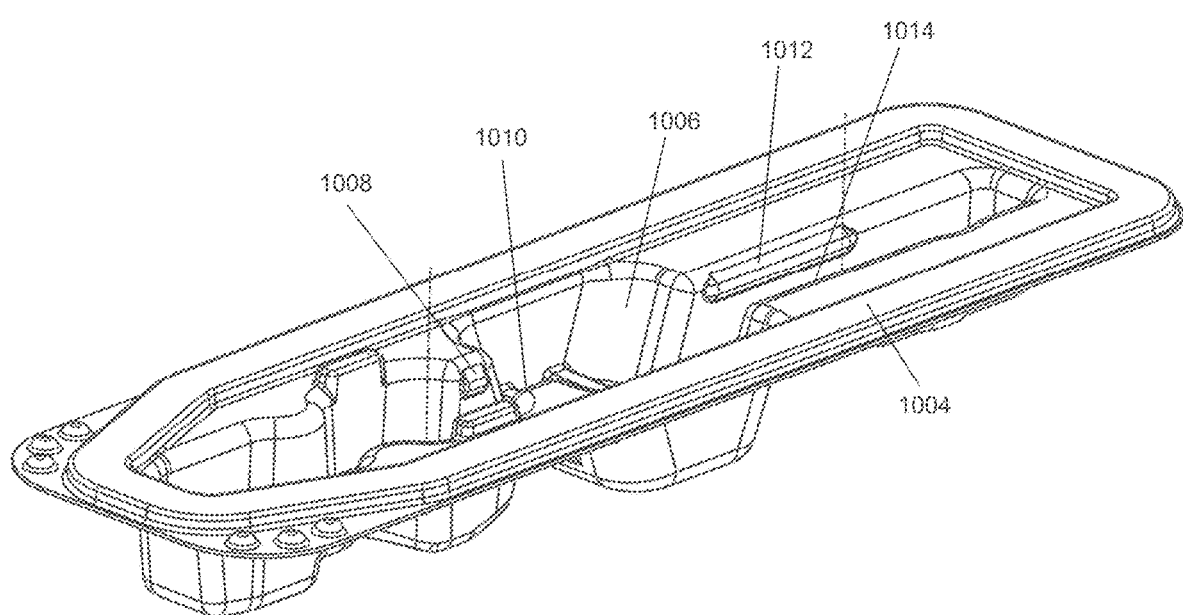
FIGS. 10A-10B show perspective views of an exemplary tray for a delivery system (FIG. 10A) and for a delivery system and loading tool (FIG. 10B).
Figure 10B:
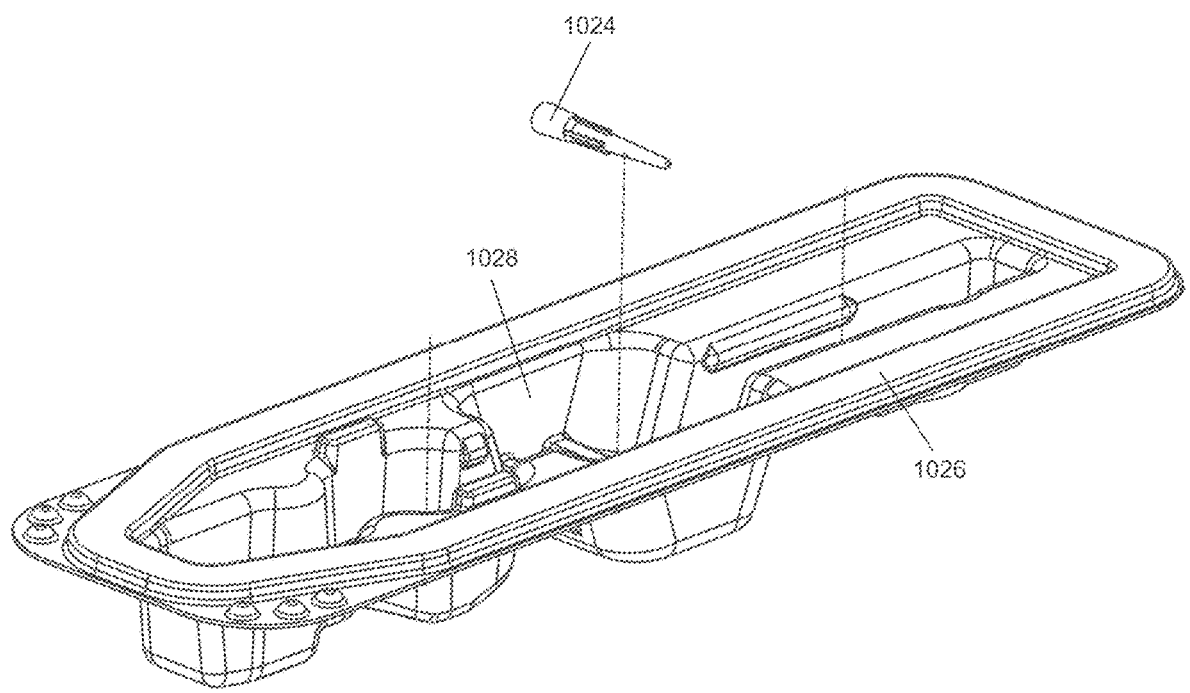
Figure 10C:
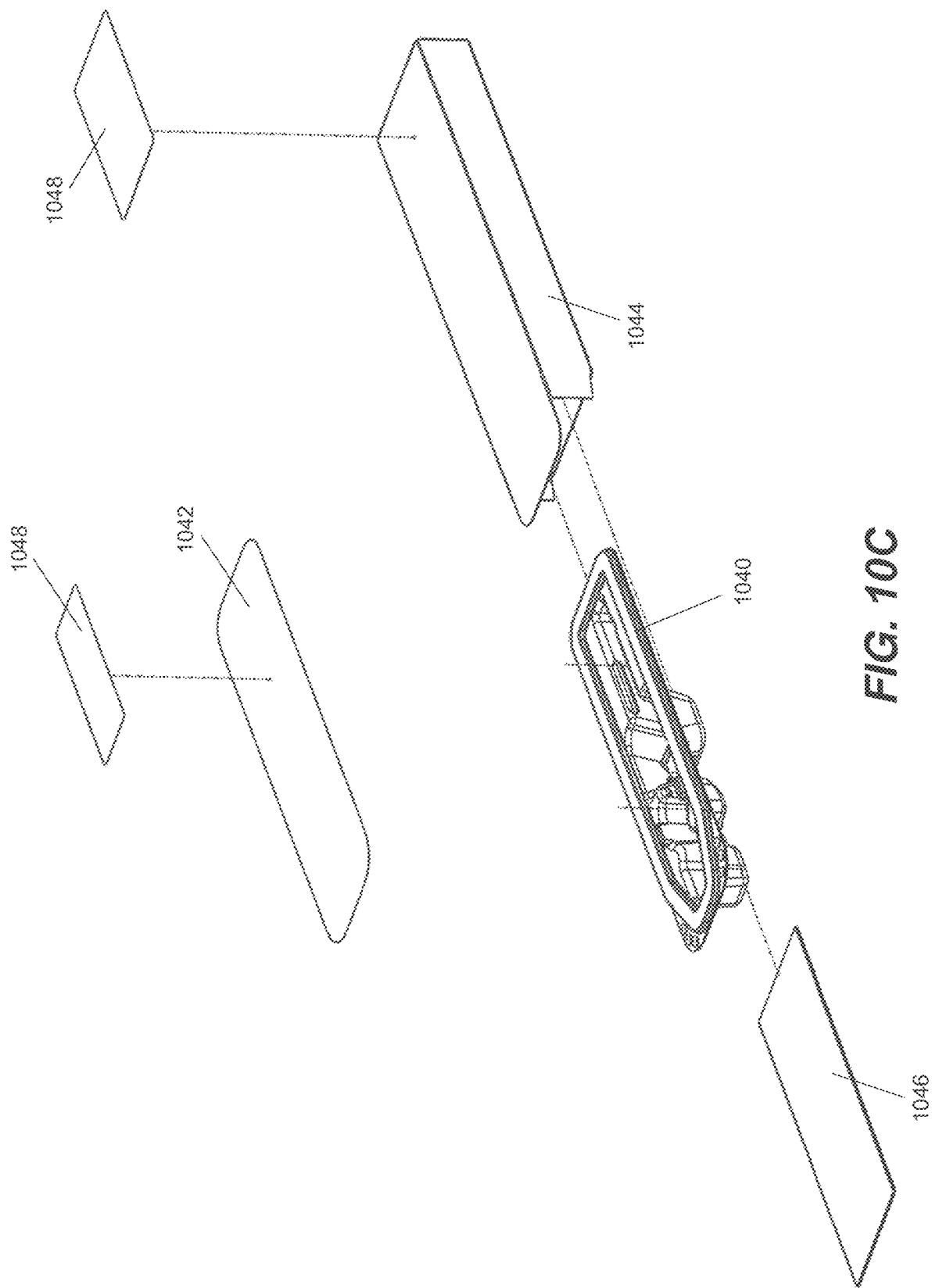
FIG. 10C shows an exploded view of exemplary packaging.

In one exemplary variation, the packaging may comprise a tray comprising a recess having a shape generally corresponding to the shape of the delivery system and comprising one or more pinch points configured to secure the delivery system at locations proximal to the cannula. FIG. 10A shows an exemplary tray (1004) for a delivery system (1000). Tray (1004) may comprise a recess (1006) configured to receive the delivery system. The tray (1004) may comprise first (1008) and second (1010) distal pinch points and first (1012) and second (1014) proximal pinch points configured to secure the delivery system within the recess (1006). When the delivery system is secured within the tray (1004), the cannula of the delivery system may be suspended such that the cannula is not in contact with the tray, and the pinch points may limit pivoting of the delivery system in a way that could cause the cannula to come into contact with the tray. The pinch points may be configured to safely secure the delivery system within the tray (1004), while also allowing a user to remove the delivery system from the tray in a controlled fashion. In variations in which the kits described here comprise additional components, the packaging may be designed to hold these additional components. For example, FIG. 10B shows an exemplary tray (1026) comprising a recess (1028) configured to hold a loading tool (1024) and a delivery system. As shown in FIG. 10C, a tray (1040) may be configured to be sealed with a lid (1042) (e.g., heat sealed) and placed within a box (1044). The box (1044) may optionally further contain instructions for use (1046). The lid (1042) and/or box (1044) may optionally have labels (1048) affixed thereto.

It should be appreciated that the packaging may have other configurations that protect the distal tip of the cannula. For example, in another variation, the packaging may comprise a stiff planar sheet to which the delivery system may be attached in an orientation such that the cannula is not in contact with the planar sheet. The delivery system may be attached (e.g., via ties or other materials wrapped around the housing) at two or more points along the housing in order to prevent movement of the delivery system relative to the planar sheet. It may be desirable to protect the cannula on at least two sides; for example, a portion of the planar sheet near the cannula may be bent around the cannula to protect the cannula on at least two sides, or a second stiff planar sheet may be attached to the delivery system opposite the first planar sheet.

Some kits described herein may comprise multiple delivery systems. For example, a kit may comprise two delivery systems. In some variations, the kit may comprise two of the same system, such that, for example, the first delivery system may be used in a first eye of the patient and the second delivery system may be used in the second eye of the patient. Kits comprising multiple systems may be packaged in any suitable way, such as in a stacked configuration or side-by-side configuration.

Some kits may comprise ocular implants in addition to one or more delivery systems as described herein. For example, a kit may comprise one or more devices configured to be implanted into Schlemm's canal, which may be generally configured to maintain the patency of Schlemm's canal without substantially interfering with transmural fluid flow across the canal. The kits may comprise one or more ocular implants such as, but not limited to, stents for placement in Schlemm's canal. In some variations, the ocular implants may be one or more of those disclosed in U.S. Pat. Ser. No. 7,909,789, which was previously incorporated by reference in its entirety, and U.S. Pat. Ser. No. 8,529,622, which was previously incorporated by reference in its entirety.

III. METHODS

Methods for treating conditions of the eye using the systems described above are also provided. In some variations, the methods of treating conditions of the eye comprise dilating Schlemm's canal and tearing the trabecular meshwork using a single delivery system. In some instances, treating conditions of the eye may result in increased aqueous humor drainage, reduced resistance to aqueous outflow, and/or reduced intraocular pressure. Some methods described herein may dilate Schlemm's canal, dilate the collector channels, and/or break any septae that may obstruct circumferential flow through Schlemm's canal. Dilation of Schlemm's canal may disrupt obstructed inner walls of the canal, stretch the trabecular meshwork, and/or increase the trabecular meshwork's porosity. This may improve the natural aqueous outflow pathway. The dilation may be performed by delivery of a fluid composition (e.g., a viscoelastic fluid as described herein). Some methods described here may comprise performing a trabeculotomy to cut trabecular meshwork. Some methods described here may comprise implanting an ocular device within Schlemm's canal. In some instances, the systems described herein may be used in performing ab-interno trabeculotomy, ab-interno transluminal trabeculotomy, clear corneal trabeculotomy, clear corneal transluminal trabeculotomy, ab-interno canaloplasty, and/or clear corneal canaloplasty.

The methods are generally single-handed, single-operator controlled methods that are minimally invasive, e.g., they are tailored for an ab-interno procedure, which as previously mentioned, can be advantageous over the more invasive ab-externo approach. However, use of the ocular systems in an ab-externo method may be contemplated in some instances and thus, are not excluded here. The methods may be used to treat or prevent glaucoma, pre-glaucoma, or ocular hypertension. When treating glaucoma, the methods may also be used in conjunction with a cataract surgery (before or after) using the same incision during the same session or at another time.

Some of the methods, described in more detail below, may comprise dilating Schlemm's canal and/or aqueous collector channels (e.g., with viscoelastic fluid) using the delivery systems described herein. The methods may also comprise tearing or cutting the trabecular meshwork of Schlemm's canal. These methods may be carried out separately, or they may be combined into a single procedure. For example, in some instances a portion (e.g., half) of Schlemm's canal may be dilated (using a fluid composition, for example), and the trabecular meshwork of the same or a different portion of Schlemm's canal may be torn or cut, within the same eye. As another example, all of Schlemm's canal may be dilated, and then all or a portion of the trabecular meshwork may subsequently be torn or cut. This may be desirable, for example, in order to both dilate the collector channels and tear or cut the trabecular meshwork.

In some of these variations, dilation and tearing or cutting may be performed using a single delivery system, such as one described herein configured to deliver a fluid composition. For example, the elongate member of a delivery system configured to deliver a fluid composition may first be used to deliver a fluid composition to a portion of Schlemm's canal (e.g., about an 180 degree arc of the canal, about a 90 degree arc of the canal) as described herein, and subsequently to tear or cut the trabecular meshwork in the same portion of the canal as described herein. As another example, the elongate member of a delivery system configured to deliver a fluid composition may first be used to deliver a fluid composition to a portion of Schlemm's canal (e.g., about an 180 degree arc of the canal, about a 90 degree arc of the canal, etc.) and subsequently to tear or cut the trabecular meshwork in another portion of the canal (e.g., the other about-180 degree arc, another 90 degree arc, etc.). As yet another example, the elongate member of a delivery system configured to deliver a fluid composition may first be used to deliver fluid composition to all of Schlemm's canal (e.g., by delivering about 180 degrees of fluid composition in a first direction and then delivering about 180 degrees of fluid composition in a second direction), and then subsequently to tear or cut the full 360 degrees of trabecular meshwork (e.g., by tearing or cutting about 180 degrees of trabecular meshwork in a first direction and then tearing or cutting about 180 degrees of trabecular meshwork in a second direction). As yet another example, the elongate member of a delivery system configured to deliver a fluid composition may first be used to deliver fluid composition to all of Schlemm's canal in one step (i.e., by delivering about 360 degrees of fluid composition to Schlemm's canal in a single direction), and then subsequently to tear or cut the full 360 degrees of trabecular meshwork in a single step (i.e., by tearing or cutting about 360 degrees of trabecular meshwork in a single direction).

In other variations, dilation and tearing or cutting may be performed using different delivery systems (e.g., the dilation may be performed using a delivery system configured to deliver a fluid composition, and the tearing or cutting may be performed using a delivery system not configured to deliver a fluid). As yet another example, in some instances dilation may be performed in one eye of a patient, while the trabecular meshwork may be torn or cut in the other eye of the patient.

Procedures comprising dilating Schlemm's canal and/or tearing or cutting the trabecular meshwork may also be combined with procedures delivering an ocular device, either in the same eye or in a different eye of the same patient. For example, all or a portion of Schlemm's canal may be dilated, followed by insertion of an ocular device. As another example, a portion of the trabecular meshwork may be torn or cut, while an ocular implant may be delivered to another portion of Schlemm's canal. As yet another example, a portion of Schlemm's canal may be dilated, while an ocular implant may be delivered to another portion of Schlemm's canal. As yet another example, an ocular implant may be delivered to a portion of Schlemm's canal, and then Schlemm's canal may be subsequently dilated to improve the function of the ocular implant.

Any suitable ocular device that maintains the patency of Schlemm's canal or improves outflow of aqueous humor may be implanted. For example, ocular devices that maintain the patency of Schlemm's canal without substantially interfering with fluid flow across, along, or out of the canal may be implanted. Such devices may comprise a support having at least one fenestration, as disclosed in U.S. Pat. No. 7,909,789, and U.S. Pat. No. 8,529,622, which were previously incorporated by reference in their entirety. Ocular devices that disrupt the juxtacanalicular trabecular meshwork or adjacent inner wall of Schlemm's canal may also be implanted. In addition to ocular devices made from metal or metal alloys, the use of sutures, modified sutures, modified polymers, polymeric filaments, or solid viscoelastic structures may be delivered.

Fluid Composition Delivery

Some methods described herein may comprise delivering fluid composition into the eye, such as into Schlemm's canal. The methods may generally include the steps of creating an incision in the ocular wall (e.g., the sclera or cornea) that provides access to the anterior chamber of the eye; advancing a cannula of the delivery system through the incision and at least partially across the anterior chamber to the trabecular meshwork; accessing Schlemm's canal with the cannula; and delivering the fluid composition into the canal using a elongate member slidable within the cannula lumen. The cannula may be configured to include a proximal end and a distal curved portion, where the distal curved portion has a proximal end, a distal end, and a radius of curvature defined between the ends. Here the cannula may also include a body and a distal tip having a bevel that directly engages the radius of curvature, e.g., it is contiguous with the radius of curvature. Further advantageous cannula features may also be included, which are described above. The method may also include the step of flushing the system with fluid (e.g., to remove air from the system) and/or the step of irrigating the operative field to clear away blood or otherwise improve visualization of the field.

In some methods, an elongate member comprising a lumen may be advanced into Schlemm's canal and the fluid composition may be delivered via the elongate member. The elongate member and/or fluid delivery may dilate Schlemm's canal, and fluid delivery may additionally dilate the collector channels. The entire length of Schlemm's canal or a portion thereof may be dilated by the fluid. For example, at least 75%, at least 50%, at least 25%, at least 10% of the canal, or at least 1% of the canal may be dilated. The fluid compositions may also be delivered to treat various medical conditions of the eye, including but not limited to, glaucoma, pre-glaucoma, anterior or posterior segment neovascularization diseases, anterior or posterior segment inflammatory diseases, ocular hypertension, uveitis, age-related macular degeneration, diabetic retinopathy, genetic eye disorders, complications of cataract surgery, vascular occlusions, vascular disease, or inflammatory disease.

The surgeon may first view the anterior chamber and trabecular meshwork (with underlying Schlemm's canal) using an operating microscope and a gonioscope or gonioprism. Using a 0.5 mm or greater corneal, limbal, or sclera incision, the surgeon may then gain access to the anterior chamber. A saline solution or viscoelastic composition may then be introduced into the anterior chamber to prevent its collapse. Here the saline solution or viscoelastic composition may be delivered through the delivery system cannula or by another mode, e.g., by infusion through an irrigating sleeve on the cannula. The surgeon, under direct microscopic visualization, may then advance the cannula of the delivery system through the incision towards the anterior chamber angle. When nearing the angle (and thus the trabecular meshwork), the surgeon may apply a gonioscope or gonioprism to the cornea to visualize the angle. The application of a viscous fluid (e.g., a viscoelastic composition as previously described) to the cornea and/or gonioscope or gonioprism may help to achieve good optical contact and negate total internal reflection thereby allowing visualization of the anterior chamber angle. As the surgeon visualizes the trabecular meshwork, the cannula may then be advanced so that the bevel of at the distal end of the curved distal portion of the cannula pierces the meshwork and is in communication with the lumen of Schlemm's canal.

Next, a slidable elongate member coaxially disposed within the cannula lumen may be advanced into the canal under gonioscopic visualization. The elongate member may be advanced any suitable amount and direction about the canal. For example, the elongate member may be advanced between about 1 degree and about 360 degrees about the canal, between about 10 degrees and about 360 degrees about the canal, between about 150 and about 210 degrees about the canal, or any suitable distance, about 360 degrees about the canal, about 270 degrees about the canal, about 180 degrees about the canal, about 120 degrees about the canal, about 90 degrees about the canal, about 60 degrees about the canal, about 30 degrees about the canal, or about 5 degrees about the canal. In some variations, the elongate member may be advanced in two steps, e.g., first in a clockwise direction (e.g., about 180 degrees, about 90 degrees, etc.) and second in a counterclockwise direction (e.g., about 180 degrees, about 90 degrees, etc.) about the canal (e.g., to thereby achieve a 360 or 180 degree ab-interno viscocanalostomy or canaloplasty). In some variations, the elongate member may be advanced in one step (e.g., about 90 degrees in a clockwise direction, about 180 degrees in a clockwise direction, about 270 degrees in a clockwise direction, about 360 degrees in a clockwise direction, about 90 degrees in a counterclockwise direction, about 180 degrees in a counterclockwise direction, about 270 degrees in a counterclockwise direction, about 360 degrees in a counterclockwise direction) about the canal to thereby achieve a corresponding degree ab-interno viscocanalostomy or canaloplasty. Fluid may be injected upon advancement or retraction of the elongate member. Once the slidable elongate member has been positioned within the canal, a fluid composition, e.g., a viscoelastic solution, may be continuously or intermittently delivered through the lumen of the elongate member. The fluid composition may exit the lumen of the elongate member through its distal end (e.g., the through the distal tip), or through openings or fenestrations provided along its shaft, or a combination of both. The openings or fenestrations may be spaced along the axial length of the elongate member in any suitable manner, e.g., symmetrically or asymmetrically along its length. Other substances such as drugs, air, or gas may delivered be in the same manner if desired.

In some variations, the slidable elongate member may be repositioned by retraction or repeated advancement and retraction. In some variations of the method, the same or different incision may be used, but the delivery system cannula is employed to access and dilate Schlemm's canal from a different direction (e.g., counterclockwise instead of clockwise). Once a sufficient amount of fluid has been delivered, the surgeon may retract the slidable elongate member into the cannula and remove the delivery system from the eye. It should be appreciated that the cannulas described here may be specifically manufactured to comprise a dual-surface configuration at the distal tip (i.e., sharp and smooth surfaces), which may allow the elongate member to be advanced, repositioned, and/or retracted without severing it on the distal tip of the cannula. It should also be understood that these steps may be used alone or in combination with cataract surgery (in one sitting).

Some of the delivery systems described herein may be configured such that the cumulative amount of advancement and/or retraction of the slidable elongate member is limited. For example, as described above, after the elongate member is advanced and retracted a particular cumulative distance (e.g., about 39 mm to about 40 mm each of advancement and retraction, corresponding to the approximate circumference of Schlemm's canal; or about 78 mm to about 80 mm each of advancement and retraction, corresponding to approximately twice the circumference of Schlemm's canal; or any other suitable distance), it may no longer be able to be advanced. This advancement and retraction may occur over multiple advancement-retraction cycles. For example, the elongate member may be advanced about 20 mm, then retracted by about 20 mm, then advanced by about 20 mm, then retracted by about 20 mm. When the cumulative distance is limited to about 40 mm, after these two cycles of advancement and retraction, the elongate member may no longer be able to be advanced. In other variations, the delivery systems may not limit the cumulative amount of advancement and/or retraction of the elongate member.

In some variations of the ab-interno method, the fluid composition may be delivered simultaneously with retraction of the elongate member (i.e., the fluid compositions may be delivered in a manner where retraction of a system component allows advancement of the fluid out of the system cannula). It should be understood that the delivery systems may be configured so that the fluid compositions are delivered continuously, passively, automatically, or actively by the surgeon. The fluid compositions may also be delivered to the canal independent of the gear shaft movement with a pump or auxiliary plunger. In some variations, retraction of the elongate member may correspond to a fixed volume of fluid composition being delivered via the lumen of the elongate member. The fluid composition may be delivered via the distal opening of the lumen of the elongate member as it is retracted, and thus, the fluid may be evenly delivered throughout the portion of the canal through which the elongate member was advanced.

The fluid compositions that may be delivered by the systems described herein include but are not limited to saline and viscoelastic fluids. The viscoelastic fluids may comprise hyaluronic acid, chondroitin sulfate, cellulose, derivatives or mixtures thereof, or solutions thereof. In one variation, the viscoelastic fluid comprises sodium hyaluronate. In another variation, the viscoelastic composition may further include a drug. For example, the viscoelastic composition may include a drug suitable for treating glaucoma, reducing or lowering intraocular pressure, reducing inflammation, fibrosis neovascularization or scarring, and/or preventing infection. For example, in some variations, the viscoelastic composition may include the therapeutic agents described herein, such as but not limited to Rho kinase (ROCK) inhibitors and agents for gene therapy, DNA, RNA, or stem cell-based approaches.

The viscoelastic composition may also include agents that aid with visualization of the viscoelastic composition. For example, dyes such as but not limited to fluorescein, trypan blue, or indocyanine green may be included. In some variations, a fluorescent compound or bioluminescent compound is included in the viscoelastic composition to help with its visualization. In other variations, the system may deliver the drug alone, without the viscoelastic composition. In this case, the drug may be loaded onto or into a sustained release biodegradable polymer that elutes drug over a period of weeks, months, or years. It is also contemplated that air or a gas could be delivered with the systems, as described herein.

Other variations of the ab-interno method include the use of an endoscope. Similar to the method described directly above, access to the anterior chamber is first made by incising the cornea, limbus, or sclera. Again, this may be done in combination with cataract surgery in one sitting, either before or after cataract surgery, or independently. The anterior chamber may be infused with saline solution or a viscoelastic composition may be placed in the anterior chamber to prevent its collapse. The saline or viscoelastic may be delivered as a separate step or it may be infused with the elongate member of the delivery system, an irrigating sleeve on the elongate member or cannula, or with a separate infusion cannula. The surgeon, under direct microscopic visualization, then advances the endoscope through the incision and towards the angle and trabecular meshwork. As the surgeon visualizes the trabecular meshwork via the endoscope or any associated display, the bevel of the cannula is advanced to pierce the meshwork. The elongate member is then advanced under endoscopic visualization. The elongate member may be advanced any suitable amount and direction about the canal. For example, the elongate member may be advanced between about 10 degrees to about 360 degrees about the canal, or it may be advanced in two steps, e.g., 180 degrees in a clockwise direction and 180 degrees in a counterclockwise direction about the canal (to thereby achieve a full 360 degree ab-interno viscocanalostomy). Once the elongate member has been positioned within the canal, a fluid composition, e.g., a viscoelastic fluid, may be continuously or intermittently delivered through the lumen of the elongate member. The fluid composition may exit the lumen of the elongate member through its distal end (e.g., the through the distal tip), or through openings or fenestrations provided along its shaft, or a combination of both. The openings or fenestrations may be spaced along the axial length of the elongate member in any suitable manner, e.g., symmetrically or asymmetrically along its length. Other substances such as drugs, air, or gas may be delivered in the same manner if desired. The elongate member may be repositioned by retraction or repeated advancement and retraction. In some variations of the method, the same or different incision may be used, but the delivery system cannula is employed to access and dilate Schlemm's canal from a different direction (e.g., counterclockwise instead of clockwise). Once a sufficient amount of fluid has been delivered, the surgeon may retract the slidable elongate member into the cannula. In some variations the surgeon may then remove the delivery system from the eye; in other variations the surgeon may keep the delivery system within the eye and perform a trabeculotomy, as described in more detail herein.

More generally, in methods described herein, exemplary volumes of viscoelastic fluid that may be delivered may in some instances be between about 1 µl and about 200 µl, or in some instances be between about 1 µl and about 100 µl. In some instances, sufficient volumes to provide a disruptive force may range from about 1 µl to about 50 µl, from about 1 µl to about 30 µl or from about 2 µl to about 16 µl. In one variation, a volume of about 4 µl is sufficient to disrupt Schlemm's canal and/or the surrounding tissues. In other variations, the volume of viscoelastic fluid sufficient to disrupt trabeculocanalicular tissues may be about 2 µl, about 3 µl, about 4 µl, about 5 µl, about 6 µl, about 7 µl, about 8 µl, about 9 µl, about 10 µl, about 11 µl, about 12 µl, about 13 µl, about 14 µl, about 15 µl, about 16 µl, about 17 µl, about 18 µl, about 19 µl, about 20 µl, about 25 µl, about 30 µl, about 35 µl, about 40 µl, about 45 µl, or about 50 µl.

Tissue disruption may occur by viscodilating excessively and intentionally with at least about 1 µl, at least about 2 µl, at least about 3 µl, at least about 4 µl, at least about 5 µl, at least about 6 µl, at least about 7 µl, at least about 8 µl, at least about 9 µl, at least about 10 µl, at least about 11 µl, at least about 12 µl, at least about 13 µl, at least about 14 µl, at least about 15 µl, at least about 16 µl, at least about 17 µl, at least about 18 µl, at least about 19 µl, or at least about 20 µl of viscoelastic fluid per 360 degree arc of the canal. In some variations, at least about 20 µl, at least about 25 µl, at least about 30 µl, at least about 35 µl, at least about 40 µl, at least about 45 µl, or at least about 50 µl of viscoelastic fluid may be delivered.

Depending on factors such as the type or severity of the condition being treated, the disruptive force may be generated to partially or completely destroy and/or remove the trabecular meshwork, and may be adjusted by varying the volume of viscoelastic fluid delivered.

Additionally, the fluid compositions may be delivered to restore the tubular anatomy of Schlemm's canal, to clear obstructions within the canal, to disrupt juxtacanalicular trabecular meshwork or the inner wall of Schlemm's canal within the canal, or to expand the canal. Here the delivery systems may include wires, tubes, balloons, instruments that deliver energy to the tissues, and/or other features to help with these methods. It is contemplated that glaucoma may be treated using such systems with additional features. The surface of these systems may also be roughened or have projections to further disrupt the inner wall of Schlemm's canal and juxtacanalicular trabecular meshwork to enhance aqueous humor outflow or permeability. Additionally, it should be appreciated that the delivery systems described herein may be used to deliver the fluid compositions to the anterior chamber or anterior segment.

The viscoelastic fluid may be delivered while advancing the elongate member of a single-handed, single-operator controlled device from Schlemm's canal in the clockwise direction, counterclockwise direction, or both, or during withdrawal of the elongate member from Schlemm's canal. As previously stated, the viscoelastic fluid may be delivered to disrupt Schlemm's canal and surrounding trabeculocanalicular tissues. For example, the delivered viscoelastic fluid may cause disruption by dilating Schlemm's canal, increasing the porosity of the trabecular meshwork, stretching the trabecular meshwork, forming microtears or perforations in juxtacanalicular tissue, removing septae from Schlemm's canal, dilating collector channels, or a combination thereof. The elongate member may be loaded with the viscoelastic fluid at the start of an ocular procedure so that the fluid can be delivered by a single device. This is in contrast to other systems that use forceps or other advancement tool to advance a fluid delivery catheter into Schlemm's canal and/or devices containing viscoelastic fluid that are separate or independent from a delivery catheter or catheter advancement tool, and which require connection to the delivery catheter or catheter advancement tool during a procedure by an assistant while the delivery catheter or catheter advancement tool is held by the surgeon.

Trabeculotomy

The methods described herein may comprise performing a trabeculotomy. The methods (as well as systems and devices) described herein, including the method for providing a disruptive force to trabeculocanalicular tissues, may be highly suitable for ab-interno trabeculotomy and goniotomy given that they avoid the use of electrocautery, and are capable of advancing elongate members over larger degrees of arc of Schlemm's canal. In some instances, disruptive tools may comprise disruptive components on their distal portions. Exemplary disruptive components include, without limitation, notches, hooks, barbs, balloons, or combinations thereof. In other instances, the disruptive tools may not comprise disruptive components on their distal portions, and indeed may have atraumatic blunt distal portions. Exemplary atraumatic distal portions include, without limitation, parasol or dome shaped distal portions.

The outer diameter of the elongate member or tool may be variously sized for disruption of tissues, analogous to how fluid volumes may be varied to vary the level of disruption. For example, an elongate member or tool having an outer diameter ranging from about 50 to about 100 microns may be advanced through the canal to slightly dilate the canal and break or remove septae obstructing circumferential canalicular flow. An elongate member or tool having an outer diameter ranging from about 100 to 200 microns may be employed to perform the foregoing, and may also to begin to stretch the trabecular meshwork and juxtacanalicular tissues. An elongate member or tool having an outer diameter ranging from about 200 to about 300 microns may be able to perform the above, but may also create microtears in the trabecular meshwork and juxtacanalicular tissues, and may maximally dilate the collector channels. An elongate member or tool having an outer diameter ranging from about 300 to about 500 microns may maximally disrupt the tissues and may create tears or perforations all along the trabecular meshwork and juxtacanalicular tissues. The elongate member or tool may be advanced out from the tip of the cannula and into the canal about a 30 degree arc of the canal (e.g., advanced about 3 to 4 mm out of the cannula), advanced about a 60 degree arc of the canal (e.g., advanced about 6 to 8 mm out of the cannula), advanced about a 90 degree arc of the canal (e.g., advanced about 10 mm out of the cannula), advanced about a 120 arc of the canal (e.g., advanced about 15 mm out of the cannula), advanced about a 180 degree arc of the canal (e.g., advanced about 20 mm out of the cannula), or advanced about a full 360 degrees of the canal (e.g., advanced about 36 to 40 mm out of the cannula), for maximal intraocular pressure reduction. In some variations, the elongate member may have a non-uniform outer diameter. For example, the elongate member may have a tapered outer diameter, such that the outer diameter increases from the distal to proximal end.

In some variations, the methods disclosed herein may include advancement of the elongate member between about a 5 degree arc of Schlemm's canal and about a 360 degree arc. In some variations, the methods may include advancement of the elongate member (or tool) about a 360 degree arc of Schlemm's canal, about a 270 degree arc of Schlemm's canal, about a 120 degree arc of Schlemm's canal, about a 180 degree arc of Schlemm's canal, or about a 90 degree arc of Schlemm's canal. In yet further variations, advancement of the elongate member (or a tool) may be about a 0 to 5 degree arc of Schlemm's canal, about a 30 degree arc of Schlemm's canal, or about a 60 degree arc of Schlemm's canal. Advancement may occur from a single access point in Schlemm's canal or from multiple access points in the canal. It may be beneficial to advance the elongate member in both clockwise and counterclockwise directions about a 180 degree arc of Schlemm's canal from a single access point in the canal. In other variations, the elongate member may be advanced in a single (clockwise or counterclockwise) direction about 360 degrees of Schlemm's canal from a single access point in the canal.

Depending on factors such as the type or severity of the condition being treated, the disruptive force may be generated to partially or completely destroy and/or remove the trabecular meshwork, and may be adjusted by varying the tool configuration. In some methods, the trabecular meshwork may be disrupted during advancement of the slidable elongate member. Customizing a body segment of the elongate member proximal to the tip with one or more notches, barbs, or balloons that catch the meshwork as the distal tip is being guided and advanced along Schlemm's canal may also be used, thereby disrupting, partially tearing, fully tearing, and/or removing trabecular meshwork upon advancement. Additionally, an implant with edges specifically designed to cut the meshwork may be used.

In yet other methods, the trabecular meshwork may be disrupted during retraction of the slidable elongate member. The methods for disrupting tissues may involve customizing the system (e.g., the elongate member, any catheters or wires, probe tips, etc.) to catch or grasp the meshwork upon retraction after advancement through the canal. This may be done using a wire with a bent tip, hook, notch, or barb on its end that is advanced through the lumen of the catheter that then snags the meshwork upon retraction, tearing it along its length or removing it altogether, or solely with a metal or polymer wire or suture (no catheter) whose tip (and/or body) is hooked, notched, or barbed in such a way that it can be advanced into Schlemm's canal without tearing the meshwork but snags the meshwork upon retraction, tearing the meshwork and/or removing it completely. The elongate member may be provided with a disruptive tool, e.g., a sharp-edged element, that can cut or tear the trabecular meshwork while being retracted into the cannula, which is held stationary. Exemplary sharp-edged elements may be a hook, wire, or any other suitable shape memory component that can extend from the cannula to tear, cut, or remove trabecular meshwork.

Another method for disrupting tissues may include using oversized elongate members (e.g., having an outside diameter of 300-500 microns) to tear the meshwork upon delivery, or inflating or expanding the elongate member once it has been fully advanced into Schlemm's canal to stretch, disrupt, rupture, or fully tear the meshwork. For example, a catheter/elongate member, probe, or wire (with or without a lumen) whose tip is 200-250 microns in outer diameter, but having a shaft that begins to flare outwards after 3 clock hours of Schlemm's canal (i.e., at about the 5 or 10 mm mark on the catheter/elongate member) up to about 300, up to about 400, or up to about 500 microns, may be used, so that as the tip advances comfortably within Schlemm's canal, the enlarged shaft trails behind and ruptures the trabecular meshwork as it is advanced.

In another method, cutting, destruction, removal, or the like of the trabecular meshwork may be accomplished by removing the cannula from the eye while leaving the elongate member in the canal, thereby tearing through the meshwork. For example, a cannula may be inserted into the anterior chamber and Schlemm's canal, and a tool (e.g., a slidable elongate member) may be advanced within the canal. The cannula may be removed from the anterior chamber without retracting the elongate member. This action by itself may tear the trabecular meshwork. As the cannula is removed from the anterior chamber, the elongate member may begin tearing the trabecular meshwork from the point at which the cannula was inserted into Schlemm's canal, and may continue tearing around the trabecular meshwork toward the distal end of the elongate member.

The methods described here may be used to access the trabecular outflow system using a single clear corneal incision, and may allow for transluminal trabeculotomy of up to 360 degrees. The method may use a flexible elongate member that may be advanced and retracted using a single-handed disposable manual instrument. In one variation of the method, the cannula may be held securely against the angle while the flexible elongate member is advanced into Schlemm's canal. An exposed portion of one or more of the wheels may be rotated proximally to advance the flexible elongate member up to about 180 degrees around Schlemm's canal (about 20 mm of circumferential canal travel). For example, the elongate member may be advance about 90, 135, or 180 degrees. At this point, the flexible elongate member may in some instances be fully extended, and the wheel may no longer be able to be rotated. During this procedure, direct microscopic or gonioscopic visualization of the cannula tip may be maintained, and the anterior chamber may be maintained with viscoelastic or continuous balanced salt solution infusion. Once the flexible elongate member is advanced, the cannula may be removed from the eye through the incision without retracting the flexible elongate member. This may cause the body of the flexible elongate member to tear or cut through the trabecular meshwork. In some instances, it may be desirable to bias the distal tip of the cannula toward the trabecular meshwork being cut; this may in some instances help to prevent the flexible elongate member from slipping out of the canal during cannula removal.

Exemplary Combined Method with Fluid Composition Delivery and Trabeculotomy

Some of the methods described herein may comprise delivering fluid composition into the eye, such as into Schlemm's canal, and tearing or cutting the trabecular meshwork. For example, one variation of the methods described here may be carried out using the delivery system (200) of FIGS. 2A-2I. The method may allow for single-handed, manually operated delivery of fluid (e.g., viscoelastic fluid or gel) into Schlemm's canal via a slidable elongate member comprising a lumen (e.g., a microcatheter). The delivery of viscoelastic fluid may be metered, such that controlled, small amounts of viscoelastic can be delivered to the eye. The method may allow for catheterization and transluminal viscodilation of up to 360 degrees of Schlemm's canal, as well as trabeculotomy of up to 360 degrees of trabecular meshwork, using a single clear corneal incision for access. This method may, for example, reduce intraocular pressure in patients with glaucoma (e.g., open-angle glaucoma).

Figure 11A:
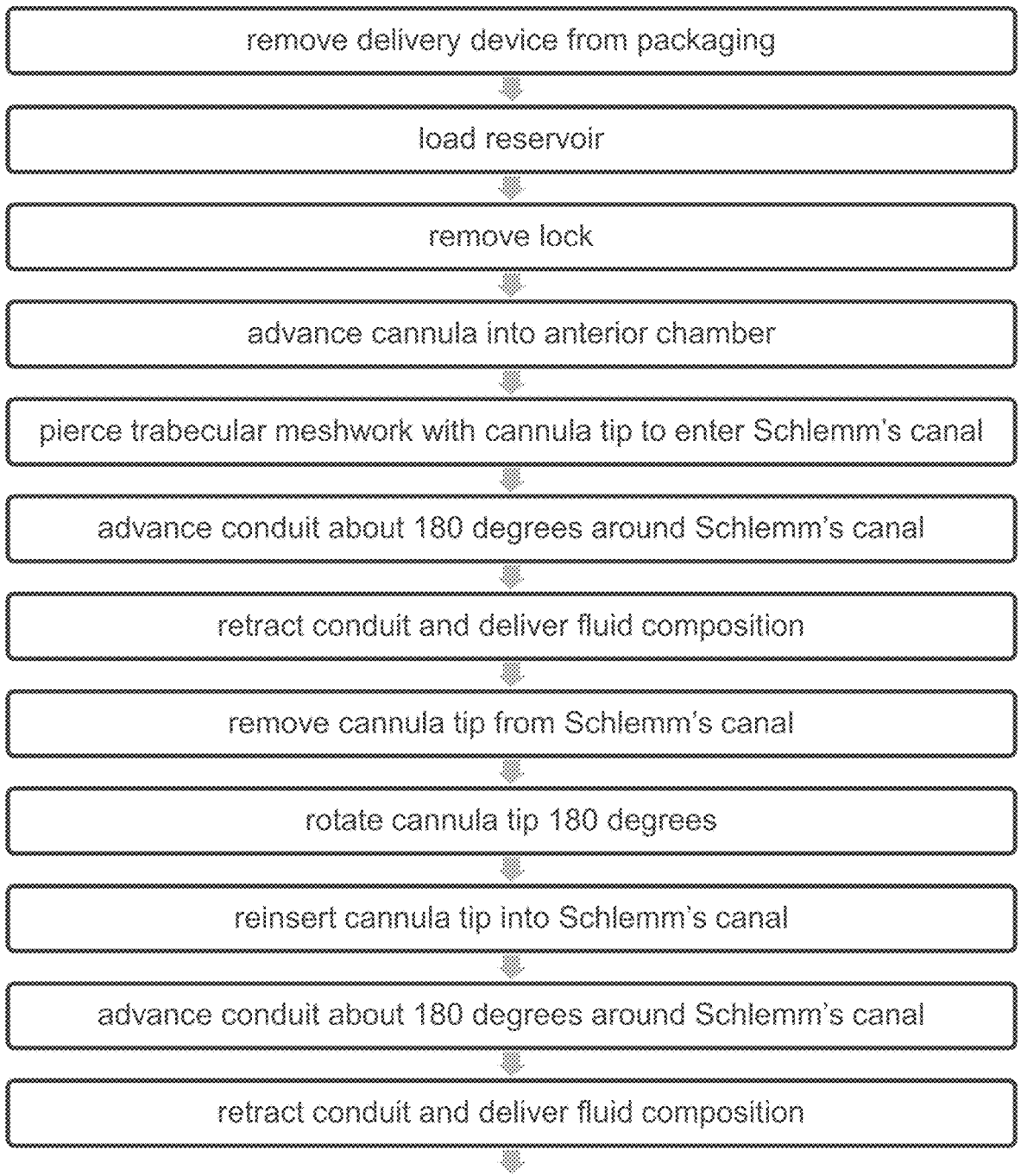
FIGS. 11A-11B show a flow-chart illustrating an exemplary method for delivering a fluid to Schlemm's canal (FIG. 11A) and tearing the trabecular meshwork (FIG. 11B).
Figure 11B:
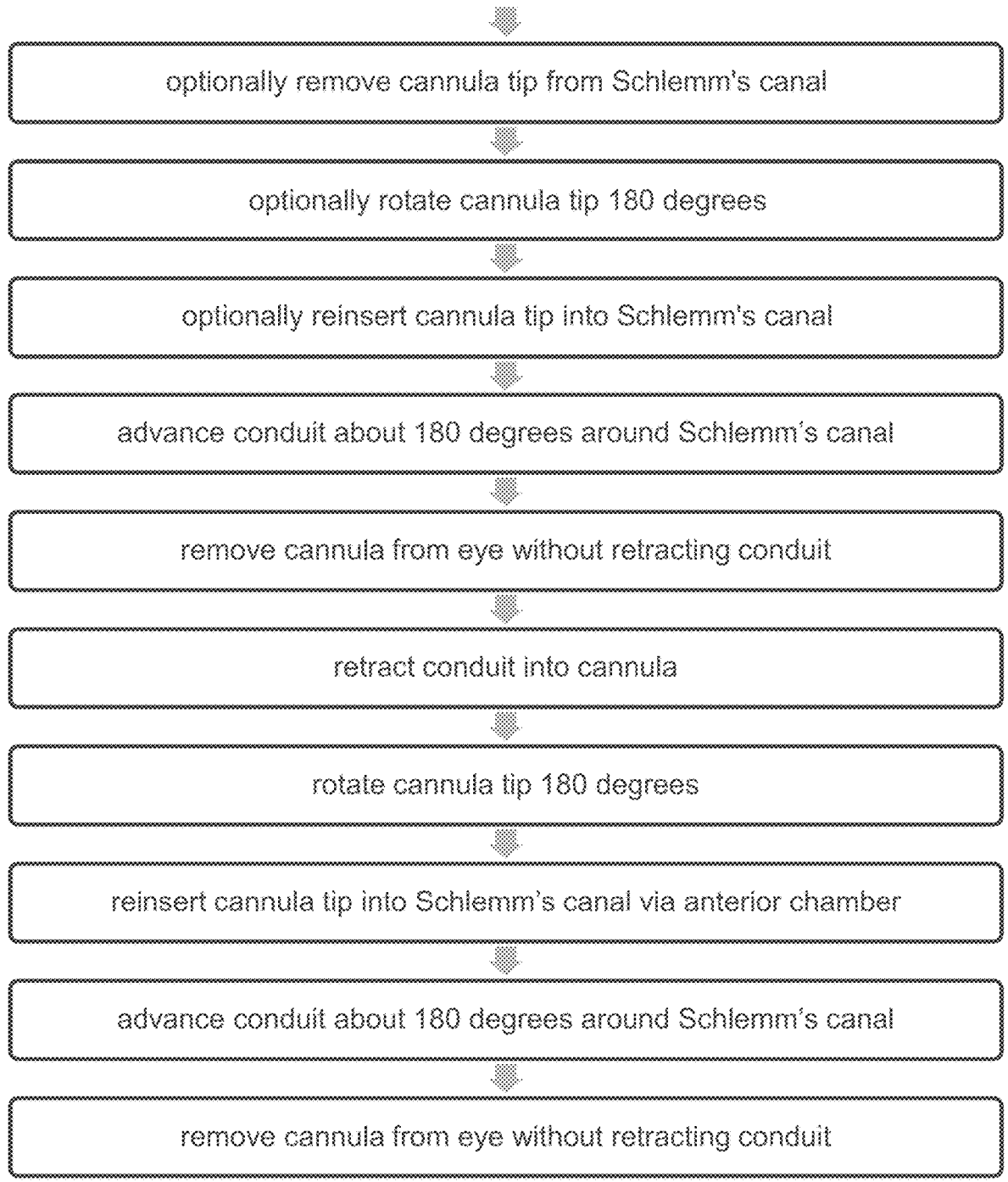

A flow chart of the method is shown in FIGS. 11A-11B. First, the delivery system (200) may be removed from its packaging. Next, the delivery system (200) may be loaded with viscoelastic fluid prior to the procedure. Suitable commercially available viscoelastics include but are not limited to Healon™, HealonGV™, Amvisc™, and PROVISC™. The commercially available viscoelastic cartridge may be attached externally to the delivery system via an exposed luer fitting at the proximal end of the housing (206). With the lock (212) attached to the housing (206), such that the pin (228) of the lock holds the reservoir (226) in place, the viscoelastic fluid may be injected from the viscoelastic cartridge into the reservoir (226) of the delivery system (200). It may be desirable to hold the delivery system (200) and viscoelastic cartridge upright during injection. The viscoelastic fluid may be injected until viscoelastic flow from the distal tip of the cannula (208) is visualized. The viscoelastic cartridge may then be removed from the delivery system. The lock (212) may then be removed from the delivery system (200) to release the reservoir (226).

To place the delivery system (200) in the eye, the surgeon may first view the anterior chamber and trabecular meshwork (with underlying Schlemm's canal) using an operating microscope and a gonioscope or gonioprism. Using a 0.5 mm or greater corneal, limbal, or sclera incision, the surgeon may then gain access to the anterior chamber. It may be desirable for the incision to be at least about 1 mm wide. A saline solution or viscoelastic composition may then be introduced into the anterior chamber to prevent its collapse. The surgeon, under direct microscopic visualization, may then advance the cannula (208) of the delivery system (200) through the incision towards the anterior chamber angle. When nearing the angle (and thus the trabecular meshwork), the surgeon may apply a gonioscope or gonioprism to the cornea to visualize the angle. The application of a viscous fluid (e.g., a viscoelastic composition as previously described) to the cornea and/or gonioscope or gonioprism may help to achieve good optical contact and negate total internal reflection thereby allowing visualization of the anterior chamber angle. As the surgeon visualizes the trabecular meshwork, the cannula (208) may then be advanced so that the bevel of at the distal end of the curved distal portion of the cannula (208) pierces the meshwork and is in communication with the lumen of Schlemm's canal.

The cannula (208) may be held securely against the angle while the elongate member is advanced into Schlemm's canal. To advance the elongate member into Schlemm's canal, a wheel (210) may be rotated in a first direction (e.g., by moving the exposed portion of the wheel distally) to advance the elongate member (250) up to about 180 degrees around Schlemm's canal (about 18 mm, about 19 mm, about 20 mm, about 18 mm to about 20 mm, or about 15 mm to about 25 mm of circumferential canal travel) in either a clockwise or counterclockwise direction. At this point, the elongate member (250) may be fully extended, and the wheel (210) may no longer be able to be rotated in the first direction. During this procedure, direct microscopic or gonioscopic visualization of the cannula tip may be maintained, and the anterior chamber may be maintained with viscoelastic or continuous balanced salt solution infusion.

Figure 12A:
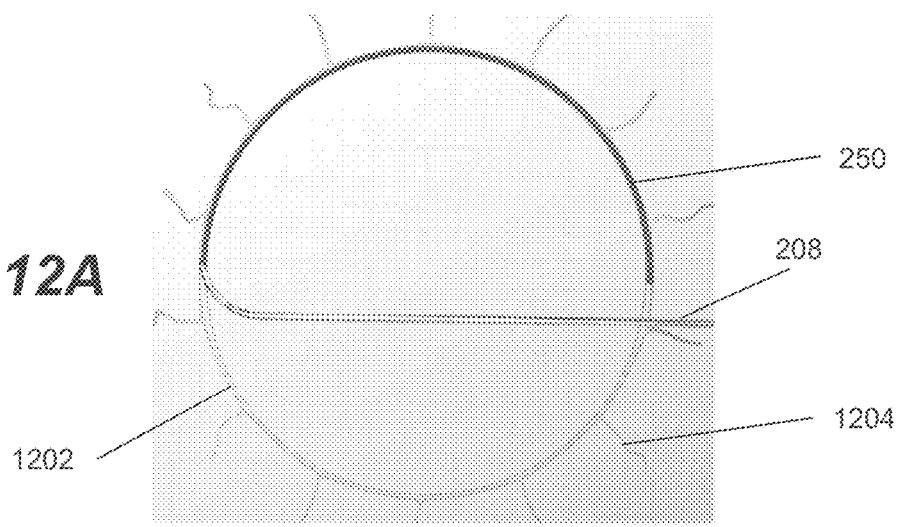
FIGS. 12A-12C depict delivery of fluid as a slidable elongate member is retracted as part of the method of FIGS. 11A-11B.
Figure 12B:
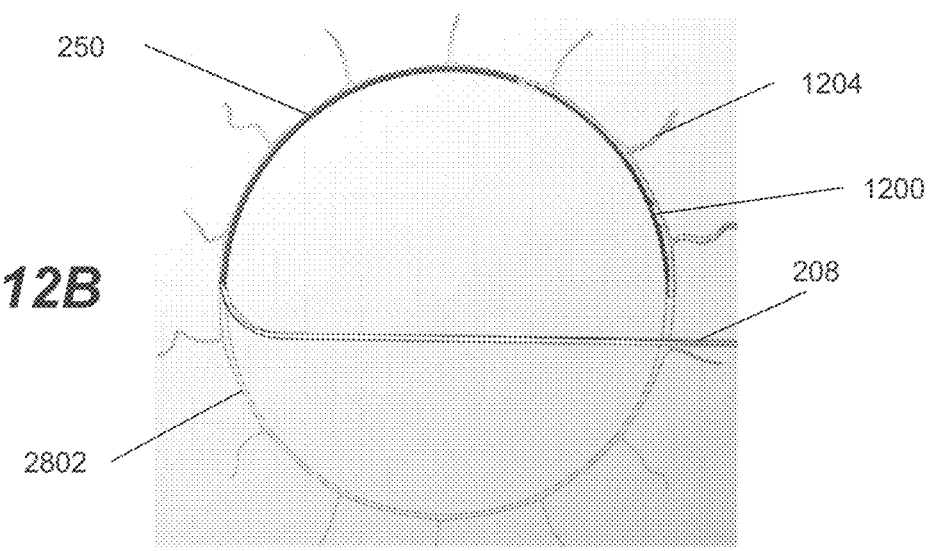
Figure 12C:
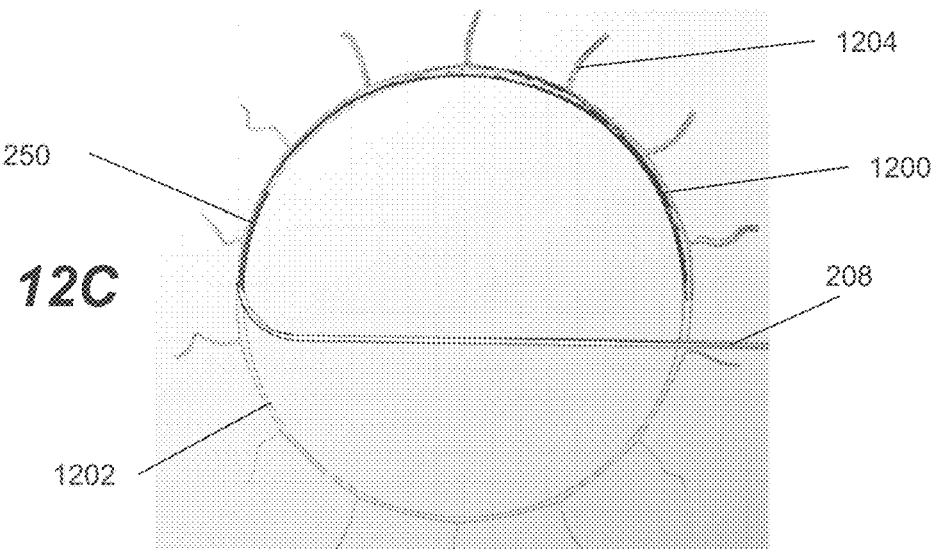

A wheel (210) may then be rotated in a second, opposite direction (e.g., by moving the exposed portion of the wheel proximally) to retract the elongate member (250). As the elongate member (250) is retracted, a specific predetermined volume of viscoelastic may be steadily delivered out of the lumen of the elongate member in a metered fashion, which may cause transluminal viscodilation of Schlemm's canal and/or collector channels. In some variations, full retraction of the elongate member (250) results in the delivery of between about 2 μl and about 9 μl of viscoelastic fluid (e.g., about 4.5 μl of viscoelastic fluid). In other variations, full retraction of the elongate member (250) results in the delivery of between about 5 μl and about 15 μl of viscoelastic fluid (e.g., about 10 μl of viscoelastic fluid). The wheel (210) may be configured to be incrementally rotated with audible and/or tactile clicks at incremental rotation; in some cases, between about 0.1 and about 1 μl of viscoelastic fluid may be delivered with each click. As illustrated in FIGS. 12A-12C, the delivery of viscoelastic (1200) to Schlemm's canal (1202) and collector channels (1204) during retraction of the elongate member (250) into the cannula (208) may result in the angle and length of delivery of viscoelastic to Schlemm's canal corresponding to the angle and length of the elongate member into the canal (e.g., up to about 180 degrees, and about 18 mm, about 19 mm, about 20 mm, about 18 mm to about 20 mm, or about 15 mm to about 25 mm of circumferential length). In some instances, viscoelastic may be used to tamponade any blood reflux back into the anterior chamber. It should be appreciated that in other variations, the elongate member (250) may be advanced up to about 360 degrees around Schlemm's canal in either a clockwise or counterclockwise direction, and retraction of the elongate member may result in delivery of viscoelastic to the full length of Schlemm's canal.

Viscoelastic may then be delivered to the other half of Schlemm's canal. The tip of the cannula (208) may be removed from Schlemm's canal and the delivery system (200) may be flipped, such that the cannula (208) is rotated 180 degrees to face the opposite direction. In some instances, the delivery system (200) may be flipped in the anterior chamber, without removing the cannula (208) from the eye. In other instances, the delivery system (200) may be removed from the eye, flipped, and reinserted into the incision. The tip of the cannula (208) may then be reinserted into Schlemm's canal via the same incision in the trabecular meshwork, and advancement and retraction of the elongate member (250) and delivery of viscoelastic fluid as described above may be repeated to viscodilate another portion of the canal (e.g., the remaining 180 degrees of Schlemm's canal), with the advancement of the elongate member in an opposite direction (i.e., counterclockwise if the first advancement was clockwise, or clockwise if the first advancement was counterclockwise). A procedure delivering viscoelastic fluid around 360 degrees of Schlemm's canal may deliver between about 4 μl and about 18 μl of viscoelastic fluid in total to the eye (e.g., about 9 μl of viscoelastic fluid), or between about 10 μl and 30 μl of viscoelastic fluid in total to the eye (e.g., about 20 μl of viscoelastic fluid).

The elongate member (250) may then be used to perform a transluminal trabeculotomy of up to 360 degrees. The cannula (208) may be held securely against the angle while the elongate member (250) is advanced into Schlemm's canal. In some variations, this advancement may be performed after viscoelastic fluid delivery without moving the tip of the cannula (208); that is, the elongate member (250) may be advanced in the same direction around Schlemm's canal as where fluid was delivered immediately prior. In other variations, the elongate member (250) may be advanced in the opposite direction. In these variations, the tip of the cannula (208) may be removed from Schlemm's canal and the delivery system (200) may be flipped, such that the cannula (208) is rotated 180 degrees to face the opposite direction. In some instances, the delivery system (200) may be flipped in the anterior chamber, without removing the cannula (208) from the eye. In other instances, the delivery system (200) may be removed from the eye, flipped, and reinserted into the incision. The tip of the cannula (208) may then be reinserted into Schlemm's canal via the same incision in the trabecular meshwork.

To advance the elongate member (250) into Schlemm's canal, a wheel (210) may be rotated in the first direction (e.g., by moving the exposed portion of the wheel distally) to advance the elongate member up to about 180 degrees around Schlemm's canal (about 18 mm, about 19 mm, about 20 mm, about 18 mm to about 20 mm, or about 15 mm to about 25 mm of circumferential canal travel). At this point, the elongate member (250) may be fully extended, and the wheel (210) may no longer be able to be rotated in the first direction. During this procedure, direct microscopic or gonioscopic visualization of the cannula tip may be maintained, and the anterior chamber may be maintained with viscoelastic or continuous balanced salt solution infusion.

Figure 13A:
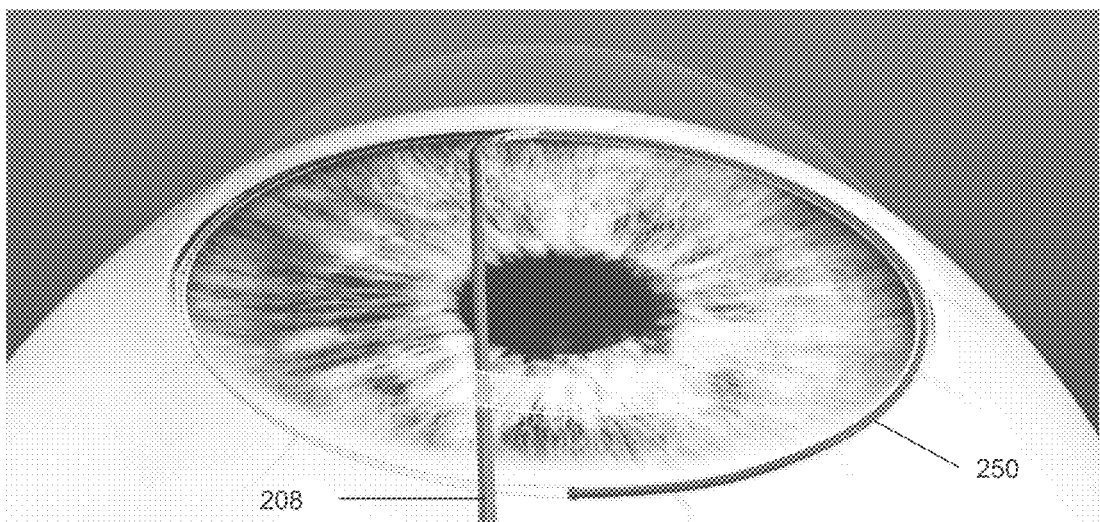
FIGS. 13A-13C depict disruption of the trabecular meshwork as part of the method of FIGS. 11A-11B.
Figure 13B:
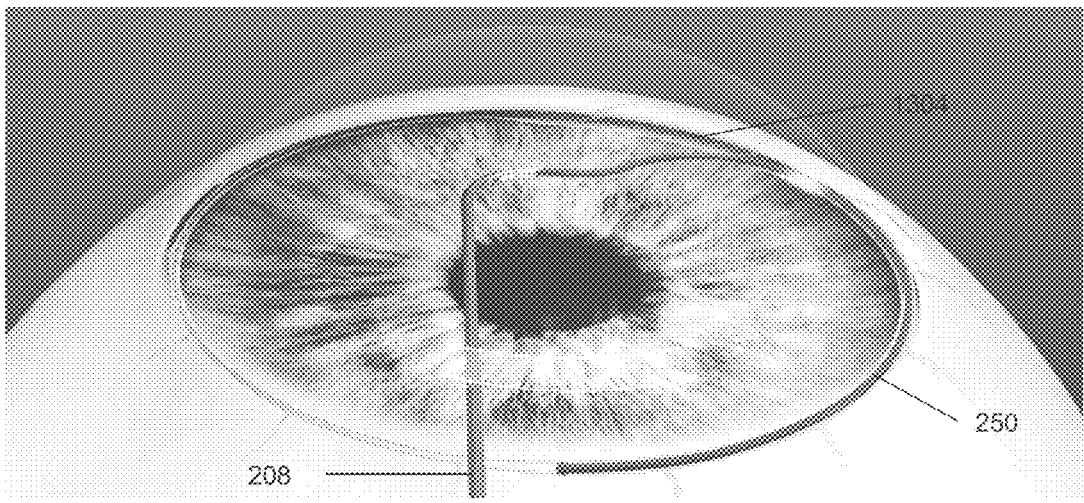
Figure 13C:
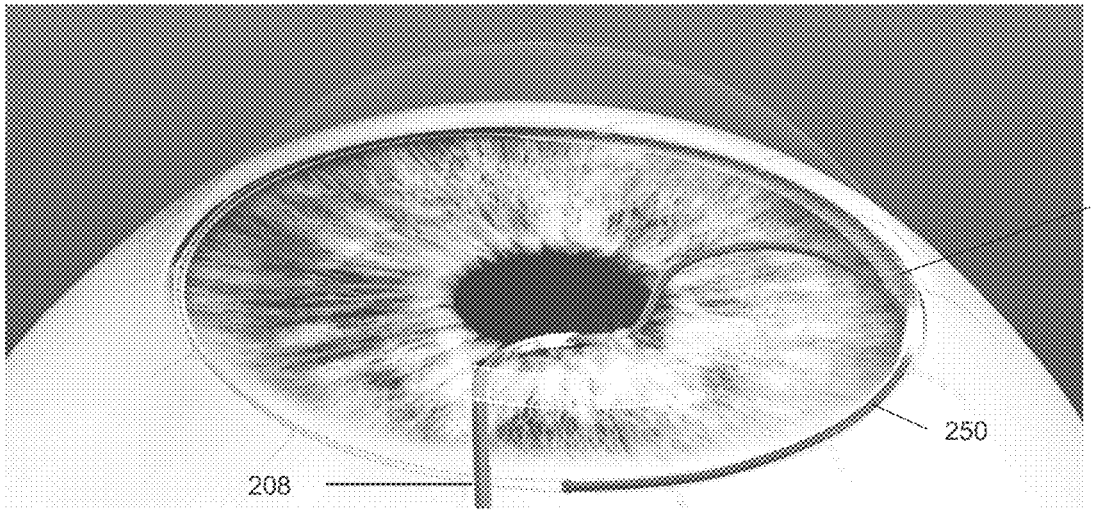

Once the elongate member is advanced, the cannula (208) may be removed from the eye through the incision without retracting the elongate member (250), as shown in FIGS. 13A-13C. This may cause the elongate member (250) to tear or cut through the trabecular meshwork (1304). In some instances, it may be desirable to bias the distal tip of the cannula (208) toward the trabecular meshwork being cut; this may in some instances help to prevent the elongate member (250) from slipping out of the canal during cannula removal. Removal of the cannula (208) without retraction of the elongate member (250) may cause the elongate member to transmit the force from removing the cannula (208) into a force that tears or cuts the trabecular meshwork (1304). Removal of the cannula (208) thus results in an "unzipping" effect to tear or cut the trabecular meshwork (1304). That is, the trabecular meshwork (1304) is torn by the body of the elongate member (250) from its proximal to distal end. First, force on the trabecular meshwork (1304) from the proximal end of the body of the elongate member (250) causes the trabecular meshwork to tear near the insertion point of the cannula (208). As the cannula (208) continues to be withdrawn from the eye, the body of the elongate member (250) continues to tear through the trabecular meshwork (1304), toward the distal tip of the elongate member. It should be noted that this method causes the trabecular meshwork to be progressively torn from a first location (the proximal end of the extended elongate member, near the insertion point of the cannula) to a second location (the distal end of the extended elongate member), as opposed to being cut or torn simultaneously along the distance from the first location to the second location. Furthermore, it should be noted that in this method each portion of the trabecular meshwork is not torn by a single feature of the elongate member (e.g., a distal end of the elongate member upon advancement or retraction); rather, each portion of the trabecular meshwork is torn by the portion of the elongate member adjacent to it after the elongate member has been advanced. It should be appreciated that in other variations, the elongate member may be advanced up to about 360 degrees around Schlemm's canal in either a clockwise or counterclockwise direction, and removal of the cannula may result in the tearing or cutting of approximately 360 degrees of the trabecular meshwork.

After the delivery system is fully removed from the eye, the elongate member (250) may be retracted back into the cannula by rotating a wheel (210) in the second direction (e.g., by moving the exposed portion of the wheel distally). During this retraction of the elongate member, no fluid may flow out of the distal end of the elongate member. Once the elongate member (250) is fully retracted into the cannula (216), the delivery system (200) may be flipped, such that the tip of the cannula (208) is rotated 180 degrees to face the opposite direction. The cannula tip may then be advanced into the anterior chamber through the corneal or scleral incision, and the distal tip may be advanced into the same entry into Schlemm's canal. The method described above may then be repeated on the second half of Schlemm's canal to cut through the trabecular meshwork. In some instances, viscoelastic may be used to tamponade any blood reflux back into the anterior chamber.

At the end of the procedure, the anterior chamber may be irrigated (e.g., with balanced salt solution) through the corneal wound (either manually or automated). A balanced salt solution or viscoelastic may be used to reform the anterior chamber as needed to achieve physiologic pressure and further tamponade any blood reflux from the collector channels back into the anterior chamber. If necessary, a suture may be used to seal the corneal or scleral incision. Postoperatively, an antibiotic or antiseptic, mydriatic agent, or a miotic agent, may be used as appropriate. For example, a miotic eye drop may be used for weeks or months to help prevent synechiae formation and angle closure.

Thus, it should be appreciated that the delivery system (200) may be configured to perform a procedure involving a first portion comprising delivering a viscoelastic fluid to dilate Schlemm's canal and/or the collector channels, and a second portion comprising cutting or tearing the trabecular meshwork. In some variations, the entire procedure may be performed using a single corneal incision and a single access point in Schlemm's canal. In some variations, delivering the viscoelastic fluid may comprise two steps (delivering the viscoelastic fluid to a first length of Schlemm's canal and delivering the viscoelastic fluid to a second length of Schlemm's canal); and cutting or tearing the trabecular meshwork may comprise two steps (cutting or tearing a first length of the trabecular meshwork and cutting or tearing a second length of Schlemm's canal). In other variations, delivering the viscoelastic may comprise one step, and cutting or tearing the trabecular meshwork may comprise one step.

The delivery system (200) may be configured such that it switches from a first configuration in which it delivers fluid upon elongate member retraction to a second configuration in which it does not deliver fluid upon elongate member retraction. In some variations, the switch may occur automatically after the delivery system (200) has undergone a predetermined cumulative amount of elongate member retraction. For example, the delivery device (200) may be configured such that it switches from the first configuration to the second configuration after a cumulative amount of elongate member retraction equal to the full circumference of Schlemm's canal (e.g., between about 38 mm and about 40 mm). In other variations, the switch may be carried out manually by the operator.

It should be appreciated that the viscoelastic fluid may be delivered to and the trabecular meshwork torn in the same length of the canal (including all of the canal), or viscoelastic fluid may be delivered to and the trabecular meshwork torn in different lengths of the canal. It should also be appreciated that the viscoelastic fluid delivery may comprise one, two, three, four, or more steps, and/or tearing the trabecular meshwork may comprise one, two, three, four, or more steps. In one variation, the method may comprise dilating 360 degrees of Schlemm's canal; and tearing the trabecular meshwork of 360 degrees of Schlemm's canal. In one variation, the method may comprise dilating 180 degrees of Schlemm's canal; dilating the other 180 degrees of Schlemm's canal; tearing the trabecular meshwork of 180 degrees of Schlemm's canal; and tearing the trabecular meshwork of the other 180 degrees of Schlemm's canal. In another variation, the method may comprise dilating 90 degrees of Schlemm's canal; dilating another 90 degrees of Schlemm's canal; tearing the trabecular meshwork of 90 degrees of Schlemm's canal; and tearing the trabecular meshwork of another 90 degrees of Schlemm's canal. The dilated 180 degrees may entirely overlap with the torn 180 degrees; it may not overlap at all; or it may partially overlap. In another variation, the method may comprise dilating 180 degrees of Schlemm's canal; dilating the other 180 degrees of Schlemm's canal; tearing the trabecular meshwork of 90 degrees of Schlemm's canal; and tearing the trabecular meshwork of another 90 degrees of Schlemm's canal. In another variation, the method may comprise dilating 90 degrees of Schlemm's canal; dilating another 90 degrees of Schlemm's canal; tearing the trabecular meshwork of 180 degrees of Schlemm's canal; and tearing the trabecular meshwork of the other 180 degrees of Schlemm's canal.

Ab-Externo Approach

In other variations, the methods may comprise accessing Schlemm's canal through an ab-externo approach. An ab-externo approach to delivering a fluid composition and/or performing a trabeculotomy may include additional or slightly different steps. For example, the creation of tissue flaps, suturing, etc., may be part of the ab-externo method. In general, the ab-externo method may include the following steps.

First, under microscopic visualization, conjunctiva may be incised, a scleral flap may be created, and tissue may be dissected to identify the ostia into Schlemm's canal. The anterior chamber may be separately infused with saline or may have a viscoelastic composition placed in it to prevent collapse of the anterior chamber angle. The operation may be done as a standalone procedure or in combination with cataract surgery in one sitting. It may also be done before the cataract surgery portion or after it.

Using a delivery system described herein, the cannula may be advanced into Schlemm's canal and a elongate member coaxially disposed within the cannula lumen may be advanced into the canal under gonioscopic visualization. Once the elongate member has been positioned within the canal, a fluid composition, e.g., a viscoelastic fluid, may be continuously or intermittently delivered through the elongate member. The fluid composition may exit the lumen of the elongate member through its distal end (e.g., the through the distal tip), or through openings or fenestrations provided along its shaft, or a combination of both. The openings or fenestrations may be spaced along the axial length of the elongate member in any suitable manner, e.g., symmetrically or asymmetrically along its length. Other substances such as drugs, air, or gas may be delivered in the same manner if desired. The elongate member may be repositioned by retraction or repeated advancement and retraction. In some variations, the delivery system may further be used to perform a trabeculotomy as described herein. The delivery system may then be removed from the eye.

The configurations of the delivery systems described here may be advantageous in many different respects. In one aspect, the delivery system may be capable of being used in an ab-interno method of delivering a fluid composition into the canal. In another aspect, the delivery system may be capable of being used in an ab-interno method of performing a trabeculotomy with an elongate member. In another aspect, the delivery system cannula may be configured to allow easy and atraumatic access to Schlemm's canal. Furthermore, the delivery system may be configured in a manner that gives the surgeon greater freedom of use, all in a single instrument. For example, the handle of the system may be configured so that it can be used with either side up (i.e., by flipping over the handle or rotating the cannula). Thus, the delivery system may be designed to be used in a clockwise or counterclockwise direction with either hand and in either eye. For example, the delivery system may be capable of being used with the right or left hand to access Schlemm's canal in a counterclockwise fashion, or used with the right left hand to access the canal in a counterclockwise fashion, in either eye. Thus, access to the canal from all four quadrants of the eye can be achieved. In yet a further respect, the delivery system comprises single-handed, single-operator controlled devices configured to provide a force sufficient to disrupt Schlemm's canal and surrounding tissues to improve flow through the trabeculocanalicular outflow pathway. The systems generally combine access cannulas, delivery elongate members, elongate member advancement mechanisms, and viscoelastic fluids into a single device so that one person or one hand can advance the elongate member or deliver the fluid.

Methods of Manufacturing the Cannula

As mentioned above, the cannulas described here may be configured to both pierce the trabecular meshwork or other tissue, and reversibly deliver the elongate member without cutting, breaking, or otherwise damaging the elongate member. In order to accomplish this dual purpose, the cannulas may be manufactured to comprise distal ends with both sharp and dull or blunt portions. Generally, methods of manufacturing the cannulas described here may comprise creating a bevel at a distal tip of the cannula, sharpening the distal end of the distal tip to create a sharpened piercing tip, smoothing a portion of the distal tip of the cannula, and bending a portion of the cannula along a longitudinal axis of the cannula. In some variations, methods may also comprise acquiring a cannula of an appropriate working length, roughening an outer surface of the cannula, applying a protective covering to a portion of the distal tip, polishing a portion of the cannula, and cleaning the cannula.

Figure 7:
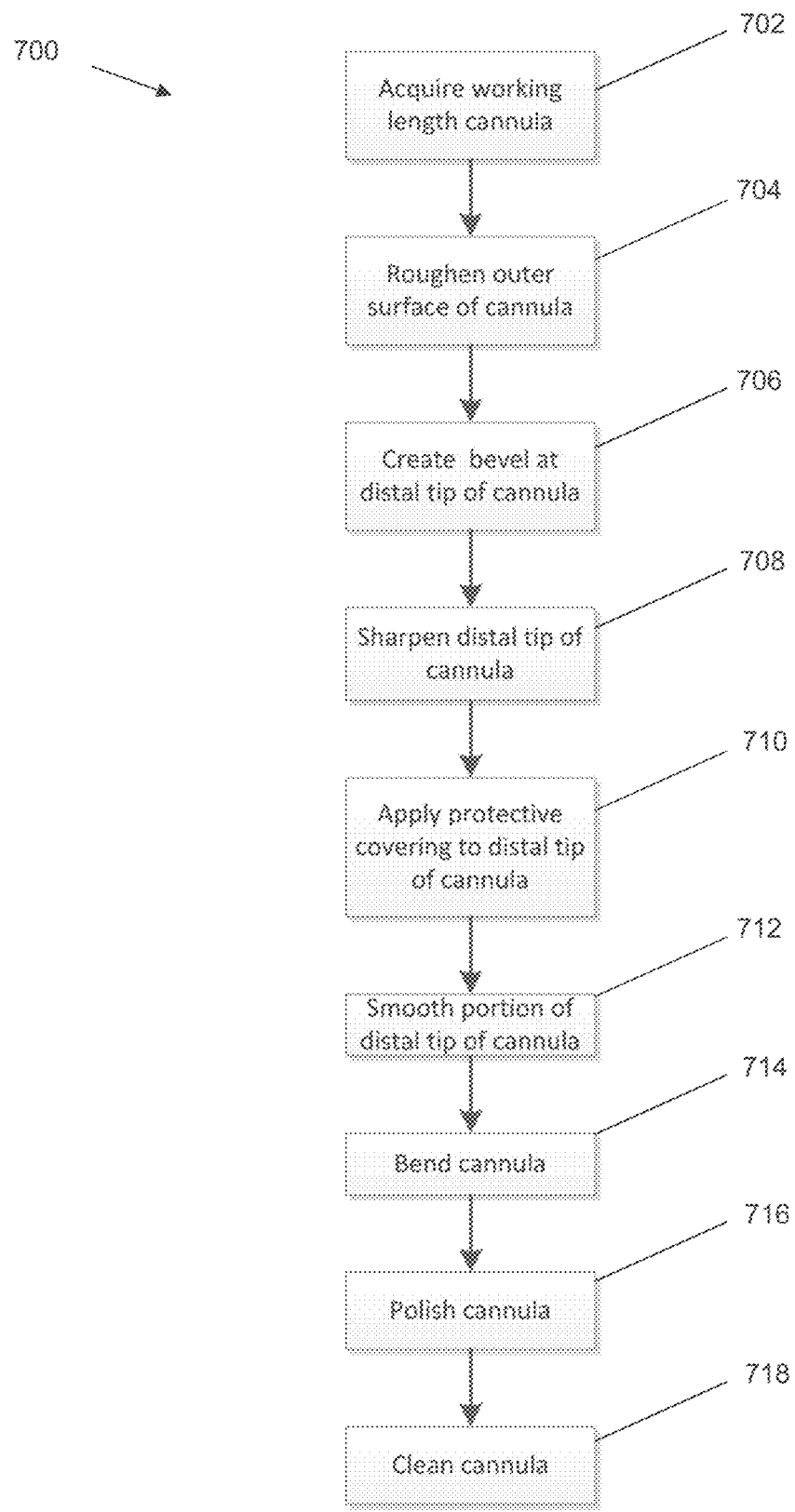
FIG. 7 is a flow-chart illustrating an exemplary manufacturing method for a cannula that may be used with the devices, systems, and methods described here.

FIG. 7 depicts an exemplary method of manufacturing a cannula for use with the devices, systems, and methods described here. As shown there, a method of manufacturing the cannula (700) may comprise acquiring a cannula of an appropriate working length (702), roughening an outer surface of the cannula (704), creating a bevel at a distal tip of the cannula (706), sharpening the distal tip of the cannula (708), applying a protective covering to a portion of the distal tip of the cannula (710), smoothing a portion of the distal tip of the cannula (712), bending the cannula (714), polishing the cannula (716), and cleaning the cannula (1418). It should be appreciated that while the method steps in FIG. 7 are depicted in a particular order, many of the steps may be completed in a different order, and some of the steps may be optional all together, as is discussed in more detail below.

To begin the process, a cannula of a suitable working length may be acquired (702). The cannulas may be purchased pre-cut to a desired working length, or the raw material used to create the cannulas, for example, stainless steel hypodermic tubing, may be purchased in bulk quantities and cut to the appropriate length during the cannula manufacturing process. The cannulas may be examined for damage or other visual defects upon acquisition and throughout the manufacturing process. In some variations, the working length (i.e., a length suitable for handling the cannula during manufacturing) may correspond to the final desired length of the cannula. In other variations, for ease of manufacturing for example, the working length may be longer than the desired length, and the cannula may be cut or shortened to the final desired length at any point during the manufacturing process (e.g., by cutting the proximal end of the cannula), including as the last step of the process. Exemplary working lengths include, but are not limited to, between about 50 mm and about 70 mm, between about 40 mm and about 90 mm, and more specifically, about 60 mm.

The proximal end of the cannula may be cut, treated, and/or finished at any time during the manufacturing process. In some instances, the proximal end of the cannula may be square cut (i.e., cut substantially perpendicular to the longitudinal axis of the cannula). The edges of the proximal end may be smoothed or rounded using any suitable method, for example, by media blasting. This smoothing of the proximal end of the cannula may prevent cutting, tearing, or otherwise damaging the elongate member. For example, smoothing the proximal end may remove any sharp edges or jagged surfaces therefrom, and may remove any debris or deposits remaining in the proximal end of the lumen from the cutting process. The proximal end of the cannula may be inspected after smoothing, and if sharp or serrated edges remain, the proximal end may be further smoothed.

In some variations, an outer surface of the cannula may optionally be roughened (704) or texturized, which may assist in adhering the cannula to the handle. For example, in some instances, a proximal or central portion of an outer surface of the cannula may be abrasively blasted to create a textured or rough surface to which adhesive may be applied. Abrasively blasting an outer surface of the cannula may increase the surface area of the abrasively blasted portions, which may provide for better adhesion between the handle and the cannula.

As described above, the distal end of the cannula may be beveled. The bevel may be created (706) by cutting or grinding the distal end of the cannula at an angle relative to the longitudinal axis of the cannula. More specifically, the bevel may be installed such that it traverses and is transverse to the lumen of the cannula. As described above, FIG. 3 depicts a side view of a cannula (300) comprising a bevel (312) at its distal tip (306). The bevel (312) may comprise an angle (A) between about 5 degrees and about 85 degrees. As mentioned above, the angle (A) may be important to properly puncture the trabecular meshwork and access Schlemm's canal without damaging other surrounding tissue, and/or to adequately visualize advancement and retraction of the elongate member. In some variations, the angle (A) may be about 5, 10, 15, 20, 25, 30, 35, 40, 45, 50, 55, 60, 65, 70, 75, 80, or 85 degrees. In some variations, the angle (A) may be between about 23 degrees and about 27 degrees. In some of these variations, the angle (A) may be about 25 degrees.

As described above, FIG. 5 depicts a perspective view of a distal tip (502) of a cannula (500) after a bevel has been created. As shown, the beveled distal tip (502) now comprises a proximal end (508) and a distal end (510). Additionally, creating the bevel at the distal tip (502) may elongate the opening (512) at the distal tip (502) creating an elliptical, rather than circular, shaped opening. Thus, beveling the distal tip (502) may yield an elliptical shaped lumen opening that is angled such that the top of the elliptical opening is closer to the proximal portion of the cannula than the bottom of the elliptical opening. Also shown in FIG. 20 are inner and outer circumferential edges (504, 506).

Although installing the bevel may create sharp edges, and in some instances, a sharp distal tip, it may be desirable to further sharpen a portion of the distal tip of the cannula to achieve easier access into Schlemm's canal with higher precision. Accordingly, in some instances, after the bevel has been created, the distal tip may be further sharpened (708) to create a sharpened piercing tip that may further assist in piercing the trabecular meshwork. The distal tip may be sharpened using any suitable means, for example, by grinding or otherwise removing a portion of the external surface and/or a portion of the outer circumferential edge of the distal end of the distal tip of the cannula. To minimize unwanted sharp edges that may damage the elongate member, it may be desirable to maintain as much of the wall thickness at the distal tip as possible, and to ensure that the thickness of the wall is uniform. It may also be beneficial to prevent cannula material or other sharpening byproducts from forming, building-up, adhering to, or otherwise being deposited on an internal surface of the cannula in the lumen. Such materials may become debris create raised or sharp surfaces or edges that may cut or damage the elongate member when the delivery system is in use.

As described above, FIGS. 6A and 6B depict perspective and front views, respectively, of a variation of a distal tip (600) of a cannula comprising both a bevel (602) and a sharpened piercing tip (614). The distal tip (600) also comprises a proximal end (608), a distal end (610), inner and outer circumferential edges (604, 606), and a lumen opening (612). The sharpened piercing tip (614) may be created by grinding the distal end (610) of the distal tip (600), thereby creating two angled surfaces (616) that converge to form a sharp point. The angled surfaces (616) may be formed at any suitable angle that results in a sharpened piercing tip (614). For example, in some instances, the angle surfaces (616) may have an angle (B) relative to the longitudinal axis of the distal tip (600) of about 20, 25, 30, 35, 40, 45, or 50 degrees, between about 25 and about 50 degrees, or between about 37.5 and about 42.5 degrees. Accordingly, in some variations, the angle between the two angled surfaces (616) may be between about 50 and about 100 degrees. It should be appreciated that although the distal tip (600) is depicted with two angled surfaces, a distal tip with a single angled surface may also be used.

Turning back to FIG. 7, the method for manufacturing the cannula (700) may further comprise smoothing a portion of the distal tip (712) of the cannula. In variations in which the distal tip of the cannula is sharpened, as described above with respect to FIGS. 6A and 6B, the method may further comprise applying a protective covering (710) over the sharpened portion of the distal tip, for example, the distal end of the sharpened piercing tip (614) and/or the angled surfaces (616), prior to smoothing the distal tip (712). In variations in which the distal tip is not sharpened after it is beveled, it may still be desirable to apply a protective covering over the distal end of the distal tip (as described with respect to FIG. 5 above). Applying a protective covering may help to maintain the sharp edge(s) during smoothing.

As mentioned above, the distal tip of the cannula may be configured to both pierce tissue, and to deliver a elongate member. The elongate member itself may be susceptible to being pierced, cut, severed, or otherwise damaged by the cannula. In order to protect the elongate member, it may be important to smooth or deburr the surfaces and/or edges of the distal tip of the cannula that the elongate member may contact. For example, referring again to FIGS. 6A and 6B, in some variations, a portion of the inner and/or outer circumferential edges (604, 606), the surface between the edges (618), and/or the internal and/or external surfaces of the cannula adjacent to the opening (612), may be smoothed. This may even out and/or dull these edges and surfaces. For example, it may be desirable to smooth a portion of the inner circumferential edge (604) at the proximal or distal end (608, 610) of the distal tip (600), or to smooth the entire inner circumferential edge. In some instances, a portion of the outer circumferential edge (606) may also be smoothed while maintaining the sharp edges of the distal tip (e.g., the sharpened piercing tip). For example, a portion of the outer circumferential edge (606) may be smoothed at the proximal end (608) of the distal tip (600), or the entire outer circumferential edge (606), up to the angled surfaces (616) may be smoothed. Additionally, it may be desirable to smooth or deburr the surface between the edges (618) and/or the internal or external surface of the cannula adjacent to the opening (612) at the proximal end (608) or distal end (610) of the distal tip (600), or circumferentially around the opening (612).

Portions of the distal tip (600) of the cannula may be deburred, smoothed, evened, rounded, dulled, or the like, using any suitable mechanism. For example, smoothing portions of the distal tip of the cannula may comprise mechanical and/or manual deburring, abrasive or soda media blasting, sanding, grinding, wire brushing, laser ablating, polishing (e.g., electropolishing), a combination thereof, or the like.

Turning back to FIG. 7, the method of manufacturing a cannula (700) may further comprise bending a distal potion of the cannula (714) to form the distal curved portion described above. Bending the catheter may properly orient the distal tip such that it may atraumatically puncture the trabecular meshwork. Referring back to FIG. 3, in some variations, the distal portion of the cannula may be bent such that the sharpened piercing tip is located along the outer radius (322) of the curved cannula. In some instances, the distal portion of the cannula may be bent to an angle between about 100 and about 125 degrees, about 115 and about 125 degrees, or to about 118 degrees relative to an external surface of a proximal portion of the cannula.

The distal portion of the cannula may be bent using any suitable mechanical or manual bending process. It may be important to select a bending process that does not alter the cross-sectional size and shape of the cannula during the bending process. Additionally, it should be appreciated that the cannula may be bent at any point in the manufacturing process, and bending need not occur after the distal tip of the cannula is smoothed, as depicted in the method (700) in FIG. 7.

The method of manufacturing a cannula (700) may optionally comprise polishing (716) all or a portion of the cannula, for example, the distal tip of the cannula. In variations in which the cannula is polished, polishing the cannula (716) may remove debris, markings, indentations, grooves, or the like, left on the surfaces of the cannula. These markings may be remnants from any part of the manufacturing process, and specifically may be from creating the bevel at the distal tip of the cannula (706), sharpening the distal tip of the cannula (708), and/or smoothing a portion of the distal tip of the cannula (712). Polishing the cannula (716) may be especially useful in variations in which smoothing a portion of the distal tip of the cannula (712) comprises a process that generally leaves debris or markings behind, for example, laser ablation. Polishing the cannula (716) may be completed using any suitable method, for example, electropolishing, staged media blasting using media with increasing grain size, or the like.

If desired, the cannula may be cleaned (718) prior to its installation into the delivery systems described here. For example, in some variations, the cannula may be passivated to remove iron oxide or other contaminants. In some instances, the cannula may be passivated using an acid like, for example, nitric oxide. In other variations, the cannula may be cleaned using cleansers, ultrasonic baths, or any other suitable cleaning process.

The cannula and/or the assembled delivery system may be sterilized, for example, using gamma irradiation. The gamma irradiation dose range may be, for example, between 25-40 kGy. Other irradiation energies may be used for sterilization, for example e-beam irradiation. Alternative sterilization methods include gas sterilization, for example ethylene oxide gas sterilization. In variations in which all or a portion of the systems are reusable, as described herein, these portions may be sterilized and reused. For example, in variations in which the handle is reusable and the cannula and elongate member are disposable, after use the used cannula and elongate member may be removed, the handle sterilized, and a new cannula and elongate member attached to the sterile handle.

While the inventive devices, systems, kits, and methods have been described in some detail by way of illustration, such illustration is for purposes of clarity of understanding only. It will be readily apparent to those of ordinary skill in the art in light of the teachings herein that certain changes and modifications may be made thereto without departing from the spirit and scope of the appended claims.

The invention claimed is:

1. A method for treating a condition of an eye comprising:
advancing a distal end of a cannula of a fluid delivery system into an eye, the fluid delivery system comprising a reservoir, a linear gear, and a linkage coupling the reservoir and the linear gear;
moving the linear gear relative to the linkage in a first direction with the fluid delivery system in a first configuration to deliver a fluid composition contained within the reservoir to the eye, wherein in the first configuration a first set of teeth on the linear gear prevents movement of the linear gear relative to the linkage in a second, opposite direction; and
transitioning the fluid delivery system from the first configuration to a second configuration in which a second set of teeth on the linear gear allows movement of the linear gear relative to the linkage in the first direction and second, opposite direction.

2. The method of claim 1, wherein the fluid delivery system further comprises an elongate member slidably positioned within the cannula and fluidly coupled to the reservoir, wherein the fluid composition is delivered to the eye via the elongate member.

3. The method of claim 2 further comprising, with the fluid delivery system in the first configuration, moving the linear gear and the linkage together in the second, opposite direction thereby moving the elongate member toward an extended position.

4. The method of claim 2 further comprising, with the fluid delivery system in the second configuration, moving the linear gear in the first direction thereby moving the elongate member toward a retracted position.

5. The method of claim 4, wherein moving the linear gear in the first direction in the second configuration moves the elongate member toward a retracted position without delivering the fluid composition to the eye.

6. The method of claim 1, wherein the transition from the first configuration to the second configuration is based on an amount of translation of the linkage relative to the linear gear.

7. The method of claim 1, wherein moving the linear gear in the first direction in the first configuration delivers a fixed amount of fluid per increment of movement.

8. The method of claim 1, wherein the first set of teeth is located in a proximal portion of the linear gear and the second set of teeth is located in a distal portion of the linear gear.

9. The method of claim 1, wherein the fluid delivery system is configured to provide haptic feedback during movement of the linear gear relative to the linkage in the second configuration.

10. The method of claim 1, wherein the first direction is proximal and the second, opposite direction is distal.

11. The method of claim 1, wherein in the first configuration, the linear gear is movable toward but not away from the reservoir, and in the second configuration, the linear gear is movable toward and away from the reservoir.

12. The method of claim 1, wherein in the second configuration, the second set of teeth applies a force to the linkage resisting a fluid pressure in the reservoir thereby preventing movement of the linear gear relative to the linkage in the second, opposite direction.

13. The method of claim 1, wherein, in the second configuration, movement of the linear gear relative to the linkage in the first direction flexes a flexible portion of the linkage in a first plane around the second set of teeth.

14. The method of claim 13, wherein in the second configuration, movement of the linear gear relative to the linkage in the second, opposite direction flexes the flexible portion of the linkage in a second plane around the second set of teeth.

15. The method of claim 14, wherein the flexible portion comprises a u-shaped bend.

16. The method of claim 14, wherein the first and second planes are perpendicular to each other.

17. The method of claim 1, wherein the fluid delivery system further comprises at least one rotatable wheel coupled to the linear gear.

18. A method for treating a condition of an eye comprising:
advancing a distal end of a cannula of a fluid delivery system into an eye, the fluid delivery system comprising a reservoir, a linear gear, and a linkage coupling the reservoir and the linear gear;
moving the linear gear relative to the linkage in a first direction, wherein movement of the linear gear in the first direction causes a distal portion of the linkage to flex in a first plane; and
moving the linear gear relative to the linkage in a second, opposite direction, wherein movement of the linear gear in the second opposite direction causes the distal portion of the linkage to flex in a second, different plane.

19. The method of claim 18, wherein the first and second planes are perpendicular to each other.

20. The method of claim 18, wherein the distal portion of the linkage comprises a u-shaped bend.

21. The method of claim 18, wherein the linear gear comprises a first set of teeth and a second set of teeth.

22. The method of claim 21, wherein the first set of teeth is proximal to the second set of teeth.

23. The method of claim 21, wherein the distal portion of the linkage comprises a notch configured to engage the linear gear.

24. The method of claim 23, wherein the notch applies a proximal force to the second set of teeth to oppose a distal force on the linear gear generated by the fluid composition.

\* \* \* \* \*